US00RE40624E

(19) United States
(12) Reissued Patent
Johnson et al.

(10) Patent Number: US RE40,624 E
(45) Date of Reissued Patent: Jan. 20, 2009

(54) COMPOSITIONS AND METHODS OF USING APOPTOSIS SIGNALING KINASE RELATED KINASE (ASKRK)

(75) Inventors: Jeffrey D. Johnson, Moraga, CA (US); Yun-Ping Zhou, East Brunswick, NJ (US); Kimberly Marlen, San Pablo, CA (US)

(73) Assignee: Metabolex, Inc., Hayward, CA (US)

(21) Appl. No.: 11/900,008

(22) Filed: Sep. 7, 2007

Related U.S. Patent Documents

Reissue of:
(64) Patent No.: 7,109,021
Issued: Sep. 19, 2006
Appl. No.: 10/980,974
Filed: Nov. 3, 2004

U.S. Applications:
(60) Provisional application No. 60/517,477, filed on Nov. 4, 2003.

(51) Int. Cl.
*C12N 15/56* (2006.01)
C12N 5/06; C12P 21/06; C07H 21/04

(52) U.S. Cl. ..... 435/252.3; 435/194; 435/320.1; 435/325; 435/69.1; 536/23.2

(58) Field of Classification Search ..... None
See application file for complete search history.

(56) References Cited

FOREIGN PATENT DOCUMENTS

| | | | |
|---|---|---|---|
| WO | WO 01/77338 | A2 | 10/2001 |
| WO | WO 02/46384 | A2 | 6/2002 |
| WO | WO 03/064639 | A1 | 8/2003 |

OTHER PUBLICATIONS

Butler, et al., "Beta–Cell Deficit and Increased Beta–Cell Apoptosis in Humans with Type 2 Diabetes." Jan. 2003, Diabetes, vol. 52, No. 1, 102–110.
Gotoh et al., "Reactive Oxygen Species– and Dimerization–induced Activation of Apoptosis Signal–regulating Kinase 1 in Tumor Necrosis Factor–α Signal Transduction", *J Biol Chem*, 1998, pp. 17477–17482, vol. 273.
Hatai et al., "Execution of Apoptosis Signal–regulating Kinase 1 (ASK1)–induced Apoptosis by the Mitochondria–dependent Caspase Activation", *J Biol Chem*, 2000, pp. 26576–26581, vol. 275.
Ichijo, et al., Induction of Apoptosis byASK1, a Mammalian MAPKKK That Activates SAPK/JNK and p38 Signaling Pathways, *Science*, 1997, pp. 90–94, vol. 275.
Johnson et al., "Mitogen–Activated Protein Kinase Pathways Mediated by ERK, JNK, and p38 Protein Kinases", *Science*, 2002, pp. 1911–1912, vol. 298.
Kagi et al., "TNF Receptor 1–Dependent β Cell Toxicity as an Effector Pathway in Autoimmune Diabetes", *J Immunol*, 1999, pp. 4598–4605, vol. 162.
Kaneto et al., "Apoptotic Cell Death Triggered by Nitric Oxide in Pancretic β–Cells", *Diabetes,* 1995, pp. 733–738, vol. 44.
Kyriakis et al., "Mammalian Mitogen–Activated Protein Kinase Signal Transduction Pathhways Activated by Stress and Inflammation", *Physiol Rev*, 2001, pp. 807–869, vol. 81.
Liu et al., "Thioredoxin Promotes ASK1 Ubiquitination and Degradation to Inhibit ASK1–Mediated Apoptosis in a Redox Activity–Independent Manner", *Circ Res*, 2002, pp. 1259–1266, vol. 90.
Mandrup–Poulsen, et al., "Human Tumor Necrosis Factor Potentiates Human Interleukin 1–Mediated Rat Pancreatic β–Cell Cytotoxicity", *J Immunol*, 1987, pp. 4077–4082, vol. 139.
Mathis et al., "β–Cell death during progression to diabetes", *Nature*, 2001, pp. 792–798, vol. 414.
Nishitoh et al., "ASK1 is essential for endoplasmic reticulum stress–induced neuronal cell death triggered by expanded polyglutamine repeats", *Genes and Development*, 2002, pp. 1345–1355, vol. 16.
Takeda et al., "Roles of MAPKKK ASK1 in Stress–Induced Cell Death", *Cell Structure and Function*, 2003, pp. 23–29, vol. 28.
Tibbles et al., "The stress–activated protein kinase pathways", *Cell Mol. Life Sci.,* 1999, pp. 1230–1254, vol. 55.
Tobiume et al., "ASK1 is required for sustained activations of JNK/p38 MAP kinases and apoptosis", *EMBO Reports*, 2001, pp. 222–228, vol. 2.
Tobiume et al., "Activation of Apoptosis Signal–Regulating Kinase 1 by the Stress–Induced Activating Phosphorylation of Pre–Formed Oligomer", *J Cell Physiology*, 2002, pp. 95–104, vol. 191.
Tournier et al., "Requirement of JNK for Stress–Induced Activation of the Cytochrome c–Mediated Death Pathway", *Science* 2000, pp. 870–874, vol. 288.
Zhou et al., "Apoptosis in Insulin–secreting Cells", *J Clin. Invest.*, 1998, pp. 1623–1632, vol. 101.
Database EMBL [Online] , Feb. 22, 2002 (Feb. 22, 2002), "ih13f08.y1 Human insulinoma Homo sapiens cDNA clone Image: 5' similar to SW:M3K4_Mouse 035099 Mitogen–Activated Protein Kinase 5;, mRNA sequence." XP002441451, retrieved from EBI Accession No. EMBL: BM508924, Database Accession No. BM508924.
Database EMBL [Online] Jan. 24, 2003 (Jan. 24, 2003), "Mus musculus mitogen–activated protein kinase kinase kinase 15, mRNA (cDNA clone Image: 4975522), containing frame–shift errors." XP00244152 retrieved from EBI Accession No. EBL: BC043943, Database Accession No. BC043943.
Mathis et al., "βCell death during progression to diabetes", *Nature*, 2001, pp. 792–798, vol. 434.

*Primary Examiner*—Robert B. Mondesi
*Assistant Examiner*—Kagnew H Gebreyesus
(74) *Attorney, Agent, or Firm*—Townsend and Townsend and Crew LLP

(57) ABSTRACT

The invention provides apoptosis signaling kinase related kinase (ASKRK) nucleic acid and polypeptide sequences and methods of using such sequences to identify modulators of ASKRK. Such modulators can be used for the treatment of diabetes or for delaying the onset of diabetes. The invention also provides methods of diagnosing diabetes or prediabetes and methods of making a prognosis based on the detection of ASKRK nucleic acids and proteins.

5 Claims, 9 Drawing Sheets

Figure 2

Top = Mouse ASKRK (partial coding)
Bottom = Human ASKRK (full coding)

```
                 .         .         .         .         .
  2 EGGRGPRRALRAVYVRSESSQGAAAGGGPEAGALKCLLRACEAEGAHLTS 51
    | | ||||||||||||||||||| || ||||||| .||||||||||||||
 52 ESGGGPRRALRAVYVRSESSQGGAA.GGPEAGARQCLLRACEAEGAHLTS 100

                 .         .         .         .         .
 52 VPFGELDFGETAVLDAFYDADVAIVDMSDISRQPSLFYHLGVRESFDMAN 101
    ||||||||||||||||||||||||:|||||:||||||||||||||||||||
101 VPFGELDFGETAVLDAFYDADVAVVDMSDVSRQPSLFYHLGVRESFDMAN 150

                 .         .         .         .         .
102 NVILYYDTDADTALSLKDMVTQKNTASSGNYYFIPYTVTPCADYFCCESD 151
    |||||:||||||||||||||||||||||||||||| |||| ||||||||
151 NVILYHDTDADTALSLKDMVTQKNTASSGNYYFIPYIVTPCTDYFCCESD 200

                 .         .         .         .         .
152 AQRRASEYMQPNWDTILGPLCMPLVDRFTSLLKDIRVTSCAYYKETLLND 201
    ||||||||||||| ||||||||||||| |||||| |||| |||||||||
201 AQRRASEYMQPNWDNILGPLCMPLVDRFISLLKDIHVTSCVYYKETLLND 250

                 .         .         .         .         .
202 IRKAREKYQGDELAKELTRIKFRMDNIEVLTSDIIINLLLSYRDIQDYDA 251
    ||||||||||:|||||| ||| |||| ||||||||||||||||||||||||
251 IRKAREKYQGEELAKELARIKLRMDNTEVLTSDIIINLLLSYRDIQDYDA 300

                 .         .         .         .         .
252 MVKLVETLKMLPTCDLADQHNIKFHYAFALNRRNSTGDREKALQVMLQVL 301
    ||||||||.||||||||||||| ||||||||||||||||||||||:|||||
301 MVKLVETLEMLPTCDLADQHNTKFHYAFALNRRNSTGDREKALQIMLQVL 350

                 .         .         .         .         .
302 QSCDHPAPDMFCLCGRIYKDIFLDSGCEEDASRDSAIEWYRKGFELQSSL 351
    |||||| |||||||||||||||||| |.:| ||||||||||||||||||
351 QSCDHPGPDMFCLCGRIYKDIFLDSDCKDDTSRDSAIEWYRKGFELQSSL 400

                 .         .         .         .         .
352 YSGINLAVLLIVSGQQFETSMELRKIGVRLNSLLGRKGSLEKMNNYWDVG 401
    |||||||||||||.|||||||:||||||||||||||||||||||||||||
401 YSGINLAVLLIVAGQQFETSLELRKIGVRLNSLLGRKGSLEKMNNYWDVG 450

                 .         .         .         .         .
402 QFFTVSMLASDIGKAVQAAERLFKLKPPVWYLRSLVQNLLLIQRFKKPIT 451
    |||.||||| |:||||||||||||||||||||||||||||.|||| |
451 QFFSVSMLAHDVGKAVQAAERLFKLKPPVWYLRSLVQNLLLIRRFKKTII 500

                 .         .         .         .         .
452 EHSPRQERLNFWLDIIFEATNEVTNGLRFPVLVIEPTKVYQPSYVSINNE 501
    ||||||||||||||||||||||||||||||||||||||||||||||||||
501 EHSPRQERLNFWLDIIFEATNEVTNGLRFPVLVIEPTKVYQPSYVSINNE 550

                 .         .         .         .         .
```

Figure 2
(continuation)

```
 502 AEERTVSLWHVSPTEMKQIHEWNFTASSIKGISLSKFDERCCFLYVHDNS 551
     ||||||||||||||||||.||||||||||||||||||||||||||||||
 551 AEERTVSLWHVSPTEMKQMHEWNFTASSIKGISLSKFDERCCFLYVHDNS 600
                 .         .         .         .         .
 552 DDFQIYFSTEDQCNRFCSLVKEMLNNGVGSTVELEGEADGDTLEYEYDHD 601
     ||||||||||:||.|| ||||||: |  |||||||| ||||||||||||
 601 DDFQIYFSTEEQCSRFFSLVKEMITNTAGSTVELEGETDGDTLEYEYDHD 650
                 .         .         .         .         .
 602 ANGERVVLGKGSYGIVYAGRDLSNQVRIAIKEIPERDIRYSQPLHEEIAL 651
     ||||||||||||.||||||||||||||||||||||||| ||||||||||||
 651 ANGERVVLGKGTYGIVYAGRDLSNQVRIAIKEIPERDSRYSQPLHEEIAL 700
                 .         .         .         .         .
 652 HKYLKHRNIVQYLGSVSENGYIKIFMEQVPGGSLSALLRSKWGPMKEPTI 701
     ||||||||||||||||||||||||||||||||||||||||||||||||||
 701 HKYLKHRNIVQYLGSVSENGYIKIFMEQVPGGSLSALLRSKWGPMKEPTI 750
                 .         .         .         .         .
 702 KFYTKQILEGLKYLHENQIVHRDIKGDNVLVNTYSGVVKISDFGTSKRLA 751
     ||||||||||||||||||||||||||||||||||||||||||||||||||
 751 KFYTKQILEGLKYLHENQIVHRDIKGDNVLVNTYSGVVKISDFGTSKRLA 800
                 .         .         .         .         .
 752 GINPCTETFTGTLQYMAPEIIDQGPRGYGAPADIWSLGCTIIEMATSRPP 801
     |:||||||||||||||||||||||||||||||||||||||||||||:||
 801 GVNPCTETFTGTLQYMAPEIIDQGPRGYGAPADIWSLGCTIIEMATSKPP 850
                 .         .         .         .         .
 802 FHELGEPQAAMFKVGMFKIHPEIPEALSAEARAFILSCFEPDPQKRVTAA 851
     |||||||||||||||||||||||||||||||||||||||||| || | |
 851 FHELGEPQAAMFKVGMFKIHPEIPEALSAEARAFILSCFEPDPHKRATTA 900
                 .         .         .         .         .
 852 DLLQEGFLRQVNKGKKNRIAFKPSEGVRSGTGTLALPSSGELVGSSSSEH 901
     :||.||||||||||||||||||||| | |   ||||. || . .|||||
 901 ELLREGFLRQVNKGKKNRIAFKPSEGPR.GV.VLALPTQGEPMATSSSEH 948
                 .         .         .         .         .
 902 GSISPDSDAQPDAFFEKVQVPKHQLSHLLSVPDESPALDDRSTALPPEER 951
     ||:||||||||||| ||: . |:| | |||||||||| ||:|| |  ||:|
 949 GSVSPDSDAQPDALFERTRAPRHHLGHLLSVPDESSALEDRGLASSPEDR 998
                 .         .         .         .         .
 952 DPGLFLLRKDSERRAILYRILWEEQNQVASNLQECVVQSSEELLLSVSHI 1001
     | ||||||||||||||||:||||||||||||||||| |||||| ||| ||
 999 DQGLFLLRKDSERRAILYKILWEEQNQVASNLQECVAQSSEELHLSVGHI 1048
                 .         .         .         .         .
1002 KQIIGILRDFIRSPEHRVMAATISKLKVDLDFDSSSINQIHLILFGFQDA 1051
     |||||||||||||||||||| ||||||||||||||||.||||:|||||||
1049 KQIIGILRDFIRSPEHRVMATTISKLKVDLDFDSSSISQIHLVLFGFQDA 1098
                 .         .         .         .         .
```

Figure 2
(continuation)

```
1052 VNRILRNHLIRPHWMFAMDNIIRRAVQAAVTILIPELQAHFEPASETEGV 1101
     ||:||||||||||||||||||||||||||||||||||.|||||  |||||
1099 VNKILRNHLIRPHWMFAMDNIIRRAVQAAVTILIPELRAHFEPTCETEGV 1148

1102 DKD.TEVEGDYPLVDLLSQEVHVTPRGTRPGSVAIQEGQPHQQDPSLQLS 1150
     |||  | |  ||      .      |  | ||    || |||||  ||||
1149 DKDMDEAEEGYP............P.ATGPG....QEAQPHQQHLSLQLG 1181

1151 KLRQETNRLWEHLVQKEKGVPESSSPNSRPENSRIVSPSVTVQIQWWYRE 1200
     .|||||||| ||||:||:  .          .          .
1182 ELRQETNRLLEHLVEKEREYQNLLRQTLEQKTQELYHLQLKLKSNCITEN 1231

1201 PSTPDGLGTDRELIDWLQLQGVDANTIEKIVEEDYTLSDILNDITKEDLR 1250
     |. | |  ||:||||||.||| || |||||||| ||||||||:|||||||
1232 PAGPYGQRTDKELIDWLRLQGADAKTIEKIVEEGYTLSDILNEITKEDLR 1281

1251 CLRLRGGVLCRLWHAVSQHRRQMQESSQ 1278
      ||||||.||||| ||||:||  ||.|:
1282 YLRLRGGLLCRLWSAVSQYRR.AQEASE 1308
```

COMPOSITIONS AND METHODS OF USING APOPTOSIS SIGNALING KINASE RELATED KINASE (ASKRK)

Matter enclosed in heavy brackets [ ] appears in the original patent but forms no part of this reissue specification; matter printed in italics indicates the additions made by reissue.

CROSS-REFERENCE TO RELATED APPLICATIONS

This application claims benefit of U.S. Provisional Application No. 60/517,477, filed Nov. 4, 2003, which is herein incorporated by reference.

BACKGROUND OF THE INVENTION

In Type II diabetes, there is a progressive decline in insulin secretory function in beta cells in the face of ongoing insulin resistance. Currently available therapies are unable to prevent this decline (Diabetes 44:1249–1258, 1995; DeFronzo, Diabetes 37:667–687, 1988). Insulin resistance alone is not sufficient to cause Type II diabetes, and in fact, many individuals maintain insulin resistance for extended periods without becoming diabetic due to effective compensation by increased insulin secretion (Polonsky, Int J Obes Relat Metab Disord 24 Suppl 2:S29–31, 200). Insulin-resistant rats and mice display a compensatory increase in beta cell mass (Hribal, et al., Am J Physiol Endocrinol Metab 282:E977–981, 2002); the same phenomenon appears to occur in insulin resistant, but non-diabetic, (usually obese) humans (Kloppel, et al., Surv Synth Pathol Res 4:110–125, 1985; Butler, et al., Diabetes 52:102–110, 2003). In rodents, beta cell mass appears to be regulated by a changing balance between the positive effects of beta cell replication and neogenesis and the negative effects of beta cell apoptosis (Bonner-Weir, J Mol Endocrinol 24:297–302, 2000; Bonner-Weir, Trends Endocrinol Metab 11:375–378, 2000; Pick, et al., Diabetes 47:358–364, 1998; Finegood, et al., Diabetes 50:1021–1029, 2001). In humans, the onset of Type II diabetes due to insufficient increases (or actual declines) in beta cell mass is apparently due to increased beta cell apoptosis relative to non-diabetic insulin resistant individuals (Butler, et al., Diabetes 52:102–110, 2003). Agents which could specifically prevent this increase in beta cell apoptosis may therefore prevent insulin resistant individuals from developing Type II diabetes.

Beta cell death and apoptosis are also central to the onset of Type I diabetes, although the mechanisms that lead to loss of beta cell mass are primarily T-cell mediated in Type I and this is not the case in the majority of Type II cases (Mathis, et al., Nature 414:792–798, 2001). In Type I diabetes, recruitment and activation of T-cells and macrophages leads to an intra-islet environments rich in cytokines (interleukin (IL) 1-β interferon (IFN)-γ and tumor necrosis factor (TNF)-α), reactive oxygen species and nitric oxide (NO), each of which can promote beta cell apoptosis in vitro (Eizirik and Darville, Diabetes 50 Suppl 1:S64–69, 2001). Physiological beta cell apoptosis may actually trigger the immune response that results in wholesale islet destruction (Mathis, et al., Nature 414:792–798, 2001).

The mechanisms that lead to increased beta cell apoptosis are multiple and interlacing and they are as yet incompletely understood. Tumor necrosis factor (TNF)-α, which interacts with receptors TNF-RI and TNF-RII in both its membrane bound and soluble forms, can contribute to beta cell death in vitro (Kaneto, et al., Diabetes 44:733–738, 1995; Mandrup-Poulsen, et al., J. Immunol 139:4077–4082, 1987). In the NOD mouse model of Type I diabetes, TNF-RI deficiency can prevent the onset of diabetes, presumably through reduction in beta cell death or apoptosis (Kagi, et al., J Immunol 162:4598–4605, 1999). Various modes of stress can also contribute to beta cell apoptosis (Zhou, et al., J Clin Invest 101:1623–1632, 1998).

Although there are likely to be apoptotic modalities that are relatively unique to the beta cell, there are some general mechanisms of programmed cell death that occur in many cell and tissues that form fundamental pathways for cytotoxic response to UV irradiation, X-rays, thermal and osmotic shock, endoplasmic reticulum (ER) stress as well as the response to proinflammatory cytokines such as IL-1 beta and TNF-alpha. Some of these pathways are composed of cascades of mitogen-activated protein kinases (MAP kinases) (Kyriakis and Avruch, Physiol Rev 81:807–869, 2001). Cytotoxic stresses activate MAP kinase kinase kinases (MAPKKKs), which phosphorylate and activate MAP kinase kinases (MAPKKs), which in turn phosphorylate and activate MAP kinases such as ERK, JNK1-3, and p38 (Johnson and Lapadat, Science 298:1911–1912, 2002; Tibbles and Woodgett, Cell Mol Life Sci 55:1230–1254, 1999). JNKs, which phosphorylate and activate the transcription factor c-Jun among other substrates, are critical mediators of apoptosis (Tournier, et al., Science 288:870–874, 2000).

Apoptosis signaling kinase (ASK)-1/MAPKKK5 is a ubiquitously expressed component of the kinase cascade that activates JNK and p38 (Takeda, et al., Cell Struct Funct 28:23–29, 2003). ASK1 directly phosphorylates MKK4 (SEK1)/MKK7 and MKK3/MKK6, which in turn phosphorylate the JNKs and p38 (Ichijo, et al., Science 275:90–94, 1997). A constitutively active form of ASK1 is obtained by truncating an N-terminal regulatory domain; expression of this active kinase leads to apoptosis via mitochondria-dependent capase activation (Hatai, et al., J Biol Chem 275:26576–26581, 2000). Cells from mice that lack ASK1 are resistant to the apoptotic effects of oxidative stress and TNF-α (Tobiume, et al., EMBO Rep 2:222–228, 2001).

The role of ASK1 in oxidative stress-initiated apoptosis may be mediated in part by a direct physical interaction with the redox-regulatory protein thioredoxin (TRX) (Saitoh, et al., Embo J 17:2596–2606, 1998). Trx inhibits ASK1 kinase activity upon binding to the N-terminal domain that is lacking in the constitutively active form of ASK1. The interaction between ASK1 and Trx is dependent on Trx being in the reduced form; this provides a mechanism by which the redox state of the cell can regulate ASK1 kinase activity (Liu and Min, Circ Res 90:1259–1266, 2002). Accordingly, reactive oxygen species such as $H_2O_2$ cause dissociation of Trx-ASK1 complexes and lead to ASK1 activation (Gotoh and Cooper, J Biol Chem 273:17477–17482, 1998; Tobiume, et al., J Cell Physiol 191:95–104, 2002).

There is also evidence that ASK1 promotes apoptosis in cells undergoing endoplasmic reticulum (ER) stress. The ER protein IRE1 forms a complex with ASK1 and a TNF receptor interacting protein TRAF2 in cells undergoing ER stress, and this leads to activation of the ASK1-JNK pathway. The apoptosis initiated by this pathway is reduced in cells that lack ASK1 (Nishitoh, et al., Genes Dev 16:1345–1355, 2002).

BRIEF SUMMARY OF THE INVENTION

This invention is based on the discovery of a new human protein kinase that is abundant in pancreatic islets of Langerhans, but is not expressed in most other tissues. This kinase, Apoptosis Signal Regulating Kinase Related Kinase (ASKRK), promotes cell death in pancreatic beta cells. Accordingly, the invention provides composition and methods of using such compositions to screen for inhibitors of ASKRK activity. Inhibitors of ASKRK can be used to modulate beta cell death and for the treatment of diabetes.

Thus, in one aspect, the invention provides an isolated nucleic acid encoding a polypeptide having at least 90%, often at least 95%, identity to SEQ ID NO:2. Typically, the nucleic acid encodes a polypeptide comprising SEQ ID NO:2. In one embodiment, the polypeptide is encoded by a nucleic acid comprising the sequence set forth in SEQ ID NO:1.

In another aspect, the invention provides an isolated nucleic acid encoding a polypeptide comprising an amino acid sequence having at least 90% identity to SEQ ID NO:4. Often, the nucleic acid encodes a polypeptide comprising the amino acid sequence set forth in SEQ ID NO:4. In one embodiment, the nucleic acid comprises the sequence set forth in SEQ ID NO:3.

In another aspect, the invention provides a method for identifying an agent for treating a diabetic or pre-diabetic individual, the method comprising the steps of: (i) contacting a candidate agent with a pancreatic or kidney cell that expresses a nucleic acid encoding a polypeptide having kinase activity that comprises at least 50 contiguous amino acids of SEQ ID NO:2; (ii) determining the activity of the polypeptide; and (iii) selecting an agent that inhibits the activity of the polypeptide, thereby identifying an agent for treating a diabetic or pre-diabetic individual. In some embodiments, the polypeptide comprises SEQ ID NO:2 or SEQ ID NO:4. Additionally, the polypeptide can be overexpressed relative to normal.

The cell can be, e.g., a pancreatic cell from a diabetic animal.

The some embodiments, the step of determining the activity of the polypeptide comprises determining the ability of the polypeptide to phosphorylate a substrate, determining the level of apoptosis, or determining the amount of protein present using an immunoassay.

In other embodiments, the agent is an siRNA or an antisense RNA.

In another aspect, the invention provides a method for identifying an agent for treating a diabetic or pre-diabetic individual, the method comprising the steps of: (i) contacting a candidate agent with a kidney or pancreatic cell that expresses a nucleic acid encoding a polypeptide having phosphorylating activity that comprises at least 50 contiguous amino acids of SEQ ID NO:2; (ii) determining the level of an RNA that encodes the polypeptide; and (ii) selecting an agent that inhibits the level of the RNA relative to normal, thereby identifying an agent for treating a diabetic or pre-diabetic individual. In some embodiments, the pancreatic cell may be from a diabetic animal. Often, the polypeptide comprises SEQ ID NO:2 or SEQ ID NO:4. The step of determining the level of an RNA can comprise an amplification reaction. In some embodiments, the agent is an siRNA or an antisense RNA.

In some embodiments, the method further comprises administering the agent to a pancreatic beta cell population; determining the level of apoptosis in the population; and selecting a candidate agent that decreases the level of apoptosis.

In another aspect, the invention provides a method for identifying an agent for treating a diabetic or pre-diabetic individual, the method comprising the steps of: (i) contacting a candidate agent with a polypeptide having phosphorylating activity that comprises at least 50 contiguous amino acids of SEQ ID NO:2; (ii) determining binding of the agent to the polypeptide; (iii) selecting an agent that binds to the polypeptide; (iv) administering the agent to population of pancreatic beta cells; (v) determining the level of apoptosis in the population relative to a control population of pancreatic beta cells; and (vi) selecting an agent that decreases apoptosis. Often, the polypeptide comprises SEQ ID NO:2 or SEQ ID NO:4. In one embodiment the step of determining binding of the agent to the polypeptide comprises determining the phosphorylating activity of the polypeptide.

In another aspect, the invention provides a method of improving insulin response in a diabetic animal or a pre-diabetic animal, e.g., a diabetic or pre-diabetic human, the method comprising administering to the animal a therapeutically effective amount of an agent identified by the methods described herein. In some embodiments, the agent may be administered to pancreatic tissue.

The invention also provides a method of introducing an expression cassette into a pancreatic cell, the method comprising, introducing into the cell an expression vector comprising a nucleic acid that, when expressed, inhibits the expression of a nucleic acid encoding a polypeptide having phosphorylating activity that comprises at least 50 contiguous amino acids of SEQ ID NO:2. Often, the polypeptide comprises SEQ ID NO:2. In some embodiments, the cell is introduced into a diabetic animal, typically a human.

BRIEF DESCRIPTION OF THE DRAWINGS

FIG. 2 shows an amino acid sequence alignment of mouse (partial coding; SEQ ID NO:5) and human (full coding; SEQ ID NO:6) ASKRK.

DETAILED DESCRIPTION OF THE INVENTION

Definitions

Figure 1:
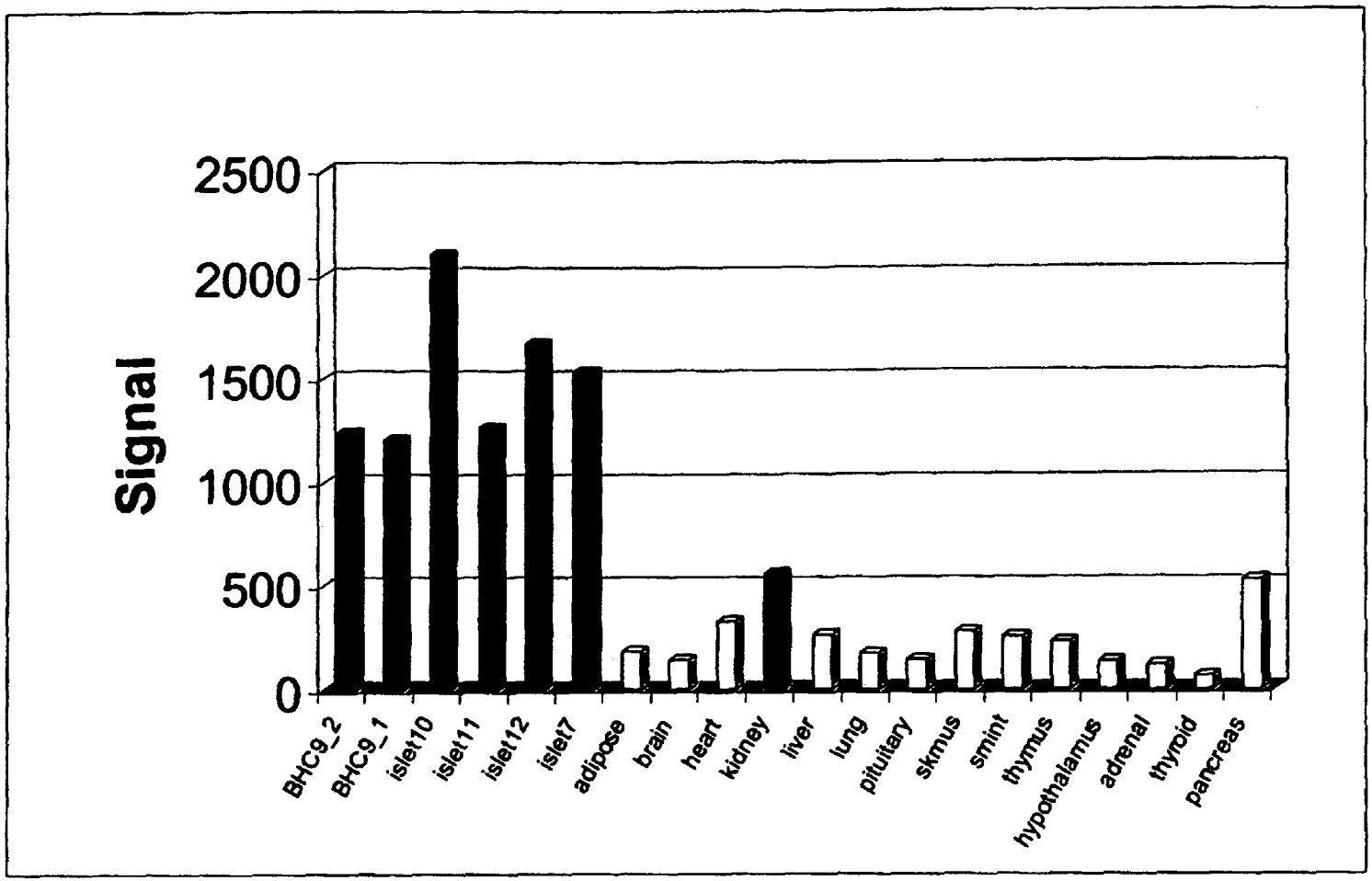
FIG. 1 shows the results of a custom microarray analysis. Custom Affymetrix™ oligonucleotide arrays were used to survey islet gene expression. Microarray probe set MBXMUS25681_at hybridizing to mouse ASKRK mRNA was called "Present" by the Affymetrix GeneChip™ analysis software in 4 independent mouse islet mRNA samples, 2 betaHC9 beta cell line samples and 1 kidney mRNA sample and absent in 13 other tissues examined.

An ASKRK nucleic acid or polypeptide refers to polymorphic variants, alleles, mutants, and interspecies homologs and ASKRK domains thereof that: (1) have an amino acid sequence that has greater than about 65% amino acid sequence identity, 70%, 75%, 80%, 85%, 90%, preferably 91%, 92%, 93%, 94%, 95%, 96%, 97%, 98% or 99% or greater amino acid sequence identity, preferably over a window of at least about 25, 50, 100, 200, 500, 1000, or more amino acids, to a sequence of SEQ ID NO:2 or SEQ ID NO4; (2) bind to antibodies raised against an immunogen comprising an amino acid sequence of SEQ ID NO:2 or SEQ ID NO:4 and conservatively modified variants thereof; (3) have at least 15 contiguous amino acids, more often, at least 20, 30, 40, 50 or 100 contiguous amino acids, of SEQ ID NO:2 or SEQ ID NO:4; (4) specifically hybridize (with a size of at least about 100, preferably at least about 500 or 1000 nucleotides) under stringent hybridization conditions to a sequence of SEQ ID NO:1 or SEQ ID NO:3 and conservatively modified variants thereof; (5) have a nucleic acid sequence that has greater than about 95%, preferably greater than about 96%, 97%, 98%, 99%, or higher nucleotide sequence identity, preferably over a region of at least about 50, 100, 200, 500, 1000, or more nucleotides, to SEQ ID NO:1 or SEQ ID NO:3; or (6) are amplified by primers that specifically hybridize under stringent conditions to SEQ ID NO:1 or SEQ ID NO:3. This term also refers to a domain of a ASKRK or a fusion protein comprising a domain of a ASKRK linked to a heterologous protein. An ASKRK polynucleotide or polypeptide sequence of the invention is typically from a mammal including, but not limited to, human, mouse, rat, hamster, cow, pig, horse, sheep, or any mammal. A "ASKRK polynucleotide" and a "ASKRK polypeptide," are both either naturally occurring or recombinant.

A "kinase domain" as used herein refers to the region of an ASKRK polypeptide that has catalytic activity, i.e., transfers phosphate from a high-energy phosphate donor molecule to the substrate.

"Activity" of an ASKRK polypeptide refers to structural, regulatory, or biochemical functions of the polypeptide in its native cell or tissue. Activity of ASKRK include both direct activities and indirect activities. An exemplary direct activity is catalytic activie, i.e., phosphorylation activity. Exemplary indirect activities are observed as a change in phenotype or response in a cell or tissue to a polypeptide's direct activity, e.g., apoptosis. Catalytic activity can be measured, e.g., by determining the amount of a substrate that is phosphorylated. Other activities, e.g., apoptoss, may also be assessed as a measure of ASKRK activity.

"Predisposition for diabetes" occurs in a person when the person is at high risk for developing diabetes. A number of risk factors are known to those of skill in the art and include: genetic factors (e.g., carrying alleles that result in a higher occurrence of diabetes than in the average population or having parents or siblings with diabetes); overweight (e.g., body mass index (BMI) greater or equal to 25 kg/m$^2$); habitual physical inactivity, race/ethnicity (e.g., African-American, Hispanic-American, Native Americans, Asian-Americans, Pacific Islanders); previously identified impaired fasting glucose or impaired glucose tolerance, hypertension (e.g., greater or equal to 140/90 mmHg in adults); HDL cholesterol less than or equal to 35 mg/dl; triglyceride levels greater or equal to 250 mg/dl; a history of gestational diabetes or delivery of a baby over nine pounds, and/or polycystic ovary syndrome. See, e.g., "Report of the Expert Committee on the Diagnosis and Classification of Diabetes Mellitus" and "Screening for Diabetes" Diabetes Care 25(1): S5–S24 (2002).

A "non-diabetic individual" (also referred to herein as a "lean" individual), when used to compare with a sample from a patient, refers to an adult with a fasting blood glucose level less than 110 mg/dl or a 2 hour PG reading of 140 mg/dl. "Fasting" refers to no caloric intake for at least 8 hours. A "2 hour PG" refers to the level of blood glucose after challenging a patient to a glucose load containing the equivalent of 75 g anhydrous glucose dissolved in water. The overall test is generally referred to as an oral glucose tolerance test (OGTT). See, e.g., Diabetes Care, Supplement 2002, American Diabetes Association: Clinical Practice Recommendations 2002. The level of a polypeptide in a non-diabetic individual can be a reading from a single individual, but is typically a statistically relevant average from a group of non-diabetic individuals. The level of a polypeptide in a nondiabetic individual can be represented by a value, for example in a computer program.

A "pre-diabetic individual," when used to compare with a sample from a patient, refers to an adult with a fasting blood glucose level greater than 110 mg/dl but less than 126 mg/dl or a 2 hour PG reading of greater than 140 mg/dl but less than 200 mg/dl. A "diabetic individual," when used to compare with a sample from a patient, refers to an adult with a fasting blood glucose level greater than 126 mg/dl or a 2 hour PG reading of greater than 200 mg/dl.

An "antagonist" or "inhibitor" refers to an agent that binds to, partially or totally blocks stimulation, decreases, prevents, delays activation, inactivates, desensitizes, or down regulates the activity or expression of ASKRK.

"Antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is compared of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H1$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially an Fab with part of the hinge region (see, Paul (Ed.) Fundamental Immunology, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies (e.g., single chain Fv).

The terms "peptidomimetic" and "mimetic" refers to a synthetic chemical compound that has substantially the same structural and functional characteristics of the antagonists or agonists of the invention. Peptide analogs are commonly used in the pharmaceutical industry as non-peptide drugs with properties analogous to those of the template peptide. These types of non-peptide compound are termed "peptide mimetics" or "peptidomimetics" (Fauchere, J. Adv. Drug Res. 15:29 (1986); Veber and Freidinger TINS p. 392 (1985); and Evans et al. J. Med. Chem. 30:1229 (1987), which are incorporated herein by reference). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as apolypeptide exemplified in this application, but have one or more peptide linkages optionally replaced by a linkage selected from the group consisting of, e.g., —CH2NH—, —CH2S—, —CH2—CH2—, —CH═CH— (cis and trans), —COCH2—, —CH(OH)CH2—, and —CH2SO—. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. For example, a mimetic composition is within the scope of the invention if it is capable of carrying out the binding or other activities of an agonist or antagonist of a polypeptide of the invention.

The term "gene" means the segment of DNA involved in producing a polypeptide chain; it includes regions preceding and following the coding region (leader and trailer) as well as intervening sequences (introns) between individual coding segments (exons).

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605–2608 (1985); and Cassol et al. (1992); Rossolini et al., Mol. Cell Probes 8:91–98 (1994)). The term nucleic acid is used interchangeably with gene, cDNA, and mRNA encoded by a gene.

"siRNA" refers to small interfering RNAs, that can cause post-transcriptional silencing of specific genes in cells, for example, mammalian cells (including human cells) and in the body, for example, mammalian bodies (including humans). The phenomenon of RNA interference is described and discussed in Bass, Nature 411: 428–29 (2001); Elbahir et al., Nature 411: 494–98 (2001); and Fire et al., Nature 391: 806–11 (1998); and WO 01/75164, where methods of making interfering RNA also are discussed. The siRNAs based upon the sequences and nucleic acids encoding the gene products disclosed herein typically have fewer than 100 base pairs and can be, e.g., about 30 bps or shorter, and can be made by approaches known in the art, including the use of complementary DNA strands or synthetic approaches. Exemplary siRNAs according to the invention can have up to 29 bps, 25 bps, 22 bps, 21 bps, 20 bps, 15 bps, 10 bps, 5 bps or any integer thereabout or therebetween. Tools for designing optimal inhibitory siRNAs include that available from DNAengine Inc. (Seattle, Wash.) and Ambion, Inc. (Austin, Tex.).

The term "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but which functions in a manner similar to a naturally occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine, Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" when the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, Proteins (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (e.g., a polypeptide of the invention), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences are substantially identical if two sequences have a specified percentage of amino acid residues or nucleotides that are the same (i.e., 60% identity, optionally 65%, 70%, 75%, 80%, 85%, 90%, or 95% identity over a specified region, or, when not specified, over the entire sequence), when compared and aligned for maximum correspondence over a comparison window, or designated region as measured using one of the following sequence comparison algorithms or by manual alignment and visual inspection. The invention provides polypeptides or polynucleotides that are substantially identical to the polynucleotides or polypeptides, respectively, exemplified herein in SEQ ID NOs:1 and 2. This definition also refers to the complement of a test sequence. Optionally, the identity exists over a region that is at least about 50 nucleotides in length, or more preferably over a region that is 100 to 500 or 1000 or more nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch (1970) J. Mol. Biol 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

Two examples of algorithms that are suitable for determining percent sequence identity and sequence similarity are the BLAST and BLAST 2.0 algorithms, which are described in Altschul et al. (1977) Nuc. Acids Res. 25:3389–3402, and Altschul et al. (1990) J. Mol. Biol. 215:403–410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands. For purposes of this patent application, sequence comparison are made using BLAST with default parameters.

The BLAST algorithm also performs a statistical analysis of the similarity between two sequences (see, e.g., Karlin and Altschul (1993) Proc. Natl. Acad. Sci. USA 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperatures (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.5 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, and 0.1% SDS at 55° C., 60° C., or 65° C. Such washes can be performed for 5, 15, 30, 60, 120, or more minutes.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such washes can be performed for 5, 15, 30, 60, 120, or more minutes. A positive hybridization is at least twice background. Those of ordinary skill will readily recognize that alternative hybridization and wash conditions can be utilized to provide conditions of similar stringency.

The phrase "a nucleic acid sequence encoding" refers to a nucleic acid which contains sequence information for a structural RNA such as rRNA, a tRNA, or the primary amino acid sequence of a specific protein or peptide, or a binding site for a trans-acting regulatory agent. This phrase specifically encompasses degenerate codons (i.e., different codons which encode a single amino acid) of the native sequence or sequences that may be introduced to conform with codon preference in a specific host cell.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under-expressed or not expressed at all.

The term "heterologous" when used with reference to portions of a nucleic acid indicates that the nucleic acid comprises two or more subsequences that are not found in the same relationship to each other in native. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The phrase "specifically (or selectively) binds to an antibody" or "specifically (or selectively) immunoreactive with", when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised against a protein having an amino acid sequence encoded by any of the polynucleotides of the invention can be selected to obtain antibodies specifically immunoreactive with that protein and not with other proteins, except for polymorphic variants. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See, Harlow and Lane Antibodies, A Laboratory Manual, Cold Spring Harbor Publications, NY (1988) for a description of immunoassay formats and conditions that can be used to determine specific immunoreactivity. Typically, a specific or selective reaction will be at least twice the background signal or noise and more typically more than 10 to 100 times background.

"Inhibitors" or "modulators" of expression or of activity are used to refer to inhibitory molecules that decrease ASKRK activity or expression. Such modulators are identified using in vitro and in vivo assays for expression or activity. Modulators encompass e.g., antagonists, and their homologs and mimetics. Inhibitors are agents that, e.g., inhibit expression of ASKRK or bind to, partially or totally block stimulation, decrease, prevent, delay activation, inactivate, desensitize, or down regulate the activity of ASKRK. Modulators include naturally occurring and synthetic ligands, antagonists, small chemical molecules and the like. Assays for inhibitors, e.g., applying putative modulator compounds to cells expressing ASKRK and then determining the functional effects on activity, as described above. Samples or assays comprising a ASKRK polypeptide that are treated with a potential modulator are compared to control samples without the modulator to examine the extent of effect. Control samples (untreated with modulators) are assigned a relative activity value of 100%. Inhibitors of a polypeptide of the invention is achieved when the polypeptide activity value relative to the control is about 80%, optionally 50% or 25, 10%, 5% or 1%.

Introduction

This invention is based on the discovery ASKRK plays a role in apoptosis of pancreatic beta cells. ASKRK is expressed predominantly in pancreatic beta cells. Thus, inhibitors of ASKRK expression or activity can be used to treat disorders relating to glucose metabolism, e.g., diabetes. Inhibition of ASKRK in diabetic or pre-diabetic individuals can, e.g., promote pancreatic beta cell viability. Modulation of the expression or activity of ASKRK can be beneficial in treating diabetic, pre-diabetic or obese insulin resistant, non-diabetic patients.

General Recombinant Nucleic Acid Methods

In numerous embodiments of the invention, nucleic acids encoding ASKRK polypeptides will be isolated and cloned using recombinant methods. Such embodiments are used, e.g., to isolate polynucleotides comprising a sequence that is identical or substantially identical to SEQ ID NO:1 for protein expression or for the generation of variants, derivatives, or other ASKRK sequences. Recombinant methodology is also used to generate expression cassettes, to monitor gene expression, for the isolation or detection of sequences in different species, for diagnostic purposes in a patient, e.g., to detect mutations in an ASKRK polynucleotide or polypeptide, or to detect expression levels of ASKRK nucleic acids or polypeptides. In some embodiments, the ASKRK sequences encoding the polypeptides are operably linked to a heterologous promoter. In one embodiment, the ASKRK nucleic acids are from any mammal, including, in particular, e.g., a human, a mouse, a rat, etc.

General Recombinant Nucleic Acid Methods

The recombinant methodology used in the invention is routine in the field of recombinant genetics. Basic texts disclosing the general methods include Sambrook & Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, Tetrahedron Letts. 22:1859–1862 (1981), using an automated synthesizer, as described in Van Devanter et. al., Nucleic Acids Res. 12:6159–6168 (1984). Purification of oligonucleotides is typically by either native acrylamide gel electrophoresis or by anion-exchange HPLC as described in Pearson & Reanier, J. Chrom. 255:137–149 (1983).

The sequences of the cloned genes and synthetic oligonucleotides can be verified after cloning using, e.g., the chain termination method for sequencing double-stranded templates of Wallace et al., Gene 16:21–26 (1981).

Cloning Methods for the Isolation of Nucleotide Sequences Encoding Desired Proteins In general, nucleic acids encoding the ASKRK proteins are cloned from cDNA or genomic libraries. The particular sequences can be identified, e.g., by hybridizing with a probe, the sequence of which can be derived from the sequences disclosed herein, which provide a reference for PCR primers and defines suitable regions for isolating probes specific for ASKRK polynucleotides. Alternatively, where the sequence is cloned into an expression library, the expressed recombinant protein can be detected immunologically with antisera or purified antibodies made against ASKRK polypeptides, e.g., SEQ ID NO:2. Methods of constructing cDNA and genomic libraries are well known in the art (see, e.g., Sambrook & Russell, supra; and Ausubel et al., supra).

An alternative method of isolating ASKRK nucleic acids and their homologs combines the use of synthetic oligonucleotide primers and amplification of an RNA or DNA template (see, e.g., U.S. Pat. Nos. 4,683,195 and 4,683,202; PCR Protocols: A Guide to Methods and Applications (Innis et al., eds, 1990)). Methods such as polymerase chain reaction (PCR) and ligase chain reaction (LCR) can be used to amplify ASKRK nucleic acid sequences directly from mRNA, from cDNA, from genomic libraries or cDNA libraries. Degenerate oligonucleotides can be designed to amplify ASKRK homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of ASKRK-encoding mRNA in physiological samples, for nucleic acid sequencing, or for other purposes. Genes amplified by the PCR reaction can be purified from agarose gels and cloned into an appropriate vector.

Synthetic oligonucleotides can be used to construct recombinant ASKRK genes for use as probes or for expression of protein. This method is performed using a series of overlapping oligonucleotides usually 40–120 bp in length, representing both the sense and nonsense strands of the gene. These DNA fragments are then annealed, ligated and cloned. Alternatively, amplification techniques can be used with precise primers to amplify a specific subsequence of the ASKRK nucleic acid. The specific subsequence is then ligated into an expression vector.

The nucleic acid encoding ASKRK is typically cloned into intermediate vectors before transformation into prokaryotic or eukaryotic cells for replication and/or expression. These intermediate vectors are typically prokaryote vectors, e.g., plasmids, or shuttle vectors.

Optionally, nucleic acids encoding chimeric proteins comprising ASKRK or domains thereof can be made according to standard techniques. For example, a domain comprising the active site can be covalently linked to a heterologous protein.

To obtain high level expression of an ASKRK nucleic acid, such as a cDNAs encoding SEQ ID NO:2, one typically subclones a nucleic acid sequence encoding the protein of into an expression vector that contains a promoter, typically a heterologous promoter, to direct transcription, a transcription/translation terminator, and a ribosome binding site for translational initiation. Suitable promoters are well known in the art and described, e.g., in Sambrook & Russell and Ausubel et al. Bacterial expression systems for expressing the protein are available in, e.g., E. coli, Bacillus sp., and Salmonella (Palva et al., Gene 22:229–235 (1983); Mosbach et al., Nature 302:543–545 (1983). Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc. Kits for such expression systems are commercially available.

Eukaryotic expression systems for mammalian cells, yeast, and insect cells are also well known in the art and commercially available. For example, exemplary vectors include SV40-based vectors, papilloma virus vectors, baculovirus vectors, and other vectors allowing expression of proteins under the direction of eukaryotic promoters, e.g., SV40 early promoter, SV40 later promoter, metallothionein promoter, murine mammary tumor virus promoter, Rous sarcoma virus promoter, or other promoters shown effective for expression in eukaryotic cells. In one embodiment, the eukaryotic expression vector is a viral vector, e.g., an adenoviral vector, an adeno-associated vector, or a retroviral vector.

Any of many well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Russell & Sambrook, supra). It is only necessary that the particular genetic engineering procedure used be capable of successfully introducing at least one gene into the host cell capable of expressing ASKRK.

After the expression vector is introduced into the cells, the transfected cells are cultured under conditions favoring expression of the protein, which is recovered from the culture using standard techniques identified below.

Transgenic animals, including knockout transgenic animals, that include additional copies of ASKRK and/or altered or mutated ASKRK transgenes can also be generated. A "transgenic animal" refers to any animal (e.g., mouse, rat, pig, bird, or an amphibian), preferably a non-human mammal, in which one or more cells contain heterologous nucleic acid introduced using transgenic techniques well known in the art. The nucleic acid is introduced into the cell, directly or indirectly, by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA.

In other embodiments, transgenic animals are produced in which expression of ASKRK is silenced. Gene knockout by homologous recombination is a method that is commonly used to generate transgenic animals. Transgenic mice can be derived using methodology known to those of skill in the art, see, e.g., Hogan et al., Manipulating the Mouse Embryo: A Laboratory Manual, (1988); Teratocarcinomas and Embryonic Stem Cells: A Practical Approach, Robertson, ed., (1987); and Capecchi et al., Science 244:1288 (1989).

Purification of ASKRK Proteins

Either naturally occurring or recombinant ASKRK polypeptides can be purified for use in functional assays. Naturally occurring ASKRK polypeptides of the invention can be purified from any source (e.g., tissues of an organism expressing an ortholog). Recombinant polypeptides can be purified from any suitable expression system. ASKRK polypeptides are purified to substantial purity by standard techniques, including selective precipitation with such substances as ammonium sulfate; column chromatography, immunopurification methods, and others (see, e.g., Scopes, Protein Purification: Principles and Practice (1982); U.S. Pat. No. 4,673,641; Ausubel et al., supra; and Sambrook & Russell., supra).

A number of procedures can be employed when recombinant polypeptides are being purified. For example, proteins having established molecular adhesion properties can be reversibly fused to a polypeptide of the invention. With the appropriate ligand, either protein can be selectively adsorbed to a purification column and then freed from the column in a relatively pure form. The fused protein may be then removed by enzymatic activity. Finally polypeptides can be purified using immunoaffinity columns.

When recombinant proteins are expressed by the transformed bacteria in large amounts, typically after promoter induction, although expression can be constitutive, the proteins may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells typically, but not limited to, by incubation in a buffer of about 100–150 μg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel et al. and Sambrook et al., both supra, and will be apparent to those of skill in the art.

Alternatively, it is possible to purify proteins from bacteria periplasm. Where the protein is exported into the periplasm of the bacteria, the periplasmic fraction of the bacteria can be isolated by cold osmotic shock in addition to other methods known to those of skill in the art (see, Ausubel et al., supra).

Proteins can also be purified from eukaryotic gene expression systems as described in, e.g., Fernandez and Hoeffler, Gene Expression Systems (1999). In some embodiments, baculovirus expression systems are used to isolate proteins of the invention. Recombinant baculoviruses are generally generated by replacing the polyhedrin coding sequence of a baculovirus with a gene to be expressed (e.g., encoding a polypeptide of the invention). Viruses lacking the polyhedrin gene have a unique plaque morphology making them easy to recognize. In some embodiments, a recombinant baculovirus is generated by first cloning a polynucleotide of interest into a transfer vector (e.g., a pUC based vector) such that the polynucleotide is operably linked to a polyhedrin promoter. The transfer vector is transfected with wildtype DNA into an insect cell (e.g., Sf9, Sf21 or BT1-TN-5B1-4 cells), resulting in homologous recombination and replacement of the polyhedrin gene in the wildtype viral DNA with the polynucleotide of interest. Virus can then be generated and plaque purified. Protein expression results upon viral infection of insect cells. Expressed proteins can be harvested from cell supernatant if secreted, or from cell lysates if intracellular. See, e.g., Ausubel et al. and Fernandez and Hoeffler, supra.

Proteins are purified using standard techniques including, for example, an initial salt fractionation. Other methods that rely on solubility of proteins, such as cold ethanol precipitation, are well known to those of skill in the art and can be used to fractionate complex protein mixtures.

Proteins may also be separated based on a calculated molecular weight using techniques such as ultrafiltration and size separation on a column. The proteins of interest can also be separated from other proteins on the basis of their size, net surface charge, hydrophobicity and affinity for ligands. In addition, antibodies raised against proteins can be conjugated to column matrices and the proteins immunopurified. All of these methods are well known in the art.

Immunoaffinity chromatography using antibodies raised to a variety of affinity tags such as hemagglutinin (HA), FLAG, Xpress, Myc, hexahistidine (His) (SEQ ID NO:7), glutathione S transferase (GST) and the like can be used to purify polypeptides. The His tag will also act as a chelating agent for certain metals (e.g., Ni) and thus the metals can also be used for purify His-containing polypeptides. After purification, the tag is optionally removed by specific proteolytic cleavage.

Detection of ASKRK Polynucleotides

Those of skill in the art will recognize that detection of expression of ASKRK polynucleotides and polypeptides has many uses. For example, as discussed herein, detection of levels of polynucleotides and polypeptides of the invention in a patient can be useful for diagnosing diabetes or a predisposition for at least some of the pathological effects of diabetes. Moreover, detection of gene expression is useful to identity modulators, e.g., inhibitors, of expression of ASKRK polynucleotides and polypeptides.

Gene expression can be analyzed by techniques known in the art, e.g., reverse transcription and amplification of mRNA, isolation of total RNA or poly A+ RNA, northern blotting, dot blotting, in situ hybridization, RNase protection, probing DNA microchip arrays, and the like, as further described below.

A variety of methods of specific DNA and RNA measurement that use nucleic acid hybridization techniques are known to those of skill in the art (see, Sambrook, supra). Some methods involve an electrophoretic separation (e.g., Southern blot for detecting DNA, and Northern blot for detecting RNA), but measurement of DNA and RNA can also be carried out in the absence of electrophoretic separation (e.g., by dot blot). Southern blot of genomic DNA (e.g., from a human) can be used for screening for restriction fragment length polymorphism (RFLP) to detect the presence of a genetic disorder affecting a polypeptide of the invention.

The selection of a nucleic acid hybridization format is not critical. A variety of nucleic acid hybridization formats are known to those skilled in the art. For example, common formats include sandwich assays and competition or displacement assays. Hybridization techniques are generally described in Hames and Higgins Nucleic Acid Hybridization, a Practical Approach, IRL Press (1985); Gall and Pardue, Proc. Natl. Acad. Sci. U.S.A., 63:378–383 (1969); and John et al., Nature, 223:582–587 (1969).

Detection of a hybridization complex may require the binding of a signal-generating complex to a duplex of target and probe polynucleotides or nucleic acids. Typically, such binding occurs through ligand and anti-ligand interactions as between a ligand-conjugated probe and an anti-ligand conjugated with a signal. The binding of the signal generation complex is also readily amenable to accelerations by exposure to ultrasonic energy.

The label may also allow indirect detection of the hybridization complex. For example, where the label is a hapten or antigen, the sample can be detected by using antibodies. In these systems, a signal is generated by attaching fluorescent or enzyme molecules to the antibodies or in some cases, by attachment to a radioactive label (see, e.g., Tijssen, "Practice and Theory of Enzyme Immunoassays," Laboratory Techniques in Biochemistry and Molecular Biology, Burdon and van Knippenberg Eds., Elsevier (1985), pp. 9–20).

The probes are typically labeled either directly, as with isotopes, chromophores, lumiphores, chromogens, or indirectly, such as with biotin, to which a streptavidin complex may later bind. Thus, the detectable labels used in the assays of the present invention can be primary labels (where the label comprises an element that is detected directly or that produces a directly detectable element) or secondary labels (where the detected label binds to a primary label, e.g., as is common in immunological labeling). Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^{3}H$, $^{125}I$, $^{35}S$, $^{14}C$, or $^{32}P$-labeled probes or the like.

Other labels include, e.g., ligands that bind to labeled antibodies, fluorophores, chemiluminescent agents, enzymes, and antibodies that can serve as specific binding pair members for a labeled ligand. An introduction to labels, labeling procedures and detection of labels is found in Polak and Van Noorden Introduction to Immunocytochemistry, 2nd ed., Springer Verlag, NY (1997); and in Haugland Handbook of Fluorescent Probes and Research Chemicals, a combined handbook and catalogue Published by Molecular Probes, Inc. (1996).

In general, a detector that monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill in the art. Commonly, an optical image of a substrate comprising bound labeling moieties is digitized for subsequent computer analysis.

The amount of, for example, an ASKRK RNA is measured by quantifying the amount of label fixed to the solid support by binding of the detection reagent. Typically, the presence of a modulator during incubation will increase or decrease the amount of label fixed to the solid support relative to a control incubation that does not comprise the modulator, or as compared to a baseline established for a particular reaction type. Means of detecting and quantifying labels are well known to those of skill in the art.

In some embodiments, the target nucleic acid or the probe is immobilized on a solid support. Solid supports suitable for use in the assays of the invention are known to those of skill in the art. As used herein, a solid support is a matrix of material in a substantially fixed arrangement.

A variety of automated solid-phase assay techniques are also appropriate. For instance, very large scale immobilized polymer arrays (VLSIPS™), i.e., Gene Chips or microarrays, available from Affymetrix, Inc. in Santa Clara, Calif. can be used to detect changes in expression levels of a plurality of genes involved in the same regulatory pathways simultaneously. See, Tijssen, supra., Fodor et al. (1991) Science, 251: 767–777; Sheldon et al. (1993) Clinical Chemistry 39(4): 718–719, and Kozal et al. (1996) Nature Medicine 2(7): 753–759. Similarly, spotted cDNA arrays (arrays of cDNA sequences bound to nylon, glass or another solid support) can also be used to monitor expression of a plurality of genes.

Typically, the array elements are organized in an ordered fashion so that each element is present at a specified location on the substrate. Because the array elements are at specified locations on the substrate, the hybridization patterns and intensities (which together create a unique expression profile) can be interpreted in terms of expression levels of particular genes and can be correlated with a particular disease or condition or treatment. See, e.g., Schena et al., Science 270: 467–470 (1995)) and (Lockhart et al., Nature Biotech. 14: 1675–1680 (1996)).

Hybridization specificity can be evaluated by comparing the hybridization of specificity-control polynucleotide sequences to specificity-control polynucleotide probes that are added to a sample in a known amount. The specificity-control target polynucleotides may have one or more sequence mismatches compared with the corresponding polynucleotide sequences. In this manner, whether only complementary target polynucleotides are hybridizing to the polynucleotide sequences or whether mismatched hybrid duplexes are forming is determined.

Hybridization reactions can be performed in absolute or differential hybridization formats. In the absolute hybridization format, polynucleotide probes from one sample are hybridized to the sequences in a microarray format and signals detected after hybridization complex formation correlate to polynucleotide probe levels in a sample. In the differential hybridization format, the differential expression of a set of genes in two biological samples is analyzed. For differential hybridization, polynucleotide probes from both biological samples are prepared and labeled with different labeling moieties. A mixture of the two labeled polynucleotide probes is added to a microarray. The microarray is then examined under conditions in which the emissions from the two different labels are individually detectable. Sequences in the microarray that are hybridized to substantially equal numbers of polynucleotide probes derived from both biological samples give a distinct combined fluorescence (Shalon et al. PCT publication WO95/35505). In some embodiments, the labels are fluorescent labels with distinguishable emission spectra, such as Cy3 and Cy5 fluorophores.

After hybridization, the microarray is washed to remove nonhybridized nucleic acids and complex formation between the hybridizable array elements and the polynucleotide probes is detected. Methods for detecting complex formation are well known to those skilled in the art. In some embodiments, the polynucleotide probes are labeled with a fluorescent label and measurement of levels and patterns of fluorescence indicative of complex formation is accomplished by fluorescence microscopy, such as confocal fluorescence microscopy.

In a differential hybridization experiment, polynucleotide probes from two or more different biological samples are labeled with two or more different fluorescent labels with different emission wavelengths. Fluorescent signals are detected separately with different photomultipliers set to detect specific wavelengths. The relative abundances/expression levels of the polynucleotide probes in two or more samples are obtained.

Typically, microarray fluorescence intensities can be normalized to take into account variations in hybridization intensities when more than one microarray is used under similar test conditions. In some embodiments, individual polynucleotide probe/target complex hybridization intensities are normalized using the intensities derived from internal normalization controls contained on each microarray.

Detection of nucleic acids can also be accomplished, for example, by using a labeled detection moiety that binds specifically to duplex nucleic acids (e.g., an antibody that is specific for RNA-DNA duplexes). One example uses an antibody that recognizes DNA-RNA heteroduplexes in which the antibody is linked to an enzyme (typically by recombinant or covalent chemical bonding). The antibody is detected when the enzyme reacts with its substrate, producing a detectable product. Coutlee et al. (1989) Analytical Biochemistry 181:153–162; Bogulavski (1986) et al. J. Immunol. Methods 89:123–130; Prooijen-Knegt (1982) Exp. Cell Res. 141:397–407; Rudkin (1976) Nature 265:472–473, Stollar (1970) PNAS 65:993–1000; Ballard (1982) Mol. Immunol. 19:793–799; Pisetsky and Caster (1982) Mol. Immunol. 19:645–650; Viscidi et al. (1988) J. Clin. Microbiol. 41:199–209; and Kiney et al. (1989) J. Clin. Microbiol. 27:6–12 describe antibodies to RNA duplexes, including homo and heteroduplexes. Kits comprising antibodies specific for DNA:RNA hybrids are available, e.g., from Digene Diagnostics, Inc. (Beltsville, Md.).

In addition to available antibodies, one of skill in the art can easily make antibodies specific for nucleic acid duplexes using existing techniques, or modify those antibodies that are commercially or publicly available. In addition to the art referenced above, general methods for producing polyclonal and monoclonal antibodies are known to those of skill in the art (see, e.g., Paul (ed) Fundamental Immunology, Third Edition Raven Press, Ltd., NY (1993); Colligan Current Protocols in Immunology Wiley/Greene, NY (1991); Harlow and Lane Antibodies: A Laboratory Manual Cold Spring Harbor Press, NY (1989); Stites et al. (eds.) Basic and Clinical Immunology (4th ed.) Lange Medical Publications, Los Altos, Calif., and references cited therein; Goding Monoclonal Antibodies: Principles and Practice (2d ed.) Academic Press, New York, N.Y., (1986); and Kohler and Milstein Nature 256: 495–497 (1975)). Other suitable techniques for antibody preparation include selection of libraries of recombinant antibodies in phage or similar vectors (see, Huse et al. Science 246:1275–1281 (1989); and Ward et al. Nature 341:544–546 (1989)). Specific monoclonal and polyclonal antibodies and antisera will usually bind with a $K_D$ of at least about 0.1 μM, preferably at least about 0.01 μM or better, and most typically and preferably, 0.001 μM or better.

The ASKRK nucleic acids used in this invention can be either positive or negative probes. Positive probes bind to their targets and the presence of duplex formation is evidence of the presence of the target. Negative probes fail to bind to the suspect target and the absence of duplex formation is evidence of the presence of the target. For example, the use of a wild type specific nucleic acid probe or PCR primers may serve as a negative probe in an assay sample where only the nucleotide sequence of interest is present.

The sensitivity of the hybridization assays may be enhanced through use of a nucleic acid amplification system that multiplies the target nucleic acid being detected. Examples of such systems including the polymerase chain reaction (PCR) system and the ligase chain reaction (LCR) system. Other methods recently described in the art are the nucleic acid sequence based amplification (NASBA, Cangene, Mississauga, Ontario) and Q Beta Replicase systems. These systems can be used to directly identify mutants where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation. It is understood that various detection probes, including Taqman and molecular beacon probes can be used to monitor amplification reaction products, e.g., in real time.

An alternative means for determining the level of expression of the nucleic acids of the present invention is in situ hybridization. In situ hybridization assays are well known and are generally described in Angerer et al. Methods Enzymol. 152:649–660 (1987). In an in situ hybridization assay, cells, preferentially human cells from the cerebellum or the hippocampus, are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

Single nucleotide polymorphism (SNP) analysis is also useful for detecting differences between ASKRK alleles. SNPs linked to genes encoding polypeptides of the invention are useful, for instance, for diagnosis of diabetes or a predisposition to diabetes whose occurrence is linked to the gene sequences of the invention. For example, if an individual carries at least one SNP linked to a disease-associated allele of the gene sequences of the invention, the individual is likely predisposed for one or more of those diseases. If the individual is homozygous for a disease-linked SNP, the individual is particularly predisposed for occurrence of that disease (e.g., diabetes). In some embodiments, the SNP associated with the gene sequences of the invention is located within 300,000; 200,000; 100,000; 75,000; 50,000; or 10,000 base pairs from the gene sequence.

Various real-time PCR methods including, e.g., Taqman or molecular beacon-based assays (e.g., U.S. Pat. Nos. 5,210,015; 5,487,972; Tyagi et al., Nature Biotechnology 14:303 (1996); and PCT WO 95/13399 are useful to monitor for the presence of absence of a SNP. Additional SNP detection methods include, e.g., DNA sequencing, sequencing by hybridization, dot blotting, oligonucleotide array (DNA Chip) hybridization analysis, or are described in, e.g., U.S.

Pat. No. 6,177,249; Landegren et al., Genome Research, 8:769–776 (1998); Botstein et al., Am J Human Genetics 32:314–331 (1980); Meyers et al., Methods in Enzymology 155:501–527 (1987); Keen et al., Trends in Genetics 7:5 (1991); Myers et al., Science 230:1242–1246 (1985); and Kwok et al., Genomics 23:138–144 (1994).

Immunodetection of ASKRK Polypeptides

In addition to the detection of ASKRK polynucleotides and gene expression using nucleic acid hybridization technology, one can also use immunoassays to detect ASKRK polypeptides. Immunoassays can be used to qualitatively or quantitatively analyze polypeptides of the invention. A general overview of the applicable technology can be found, e.g., in Harlow & Lane, Antibodies: A Laboratory Manual (1988) and Harlow & Lane, Using Antibodies (1999).

Antibodies to ASKRK Proteins or Other Immunogens

Methods for producing polyclonal and monoclonal antibodies that react specifically with an ASKRK protein or other immunogen are known to those of skill in the art (see, e.g., Coligan, supra; and Harlow and Lane, supra; Stites et al., supra and references cited therein; Goding, supra; and Kohler and Milstein Nature, 256:495–497 (1975)). Such techniques include antibody preparation by selection of antibodies from libraries of recombinant antibodies in phage or similar vectors (see, Huse et al., supra; and Ward et al., supra). For example, in order to produce antisera for use in an immunoassay, the protein of interest or an antigenic fragment thereof, is isolated as described herein. For example, a recombinant ASKRK protein is produced in a transformed cell line. An inbred strain of mice or rabbits is immunized with the protein using a standard adjuvant, such as Freund's adjuvant, and a standard immunization protocol. Alternatively, a synthetic peptide derived from the ASKRK sequences disclosed herein is conjugated to a carrier protein and used as an immunogen.

Polyclonal sera are collected and titered against the immunogen in an immunoassay, for example, a solid phase immunoassay with the immunogen immobilized on a solid support. Polyclonal antisera with a titer of $10^4$ or greater are selected and tested for their crossreactivity against proteins other than the polypeptides of the invention or even other homologous proteins from other organisms, using a competitive binding immunoassay. Specific monoclonal and polyclonal antibodies and antisera will usually bind with a $K_D$ of at least about 0.1 mM, more usually at least about 1 μM, preferably at least about 0.1 μM or better, and most preferably, 0.01 μM or better.

Recombinant protein is the preferred immunogen for the production of monoclonal or polyclonal antibodies. Naturally occurring protein may also be used either in pure or impure form. Synthetic peptides made using the protein sequences described herein may also be used as an immunogen for the production of antibodies to the protein. Recombinant protein can be expressed in eukaryotic or prokaryotic cells and purified as generally described supra. The product is then injected into an animal capable of producing antibodies. Either monoclonal or polyclonal antibodies may be generated for subsequent use to immunoassays to measure the protein.

Methods of production of polyclonal antibodies are known to those of skill in the art. In brief, an immunogen, preferably a purified protein, is mixed with an adjuvant and animals are immunized. The animal's immune response to the immunogen preparation is monitored by taking test bleeds and determining the titer of reactivity to polypeptides of the invention. When appropriately high titers of antibody to the immunogen are obtained, blood is collected from the animal and antisera are prepared. Further fractionation of the antisera to enrich for antibodies reactive to the protein can be done if desired (See, Harlow and Lane, supra).

Monoclonal antibodies may be obtained using various techniques familiar to those of skill in the art. Typically, spleen cells from an animal immunized with a desired antigen are immortalized, commonly by fusion with a myeloma cell (see, Kohler and Milstein, Eur. J. Immunol. 6:511–519 (1976)). Alternative methods of immortalization include, e.g., transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences that encode a monoclonal antibody or a binding fragment thereof by screening a DNA library from human B cells according to the general protocol outlined by Huse et al., supra.

Once target immunogen-specific antibodies are available, the immunogen can be measured by a variety of immunoassay methods with qualitative and quantitative results available to the clinician. For a review of immunological and immunoassay procedures in general see, Stites, supra. Moreover, the immunoassays of the present invention can be performed in any of several configurations, which are reviewed extensively in Maggio Enzyme Immunoassay, CRC Press, Boca Raton, Fla. (1980); Tijssen, supra; and Harlow and Lane, supra.

Immunoassays to measure target proteins in a human sample may use a polyclonal antiserum that was raised to full-length polypeptides of the invention or a fragment thereof. This antiserum is selected to have low cross-reactivity against other proteins and any such cross-reactivity is removed by immunoabsorption prior to use in the immunoassay.

Immunoassays

In some embodiments, a protein of interest is detected and/or quantified using any of a number of well-known immunological binding assays (see, e.g., U.S. Pat. Nos. 4,366,241; 4,376,110; 4,517,288; and 4,837,168). For a review of the general immunoassays, see also Asai Methods in Cell Biology Volume 37: Antibodies in Cell Biology, Academic Press, Inc. NY (1993); Stites, supra. Immunological binding assays (or immunoassays) typically utilize a "capture agent" to specifically bind to and often immobilize the analyte (e.g., full-length polypeptides of the present invention, or antigenic subsequences thereof). The capture agent is a moiety that specifically binds to the analyte. The antibody may be produced by any of a number of means well known to those of skill in the art and as described above.

Immunoassays also often utilize a labeling agent to bind specifically to and label the binding complex formed by the capture agent and the analyte. The labeling agent may itself be one of the moieties comprising the antibody/analyte complex. Alternatively, the labeling agent may be a third moiety, such as another antibody, that specifically binds to the antibody/protein complex.

In a preferred embodiment, the labeling agent is a second antibody bearing a label. Alternatively, the second antibody may lack a label, but it may, in turn, be bound by a labeled third antibody specific to antibodies of the species from which the second antibody is derived. The second antibody can be modified with a detectable moiety, such as biotin, to which a third labeled molecule can specifically bind, such as enzyme-labeled streptavidin.

Other proteins capable of specifically binding immunoglobulin constant regions, such as protein A or protein G, can also be used as the label agents. These proteins are normal constituents of the cell walls of streptococcal bacteria. They exhibit a strong non-immunogenic reactivity with immunoglobulin constant regions from a variety of species (see, generally, Kronval, et al., J. Immunol., 111:1401–1406 (1973)); and Akerstrom, et al. J. Immunol., 135:2589–2542 (1985)).

Throughout the assays, incubation and/or washing steps may be required after each combination of reagents. Incubation steps can vary from about 5 seconds to several hours, preferably from about 5 minutes to about 24 hours. The incubation time will depend upon the assay format, analyte, volume of solution, concentrations, and the like. Usually, the assays will be carried out at ambient temperature, although they can be conducted over a range of temperatures, such as 10° C. to 40° C.

Immunoassays for detecting ASKRK proteins or other analytes of interest from tissue samples may be either competitive or noncompetitive. Noncompetitive immunoassays are assays in which the amount of captured protein or analyte is directly measured. In one preferred "sandwich" assay, for example, the capture agent (e.g., antibodies specific for the polypeptides of the invention) can be bound directly to a solid substrate where it is immobilized. These immobilized antibodies then capture the polypeptide present in the test sample. The polypeptide of the invention thus immobilized is then bound by a labeling agent, such as a second labelled antibody specified for the polypeptide. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

In some embodiments, western blot (immunoblot) analysis is used to detect and quantify the presence of a polypeptide of the invention in the sample. The technique generally comprises separating sample proteins by gel electrophoresis, transferring the separated proteins to a suitable solid support and incubating the sample with the antibodies that specifically bind the protein of interest. These antibodies may be directly labeled or alternatively may be subsequently detected using labeled antibodies (e.g., labeled sheep anti-mouse antibodies) that specifically bind to the antibodies against the protein of interest.

Other assay formats include liposome immunoassays (LIA), which use liposomes designed to bind specific molecules (e.g., antibodies) and release encapsulated reagents or markers. The released chemicals are then detected according to standard techniques (see, Monroe et al. (1986) Amer. Clin. Prod. Rev. 5:34–41).

In competitive assays, the amount of protein or analyte present in the sample is measured indirectly by measuring the amount of an added (exogenous) protein or analyte displaced (or competed away) from a specific capture agent (e.g., antibodies specific for a polypeptide of the invention) by the protein or analytic present in the sample. The amount of immunogen bound to the antibody is inversely proportional to the concentration of immunogen present in the sample. In a particularly preferred embodiment, the antibody is immobilized on a solid substrate. The amount of analyte may be detected by providing a labeled analyte molecule. It is understood that labels can include, e.g., radioactive labels as well as peptide or other tags that can be recognized by detection reagents such as antibodies.

Immunoassays in the competitive binding format can be used for cross-reactivity determinations. For example, the protein encoded by the sequences described herein can be immobilized on a solid support. Proteins are added to the assay and compete with the binding of the antisera to the immobilized antigen. The ability of the above proteins to compete with the binding of the antisera to the immobilized protein is compared to that of the protein encoded by any of the sequences described herein. The percent cross-reactivity for the above proteins is calculated, using standard calculations. Those antisera with less than 10% cross-reactivity with each of the proteins listed above are selected and pooled. The cross-reacting antibodies are optionally removed from the pooled antisera by immunoabsorption with the considered proteins, e.g., distantly related homologs.

The immunoabsorbed and pooled antisera are then used in a competitive binding immunoassay as described above to compare a second protein, thought to be perhaps a protein of the present invention, to the immunogen protein. In order to make this comparison, the two proteins are each assayed at a wide range of concentrations and the amount of each protein required to inhibit 50% of the binding of the antisera to the immobilized protein is determined. If the amount of the second protein required is less than 10 times the amount of the protein partially encoded by a sequence herein that is required, then the second protein is said to specifically bind to an antibody generated to an immunogen consisting of the target protein.

Labels

The particular label or detectable group used in various assays is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most labels useful in such methods can be applied to the present invention. Thus, a label is any composition detectable by spectroscopic, photochemical, biochemical, immunochemical, electrical, optical or chemical means. Useful labels in the present invention include magnetic beads (e.g., Dynabeads™), fluorescent dyes (e.g., fluorescein isothiocyanate, Texas red, rhodamine, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

The label may be coupled directly or indirectly to the desired component of the assay according to methods well known in the art. As indicated above, a wide variety of labels may be used, with the choice of label depending on the sensitivity required, the ease of conjugation with the compound, stability requirements, available instrumentation, and disposal provisions.

Non-radioactive labels are often attached by indirect means. The molecules can also be conjugated directly to signal generating compounds, e.g., by conjugation with an enzyme or fluorescent compound. A variety of enzymes and fluorescent compounds can be used with the methods of the present invention and are well-known to those of skill in the art (for a review of various labeling or signal producing systems which may be used, see, e.g., U.S. Pat. No. 4,391,904).

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple calorimetric labels may be detected directly by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need to be labeled and the presence of the target antibody is detected by simple visual inspection.

Identification of Modulators of ASKRK

Inhibitors of ASKRK, i.e., inhibitors of ASKRK activity or expression, are useful for treating a number of human diseases relating to glucose metabolism, including diabetes. For example, administration of inhibitors can be used to treat diabetic patients or prediabetic individuals to prevent progression, and therefore symptoms, associated with diabetes.

A. Agents that Modulate ASKRK Polypeptides

The agents tested as modulators of polypeptides of the invention can be any small chemical compound, or a biological entity, such as a protein, sugar, nucleic acid or lipid. Typically, test compounds will be small chemical molecules and peptides. Essentially any chemical compound can be used as a potential modulator or ligand in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). Modulators also include agents designed to reduce the level of mRNA encoding an ASKRK polypeptide (e.g., antisense molecules, ribozymes, DNAzymes, small inhibitory RNAs and the like) or the level of translation from an mRNA (e.g., translation blockers such as an antisense molecules that are complementary to translation start or other sequences on an mRNA molecule). Modulators can also be variants or mutant proteins of an ASKRK polypeptide. It will be appreciated that there are many suppliers of chemical compounds, including Sigma (St. Louis, Mo.), Aldrich (St. Louis, Mo.). Sigma-Aldrich (St. Louis, Mo.), Fluka Chemika-Biochemica-Analytika (Buchs, Switzerland) and the like.

In some embodiments, high throughput screening methods involve providing a combinatorial chemical or peptide library containing a large number of potential therapeutic compounds (potential modulator compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res. 37:487–493 (1991) and Houghton et al., Nature 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bioolligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909–6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217–9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., Nature Biotechnology, 14(3):309–314 (1996) and PCT/US96/10287), carbohydrate libraries (see, e.g., Liang et al., Science, 274: 1520–1522 (1996) and U.S. Pat. No. 5,593,853), small organic molecule libraries (see, e.g., benzodiazepines, Baum C&EN, Jan. 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem. Tech. Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

B. Methods of Screening for Modulators of the Polypeptides of the Invention

A number of different screening protocols can be utilized to identify agents that modulate the level of expression or activity of a polynucleotide of a polypeptide of the invention in cells, particularly mammalian cells, and especially human cells. In general terms, the screening methods involve screening a plurality of agents to identify an agent that modulates the activity of a polypeptide of the invention by, e.g., binding to the polypeptide, preventing an inhibitor or activator from binding to the polypeptide, increasing association of an inhibitor or activator with the polypeptide, or activating or inhibiting expression of the polypeptide.

Any cell expressing a full-length polypeptide of the invention or a fragment thereof can be used to identify modulators. In some embodiments, the cells are eukaryotic cells lines (e.g., HEK293) transformed to express a heterologous ASKRK polypeptide. In some embodiments, a cell expressing an endogenous ASKRK polypeptide, e.g., a pancreatic cell or adrenal cell, is used in screens.

1. Polypeptide Binding Assays

Preliminary screens can be conducted by screening for agents capable of binding to ASKRK polypeptides, as at least some of the agents so identified are likely modulators of a polypeptide of the invention. Binding assays are also useful, e.g., for identifying endogenous proteins that interact with ASKRK. For example, antibodies or other molecules that bind polypeptides of the invention can be identified in binding assays.

Binding assays usually involve contacting an ASKRK polypeptide with one or more test agents and allowing sufficient time for the protein and test agents to form a binding complex. Any binding complexes formed can be detected using any of a number of established analytical techniques. Protein binding assays include, but are not limited to, methods that measure co-precipitation or co-migration or non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in Neurotransmitter Receptor Binding (Yamamura, H. I., et al., eds.), pp. 61–89. Other binding assays involve the use of mass spectrometry or NMR techniques to identify molecules bound the ASKRK polypeptide or displacement of labeled substrates. The ASKRK polypeptides used in these assays can be naturally expressed, cloned or synthesized.

In addition, mammalian or yeast two-hybrid approaches (see, e.g., Bartel, P. L. et al. Methods Enzymol. 254:241 (1995)) can be used to identify polypeptides or other molecules that interact or bind to ASKRK when expressed together in a host cell.

2. Polypeptide Activity

ASKRK activity can be assessed using a variety of in vitro and in vivo assays to determine functional, chemical, and physical effects. These assays include monitoring, for example, catalytic phosphorylation of substrate. An exemplary kinase assay is provided in the examples. Briefly, the ability of ASKRK to phosphorylate a MAP kinase kinase (MKK6) is tested by incubating the substrate with an ASKRK polypeptide in a buffer with $^{32}$P-γATP and measuring the amount of phosphorylated substrate.

Assays formatted for highthroughput use can also be used. For example, kinases catalyze the transfer of a gamma-phosphoryl group from ATP to an appropriate hydroxyl acceptor with the release of a proton. An assay based on the detection of this proton using an appropriately matched buffer/indicator system may therefore be used to detect activity (see, e.g., Chapman & Wong Bioorg Med Chem 10:551–5, 2002).

Alternatively, ASKRK-mediated apoptosis can be used to assay for ASKRK activity. In such assays, hallmarks of apoptosis, e.g., DNA fragmentation, cell viability are measured. Cell viability can be measured using an assay suitable for a high throughput screening format, such as a calorimetric or fluorescent viability assay. For example, an Alamar blue (AB) assay, incorporates a redox indicator that changes the colour or fluorescence in response to metabolic activity. The Alamar blue fluorescences in the presence of living, but not dead, cells. Such an assay can be conveniently read in a microtiter plate or by flow cytometry. Colorimetric assays such as the MTT assay, which measures the reduction of MTT (3-(4,5-dimethyl) thiazol-2-yl-2,5-diphenyl tetrazolium bromide) to formazan, may also be used conveniently in a high throughput format to measure cell viability and proliferation.

Other assays that measure cell number may also be used. These include assays that measure intercalation of dyes into the DNA of a cell. The amount of intercalated dye is directly proportional to cell number. For example, cells can be stained with a dye such as Hoechst 33342, which intercalates in the DNA of vital cell, an cell number determined by measuring the amount of fluorescence. Cells may also be directly counted.

The ASKRK polypeptide of the assay will be selected from a polypeptide with substantial identity to a sequence of SEQ ID NO:2 or other conservatively modified variants thereof. Generally, the amino acid sequence identity will be at least 70%, optionally at least 85%, optionally at least 90–95% to the ASKRK polypeptides exemplified herein, or the polypeptide will have at least 10 contiguous amino acids, more often 20, 25, 30, 25, 50, or 100 contiguous amino acids of SEQ ID NO:2. Optionally, the ASKRK polypeptide used in activity assays will comprise a fragment of a polypeptide of the invention, such as a kinase domain and the like. Either a polypeptide of the invention or a domain thereof can be covalently linked to a heterologous protein to create a chimeric protein used in the assays described herein. A polypeptide of the invention is active when it has an activity value, relative to the control, that is 110%, optionally 150%, 200%, 300%, 400%, 500%, or 1000–2000%.

Candidate inhibitors of ASKRK activity are tested using either recombinant or naturally occurring polypeptides. The protein can be isolated, expressed in a cell, expressed in a membrane derived from a cell, expressed in tissue or in an animal, either recombinant or naturally occurring. For example, tissue slices, dissociated cells, e.g., from tissues expressing polypeptides of the invention, transformed cells, or membranes can be used. Inhibition is tested using one of the in vitro or in vivo assays described herein.

Test compound binding to polypeptides of the invention, a domain, or chimerica protein can be tested in solution, in a bilayer membrane, attached to a solid phase, in a lipid monolayer, or in vesicles. Binding of a test compound can be tested using, e.g., changes in spectroscopic characteristics (e.g., fluorescence, absorbance, refractive index), hydrodynamic (e.g., shape), chromatographic, or solubility properties.

Samples or assays that are treated with a potential inhibitor (e.g., a "test compound") are compared to control samples without the test compound, to examine the extent of modulation. Control samples (untreated with candidate compounds are assigned a relative activity value of 100. Inhibition of the polypeptides of the invention is achieved when the activity value relative to the control is about 90%, optionally 50%, optionally 25-0%.

3. Expression Assays

Screening assays for a compound that modulates the expression of ASKRK polynucleotides and polypeptides are also provided. Screening methods generally involve conducting cell-based assays in which test compounds are contacted with one or more cells expressing ASKRK, and then detecting an increase or decrease in expression (either transcript or translation product). Assays can be performed with any cells that express a ASKRK polypeptide. Some assays may employ cells that express ASKRK at high levels e.g., a pancreatic beta cell or islet cell.

Expression can be detected in a number of different ways. As described infra, the expression level of an ASKRK polynucleotide can be determined by probing the mRNA expressed in a cell with a probe that specifically hybridizes with an ASKRK transcript (or complementary nucleic acid derived therefrom). Alternatively, an ASKRK polypeptide can be detected using immunological methods, e.g. an assay in which a cell lysate is probed with antibodies that specifically bind to the polypeptide.

Reporter systems can also be used to identify modulators of ASKRK expression. A variety of different types of cells can be utilized in reporter assays. Cells that do not endogenously express an ASKRK polypeptide can be prokaryotic, but are preferably eukaryotic. The eukaryotic cells can be any of the cells typically utilized in generating cells that harbor recombinant nucleic acid constructs. Exemplary eukaryotic cells include, but are not limited to, yeast, and various higher eukaryotic cells such as the HEK293, HepG2, COS, CHO and HeLa cell lines.

Various controls can be conducted to ensure that an observed activity is authentic including running parallel reactions with cells that lack the reporter construct or by not contacting a cell harboring the reporter construct with test compound. Compounds can also be further validated as described below.

4. Validation

Agents that are initially identified by any of the foregoing screening methods can be further tested to validate the activity. Modulators that are selected for further study can be tested on a variety of cells, e.g., pancreatic cells such as the beta cell lines HIT-T15, RiNm5, betaTC3, betaHC9, and INS1. Cells that have been engineered to express ASKRK may also be used. For example, fibroblasts that overexpress ASKRK may be used to further validate the activity of the candidate modulator. In an example of such an analysis, cells that express ASKRK are pre-incubated with the modulators and tested for apoptotic activity.

Following such studies, validity of the modulators is used in suitable animal models. The basic format of such methods involves administering a lead compound identified during an initial screen to an animal that serves as a model for humans and then determining if expression or activity of ASKRK is in fact modulated.

The effect of the compound will be assessed in either diabetic animals or in diet-induced insulin resistant animals. The blood glucose and insulin levels will be determined. The animal models utilized in validation studies generally are mammals of any kind. Specific examples of suitable animals include, but are not limited to, primates, mice and rats. For example, monogenic models of diabetes (e.g., ob/ob and db/db mice, Zucker rats and Zucker Diabetic Fatty rats etc) or polygenic models of diabetes (e.g., OLETF rats, GK rats, NSY mice, and KK mice) can be useful for validating modulation of a polypeptide of the invention in a diabetic or insulin resistant animal. In addition, transgenic animals expressing human ASKRK polypeptides can be used to further validate drug candidates.

Compounds are typically selected that increase beta cell viability or improve islet functions. Assays to assess insulin sensitivity and islet function include fasting blood glucose assays, fasting insulin level assays, assessment of glucose levels during an oral or intraperitoneal glucose tolerance test, assessment of insulin or C-peptide levels during an oral or intraperitoneal glucose tolerance test. Other secretagogues, e.g., arginine or glyburide can also be used to test for the glucose specificity of the improvement in islet function.

C. Solid Phase and Soluble High Throughput Assays

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000–20,000 or more different compounds are possible using the integrated systems of the invention. In addition, microfluidic approaches to reagent manipulation can be used.

A molecule of interest (e.g., a ASKRK polypeptide or polynucleotide, or a modulator thereof) can be bound to the solid-state component, directly or indirectly, via covalent or non-covalent linkage, e.g., via a tag. The tag can be any of a variety of components. In general, a molecule that binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, poly-His, etc.) Antibodies to molecules with natural binders such as biotin are also widely available and appropriate tag binders (see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody that recognizes the first antibody. In addition to antibody-antigen interactions, receptor-ligand interactions are also appropriate as tag and tag-binder pairs, such as agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherin family, the integrin family, the selectin family, and the like; see, e.g., Pigott & Power, The Adhesion Molecule Facts Book I (1993)). Similarly, toxins and venoms, viral epitopes, hormones (e.g., opiates, steroids, etc.), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyacrylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly-Gly sequences of between about 5 and 200 amino acids (SEQ ID NO:8). Such flexible linkers are known to those of skill in the art. For example, poly(ethylene glycol) linkers are available from Shearwater Polymers, Inc., Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent that fixes a chemical group to the surface that is reactive with a portion of the tag binder. For example, groups that are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature (see, e.g., Merrifield, J. Am. Chem. Soc. 85:2149–2154 (1963) (describing solid phase synthesis of, e.g., peptides); Geysen et al., J. Immun. Meth. 102:259–274 (1987) (describing synthesis of solid phase components on pins); Frank and Doring, Tetrahedron 44:60316040 (1988) (describing synthesis of various peptide sequences on cellulose disks); Fodor et al., Science, 251:767–777 (1991); Sheldon et al., Clinical Chemistry 39(4):718–719 (1993); and Kozal et al., Nature Medicine 2(7):753759 (1996) (all describing arrays of biopolymers fixed to solid substrates). non-chemical approaches for fixing tag binders to substrates include other common methods, such as heat, cross-linking by UV radiation, and the like.

The invention provides in vitro assays for identifying, in a high throughput format, compounds that can modulate the expression or activity of ASKRK. Control reactions that measure ASKRK activity in a cell in a reaction that does not include a potential modulator are optional, as the assays are highly uniform. Such optional control reactions are appropriate and increase the reliability of the assay. Accordingly, in some embodiments, the methods of the invention include such a control reaction. For each of the assay formats described, "no modulator" control reactions that do not include a modulator provide a background level of binding activity.

In some assays it will be desirable to have positive controls. At least two types of positive controls are appropriate. First, a known activator of ASKRK can be incubated with one sample of the assay, and the resulting increase in signal resulting from an increased expression level or activity of a ASKRK polypeptide or polynucleotide are determined according to the methods herein. Second, a known inhibitor of a polypeptide or a polynucleotide of the invention can be added, and the resulting decrease in signal for the expression or activity of the ASKRK polypeptide or polynucleotide can be similarly detected. It will be appreciated that modulators can also be combined with activators or inhibitors to find modulators that inhibit the increase or decrease that is otherwise caused by the presence of the known modulator of an ASKRK polypeptide or polynucleotide.

Compositions, Kits and Integrated Systems

The invention provides compositions, kits and integrated systems for practicing the assays described herein using ASKRK nucleic acids or polypeptides, antibodies, etc.

The invention provides assay compositions for use in solid phase assays; such compositions can include, for example, one or more nucleic acids encoding ASKRK immobilized on a solid support, and a labeling reagent. In each case, the assay compositions can also include additional reagents that are desirable for hybridization. Modulators of ASKRK expression or activity can also be included in the assay compositions.

The invention also provides kits for carrying out the assays described herein. The kits typically include a probe that comprises an antibody that specifically binds an ASKRK polypeptide or a polynucleotide sequence encoding an ASKRK polypeptide, and a label for detecting the presence of the probe. Kits can include any of the compositions noted above, and optionally further include additional components such as instructions to practice a high-throughput method of assaying for an effect on ASKRK expression or activity, one or more containers or compartments (e.g., to hold the probe, labels, or the like), a control modulator of ASKRK expression or activity, a robotic armature for mixing kit components or the like.

The invention also provides integrated systems for high-throughput screening of potential modulators for an effect on ASKRK expression or activity. The system can include a robotic armature which transfers fluid from a source to a destination, a controller which controls the robotic armature, a label detector, a data storage unit which records label detection, and an assay component such as a microtiter dish comprising a well having a reaction mixture or a substrate comprising a fixed nucleic acid or immobilization moiety.

A number of robotic fluid transfer systems are available, or can easily be made from existing components. For example, a Zymate XP (Zymark Corporation; Hopkinton, Mass.) automated robot using a Microlab 2200 (Hamilton; Reno, Nev.) pipetting station can be used to transfer parallel samples to 96 well microtiter plates to set up several parallel simultaneous binding assays.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical image.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g., by fluorescent or dark field microscopic techniques.

Administration and Pharmaceutical Compositions

ASKRK modulators, e.g., inhibitors can be administered directly to the mammalian subject for modulation of activity of a polypeptide of the invention in vivo. Administration is by any of the routes normally used for introducing a modulator compound into ultimate contact with the tissue to be treated and is well known to those of skill in the art. Although more than one route can be used to administer a particular composition, a particular route can often provide a more immediate and more effective reaction than another route.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., Remington's Pharmaceutical Sciences, $17^{th}$ ed. 1985)).

Inhibitors of the expression or activity of ASKRK alone or in combination with other suitable components, can be prepared for injection or for use in a pump device. Pump devices (also known as "insulin pumps") are commonly used to administer insulin to patients and therefore can be easily adapted to include compositions of the present invention. Manufacturers of insulin pumps include Animas, Disetronic and MiniMed.

ASKRK inhibitors, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, or intrathecally. The formulations of compounds can be presented in unit-dose or multi-dose sealed containers, such as ampoules and vials. Solutions and suspensions can be prepared from sterile powders, granules, and tablets of the kind previously described. The modulators can also be administered as part of a prepared food or drug.

The dose administered to a patient, in the context of the present invention should be sufficient to induce a beneficial response in the subject over time. The optimal dose level for any patient will depend on a variety of factors including the efficacy of the specific modulator employed, the age, body weight, physical activity, and diet of the patient, on a possible combination with other drugs, and on the severity of the case of diabetes. It is recommended that the daily dosage of the modulator be determined for each individual patient by those skilled in the art in a similar way as for known insulin compositions. The size of the dose also will be determined by the existence, nature, and extent of any adverse side-effects that accompany the administration of a particular compound or vector in a particular subject.

In determining the effective amount of the modulator to be administered a physician may evaluate circulating plasma levels of the modulator, modulator toxicity, and the production of anti-modulator antibodies. In general, the dose equivalent of a modulator is from about 1 ng/kg to 10 mg/kg for a typical subject.

For administration, modulators of the present invention can be administered at a rate determined by the LD-50 of the modulator, and the side-effects of the modulator at various concentrations, as applied to the mass and overall health of the subject. Administration can be accomplished via single or divided doses.

The compounds of the present invention can also be used effectively in combination with one or more additional active agents depending on the desired target therapy (see, e.g., Turner, N. et al. Prog. Drug Res. (1998) 51: 33–94; Haffner, S. Diabetes Care (1998) 21: 160–178; and DeFronzo, R. et al. (eds.), Diabetes Reviews (1997) Vol. 5 No. 4). A number of studies have investigated the benefits of combination therapies with oral agents (see, e.g., Mahler, R., J. Clin. Endocrinol. Metab. (1999) 84: 1165–71; United Kingdom Prospective Diabetes Study Group; UKPDS 28, Diabetes Care (1998) 21: 87–92; Bardin, C. W.,(ed.), Current Therapy In Endocrinology And Metabolism, 6th Edition (Mosby—Year Book, Inc., St. Louis, Mo. 1997); Chiasson, J. Et al., Ann. Intern. Med. (1994) 121: 928–935; Coniff, R. et al., Clin. Ther. (1997) 19: 16–26; Coniff, R. et al., Am. J. Med. (1995) 98: 443–451; and Iwamoto, Y. et al., Diabet. Med. (1996) 13 365–370; Kwiterovich, P. Am. J. Cardiol (1998) 82(12A): 3U–17U). These studies indicate that modulation of diabetes, among other diseases, can be further improved by the addition of a second agent to the therapeutic regiment. Combination therapy includes administration of a single pharmaceutical dosage formulation that contains a modulator of the invention and one or more additional active agents, as well as administration of a modulator and each active agent in its own separate pharmaceutical dosage formulation. For example, a modulator and a thiazolidinedione can be administered to the human subject together in a single oral dosage composition, such as a tablet or capsule, or each agent can be administered in separate oral dosage formulations. Where separate dosage formulations are used, a modulator and one or more additional active agents can be administered at essentially the same time (i.e., concurrently), or at separately staggered times (i.e., sequentially). Combination therapy is understood to include all these regimens.

One example of combination therapy can be seen in treating pre-diabetic individuals (e.g., to prevent progression into type 2 diabetes) or diabetic individuals (or treating diabetes and its related symptoms, complications, and disorders), wherein the modulators can be effectively used in combination with, for example, sulfonylureas (such as chlorpropamide, tolbutamide, acetohexamide, tolazamide, glyburide, gliclazide, glynase, glimepiride, and glipizide); biguanides (such as metformin); a PPAR beta delta agonist; a ligand or agonist of PPAR gamma such as thiazolidinediones (such as ciglitazone, pioglitazone (see, e.g., U.S. Pat. No. 6,218,409), troglitazone, and rosiglitazone (see, e.g., U.S. Pat. No. 5,859,037)); PPAR alpha agonists such as clofibrate, gemfibrozil, fenofibrate, ciprofibrate, and bezafibrate; dehydroepiandrosterone (also referred to as DHEA or its conjugated sulphate ester, DHEA-SO4); antiglucocorticoids; TNF$\alpha$ inhibitors; $\alpha$-glucosidase inhibitors (such as acarbose, miglitol, and voglibose); amylin and amylin derivatives (such as pramlintide, (see, also U.S. Pat. Nos. 5,902,726; 5,124,314; 5,175,145 and 6,143,718.)); insulin secretogogues (such as repaglinide, gliquidone, and nateglinide (see, also, U.S. Pat. Nos. 6,251,856; 6,251,865; 6,221,633; 6,174,856)), and insulin.

Gene Therapy

Conventional viral and non-viral based gene transfer methods can be used to introduce nucleic acids encoding engineered ASKRK polypeptides, e.g., dominant negative polypeptide, in mammalian cells or target tissues, or alternatively, nucleic acids that are inhibitors of ASKRK activity, e.g., siRNAs, anti-sense RNAs, ribozymes and the like. Such methods can be used to administer nucleic acids in vitro. In some embodiments, the nucleic acids encoding polypeptides of the intention are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, Science 256:808–813 (1992); Nabel & Felgner, TIBTECH 11:211–217 (1993); Mitani & Caskey, TIBTECH 11: 162–166 (1993); Dillon, TIBTECH 11:167–173 (1993); Miller, Nature 357:455–460 (1992); Van Brunt, Biotechnology 6(10):1149–1154 (1988); Vigne, Restorative Neurology and Neuroscience 8:35–36 (1995);

Kremer & Perricaudet, British Medical Bulletin 51(1):31–44 (1995); Haddada et al. in Current Topics in Microbiology and Immunology Doerfler and Böhm (eds) (1995); and Yu et al., Gene Therapy 1:13–26 (1994).

In some embodiments, small interfering RNAs are administered. In mammalian cells, introduction of long dsRNA (>30 nt) often initiates a potent antiviral response, exemplified by nonspecific inhibition of protein synthesis and RNA degradation. The phenomenon of RNA interference is described and discussed, e.g., in Bass, Nature 411:428–29 (2001); Elbahir et al., Nature 411:494–98 (2001); and Fire et al., Nature 391:806–11 (1998), where methods of making interfering RNA also are discussed. The siRNAs based upon the ASKRK sequence disclosed herein are less than 100 base pairs, typically 30 bps or shorter, and are made by approaches known in the art. Exemplary siRNAs according to the invention could have up to 29 bps, 25 bps, 22 bps, 21 bps, 20 bps, 15 bps, 10 bps, 5 bps or any integer thereabout or therebetween.

Non-Viral Delivery Methods

Methods of non-viral delivery of nucleic acids encoding engineered polypeptides of the invention include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. No. 5,049,386, U.S. Pat. No. 4,946,767; and U.S. Pat. No. 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, Science 270:404–410 (1995); Blaese et al., Cancer Gene Ther. 2:291–297 (1995); Behr et al., Bioconjugate Chem. 5:382–389 (1994); Remy et al., Bioconjugate Chem. 5:647–654 (1994); Gao et al., Gene Therapy 2:710–722 (1995); Ahmad et al., Cancer Res. 52:4817–4820 (1992); U.S. Pat. Nos. 4,186,183, 4,217,344, 4,235,871, 4,261,975, 4,485,054, 4,501,728, 4,774,085, 4,837,029, and 4,946,787).

Viral Delivery Methods

The use of RNA or DNA viral based systems for the delivery of nucleic acids encoding engineered ASKRK polypeptides or nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of polypeptides of the invention could include retroviral, lentivirus, adenoviral, adeno-associated and herpes simplex virus vectors for gene transfer. Viral vectors are currently the most efficient and versatile method of gene transfer in target cells and tissues, Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6–10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Virol. 66:2731–2739 (1992); Johann et al., J. Virol. 66:1635–1640 (1992); Sommerfelt et al., Virol. 176:58–59 (1990); Wilson et al., J. Virol. 63:2374–2378 (1989); Miller et al., J. Virol. 65:2220–2224 (1991); PCT/US94/05700).

In applications where transient expression of a nucleic acid is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., Virology 160:38–47 (1987); U.S. Pat. No. 4,797,368; WO 93/24641; Kotin, Human Gene Therapy 5:793–801 (1994); Muzyczka, J. Clin. Invest. 94:1351 (1994)). Construction of recombinant AAV vectors are described in a number of publications, including U.S. Pat. No. 5,173,414; Tratschin et al., Mol. Cell. Biol. 5:3251–3260 (1985); Tratschin, et al., Mol. Cell. Biol. 4:2072–2081 (1984); Hermonat & Muzyczka, PNAS 81:6466–6470 (1984); and Samulski et al., J. Virol. 63:03822–3828 (1989).

pLASN and MFG-S are examples are retroviral vectors that have been used in clinical trials (Dunbar et al., Blood 85:3048–305 (1995); Kohn et al., Nat. Med. 1: 1017–102 (1995); Malech et al., PNAS 94:22 12133–12138 (1997)). PA317/pLASN was the first therapeutic vector used in a gene therapy trial. (Blaese et al., Science 270:475–480 (1995)). Transduction efficiencies of 50% or greater have been observed for MFG-S packaged vectors. (Ellem et al., Immunol Immunother. 44(1):10–20 (1997); Dranoff et al., Hum. Gene Ther. 1:111–2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., Lancet 351:9117 1702–3 (1998), Kearns et al., Gene Ther. 9:748–55 (1996)).

Replication-deficient recombinant adenoviral vectors (Ad) can be engineered such that a desired nucleic acid replaces the Ad E1a, E1b, and E3 genes; subsequently the replication defector vector is propagated in human 293 cells that supply deleted gene function in trans. Ad vectors can transduce multiply types of tissues in vivo, including non-dividing, differentiated cells such as those found in the liver, kidney, muscle, and pancreatic system tissues. Conventional Ad vectors have a large carrying capacity. An example of the use of an Ad vector in a clinical trial involved polynucleotide therapy for antitumor immunization with intramuscular injection (Sterman et al., Hum. Gene Ther. 7:1083–9 (1998)). Additional examples of the use of adenovirus vectors for gene transfer in clinical trials include Rosenecker et al., Infection 24:1 5–10 (1996); Sterman et al., Hum. Gene Ther. 9:7 1083–1089 (1998); Welsh et al., Hum. Gene Ther. 2:205–18 (1995); Alvarez et al., Hum. Gene Ther. 5:597–613 (1997); Topf et al., Gene Ther. 5:507–513 (1998); Sterman et al., Hum. Gene Ther. 7:1083–1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type, e.g., pancreatic tissue. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., PNAS 92:9747–9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient.

Ex vivo cell transfection for diagnostics, research, or for gene therapy (e.g., via re-infusion of the transfected cells into the host organism) is well known to those of skill in the art. In some embodiments, cells are isolated from the subject organism, transfected with a nucleic acid, e.g., an antisense ASKRK nucleic acid, an expression construct expressing an dominant negative construct, a ribozyme and the like, and re-infused back into the subject organism (e.g., patient). Various cell types suitable for ex vivo transfection are well known to those of skill in the art (see, e.g., Freshney et al., Culture of Animal Cells, A Manual of Basic Technique (3rd ed. 1994)) and the references cited therein for a discussion of how to isolate and culture cells from patients).

Vectors (e.g., retroviruses, adenoviruses, liposomes, etc.) containing therapeutic nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention, as described below (see, e.g., Remington's Pharmaceutical Sciences, 17th ed., 1989).

Diagnosis of Diabetes

The present invention also provides methods of diagnosing diabetes or a predisposition of at least some of the pathologies of diabetes. Diagnosis can involve determination of a genotype of an individual (e.g., with SNPs) and comparison of the genotype with alleles known to have an association with the occurrence of diabetes. Alternatively, diagnosis also involves determining the level of an ASKRK polypeptide or polynucleotide in a patient and then comparing the level to a baseline or range. Typically, the baseline value is representative of a polypeptide or polynucleotide of the invention in a healthy (e.g., non-diabetic) person.

As discussed above, variation of levels (e.g., low or high levels) of a polypeptide or polynucleotide of the invention compared to the baseline range indicates that the patient is either diabetic or at risk of developing at least some of the pathologies of diabetes (e.g., pre-diabetic). For example, a patient with increased levels of ASKRK polypeptide, nucleic acid, e.g., mRNA, or and/or ASKRK activity in pancreas relative to normal may have an increased risk for diabetes. The level of a polypeptide in a non-diabetic individual can be a reading from a single individual, but is typically a statistically relevant average from a group of non-diabetic individuals. The level of a polypeptide in a lean individual can be represented by a value, for example in a computer program.

In some embodiments, the level of ASKRK polypeptide or polynucleotide is measured by taking a blood, urine of tissue sample from a patient and measuring the amount of a polypeptide or polynucleotide of the invention in the sample using any number of detection methods, such as those discussed herein. For instance, fasting and fed blood or urine levels can be tested.

In some embodiments, the baseline level and the level in a non-diabetic sample from an individual, or at least two samples from the same individual, differ by at least about 5%, 10%, 20%, 50%, 75%, 100%, 150%, 200%, 300%, 400%, 500%, 1000% or more. In some embodiments, the sample from the individual is greater by at least one of the above-listed percentages relative to the baseline level. In some embodiments, the sample from the individual is lower by at least one of the above-listed percentages relative to the baseline level.

In some embodiments, the level of an ASKRK polypeptide or polynucleotide is used to monitor the effectiveness of treatments for diabetes such as thiazolidinediones, metformin, sulfonylureas and other standard therapies. In some embodiments the activity or expression of an ASKRK polypeptide or polynucleotide is measured prior to and after treatment of diabetic or pre-diabetic patients with antidiabetic therapies as a surrogate marker of clinical effectiveness. For example, the greater the reduction in expression or activity ASKRK indicates greater effectiveness.

Glucose/insulin tolerance tests can also be used to detect the effect of glucose levels on levels of ASKRK polypeptides or polynucleotides. In glucose tolerance tests, the patient's ability to tolerate a standard oral glucose load is evaluated by assessing serum and urine specimens for glucose levels. Blood samples are taken before the glucose is ingested, glucose is given by mouth, and blood or urine glucose levels are tested at set intervals after glucose ingestion. Similarly, meal tolerance tests can also be used to detect the effect of insulin or food, respectively, on levels of ASKRK.

EXAMPLES

A custom Affymetrix oligonucleotide array probe set MBXMUSISL25681_at was identified as being highly enriched in mouse islets and a beta cell line (βHC9) (FIG. 1). This sequence was then used to design primers to obtain a larger clone containing a coding sequence that is 59% identical to the mouse ASK1 coding sequence. The kinase domains are 86% identical between the ASK1 and ASKRK. Anti-mASKRK antibodies were generated using the C-terminal peptide sequence SQHRRQMQESSQ (SEQ ID NO:9) for both immunization and affinity purification. The affinity purified antibody was used to demonstrate that ASKLRK protein is abundant in islet beta cells, but is much less abundant in alpha cells and the surrounding acinar tissue (data not shown).

The mouse ASKRK sequence was used to find homologous human genomic sequences, and these were, in turn, used to design primers for RT-PCR to obtain a partial coding sequence for human ASKRK. Also, by comparison of the synteny between rat and human genomic sequences 5' of this partial sequence, the full coding sequence of human ASKRK (SEQ ID NO:1, nucleic acid sequence, SEQ ID NO:2, protein sequence) was obtained. A sequence comparison of the full-length human and partial mouse ASKRK amino acid sequences is shown in FIG. 2.

Figure 3:
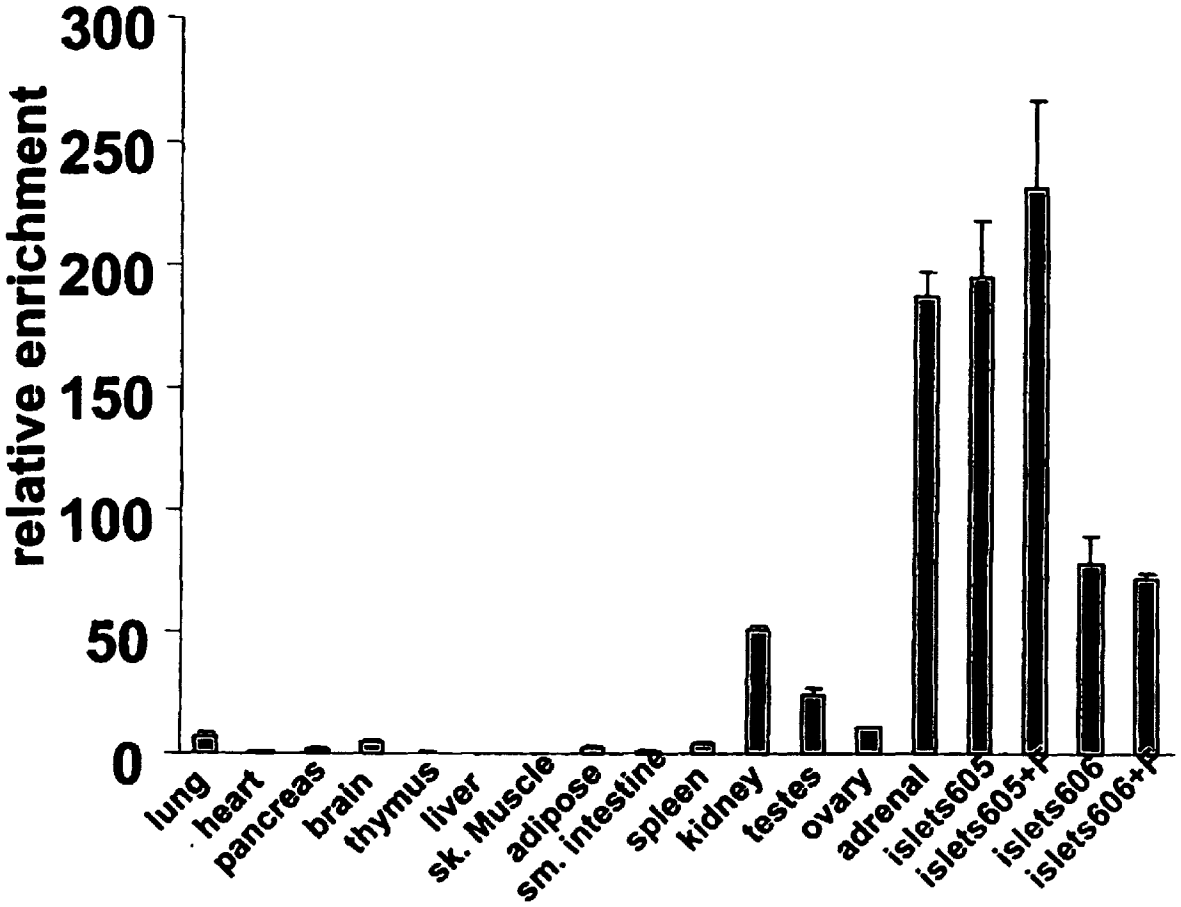
FIG. 3 shows the results of a real-time PCR analysis. Taqman real-time polymerase chain reaction experiment using human tissue cDNA templates, including cDNA prepared from islets which had been treated or not treated with free fatty acids. The probe (300 nM) and primer (900 nM) set used was specific to hASKRK sequence downstream of the kinase domain. 18S RNA was used as an internal control.

The DNA encoding human ASKRK was assembled for the full coding and deletion constructs described below. Human ASKRK-specific primers were also used for TaqMan (ABI) analysis to confirm that the human ASKRK mRNA was also enriched in islets relative to most other tissues. ASKRK mRNA is also expressed in human adrenal gland (FIG. 3). Anti hASKRK antibodies were raised by immunizing rabbits with the C-terminal peptide sequence YRRAQEASETKDKA (SEQ ID NO:10). This antibody was used to confirm ASKRK expression in functional studies.

Figure 4:
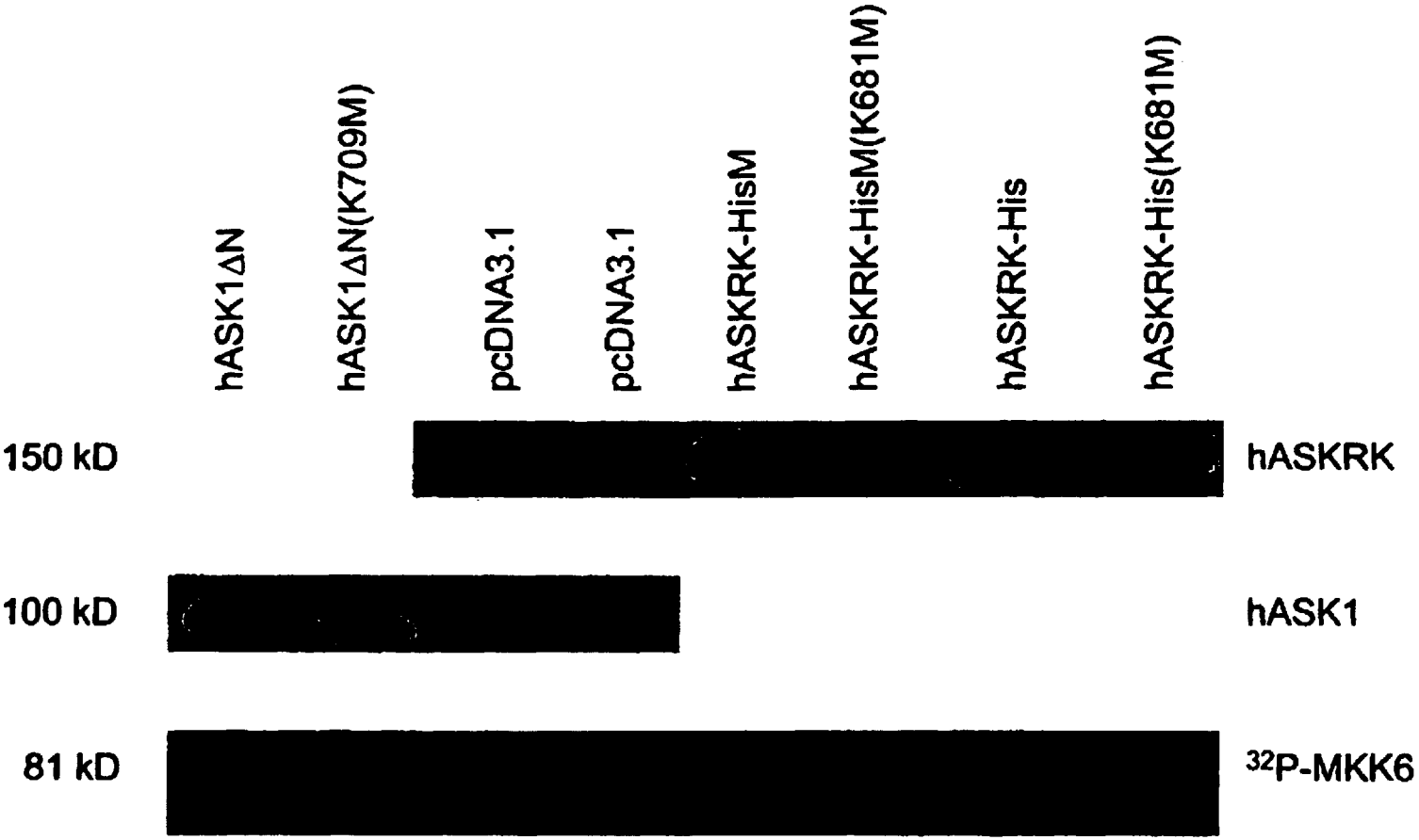
FIG. 4 shows the results of a transfection experiment to show ASKRK function. hASKRK expression increases MKK6 phosphorylating activity in fibroblasts. Mammalian expression constructs of hASK1ΔN, the kinase deficient mutant hASK1ΔN(K709M), hASKRK-H6M, the kinase deficient mutant hASKRK-H6M (K681M), hASKRK-H6, and the kinase deficient mutant hASKRK-H6 (K681M) in pcDNA3.1 or the empty vector were transfected into HEK293 cells. Forty-eight hours later the cells were lysed in RIPA buffer at 4° C. and cleared by centrifugation. 18 ng of each lysate was assayed for kinase activity using MKK6 (inactive) (Upstate Biotechnology) as substrate ATP/$Mg^{2+}$ (containing 1 mCi/ml $^{32}$P-γ-ATP) and Upstate Assay Dilution Buffer (ADB) to adjust each volume to 50 ml. Kinase assay was performed at 30 degrees with constant agitation for 30'. 20 μl 4× sample buffer was added to each tube to stop kinase assay. Samples were heated 95° C. for 10' then fractionated by electrophoresis at 40 mA on 12% polyacrylamide gel. 50 ml of each lysate was also heated with 20 μl 4×SB and electrophoresed on 12% gel for Western blotting. Gels were transferred to membranes at 350 mA using semi-dry transfer technique. Kinase assay membrane was put with film for 2 hours at −80 degrees. Western blot membrane was blocked 3 hrs with 5% milk TBST, treated with rabbit anti-hASK2 antibody (1:2000) or rabbit-anti-hASK1 antibody (1:1000) in 5% milk TBST 1 hour, washed 3×15' TBST, treated with goat-anti-rabbit-HRP (1:10,000) in 5% milk TBST for 45', washed 3×15' TBST, treated with Pierce SuperSignal (50:50) 2' and put with film for 5–25' exposures.

To examine the function of ASKRK in cells, we transfected HEK293 fibroblasts with constructs containing the full coding sequence in pcDNA3.1 with an N-terminal His tag or with an identical construct in which the codon for K681 was altered to produce M681. The anti-human ASKRK antibody specifically detects a 150 kilodalton protein in the ASKRK-His- and ASKRK-His(K681M)-transfected cells that is not produced in cells transfected with pcDNA3.1 alone. The predicted molecular weight of the 1313 amino acid ASKRK protein is 147 kilodaltons. Lysates from cells expressing hASKRK-HisM, but not hASKRK-HisM(K681M), displayed MKK6 phosphorylating activity similar to that of lysates from hASK1ΔN transfected cells (FIG. 4).

Figure 5:
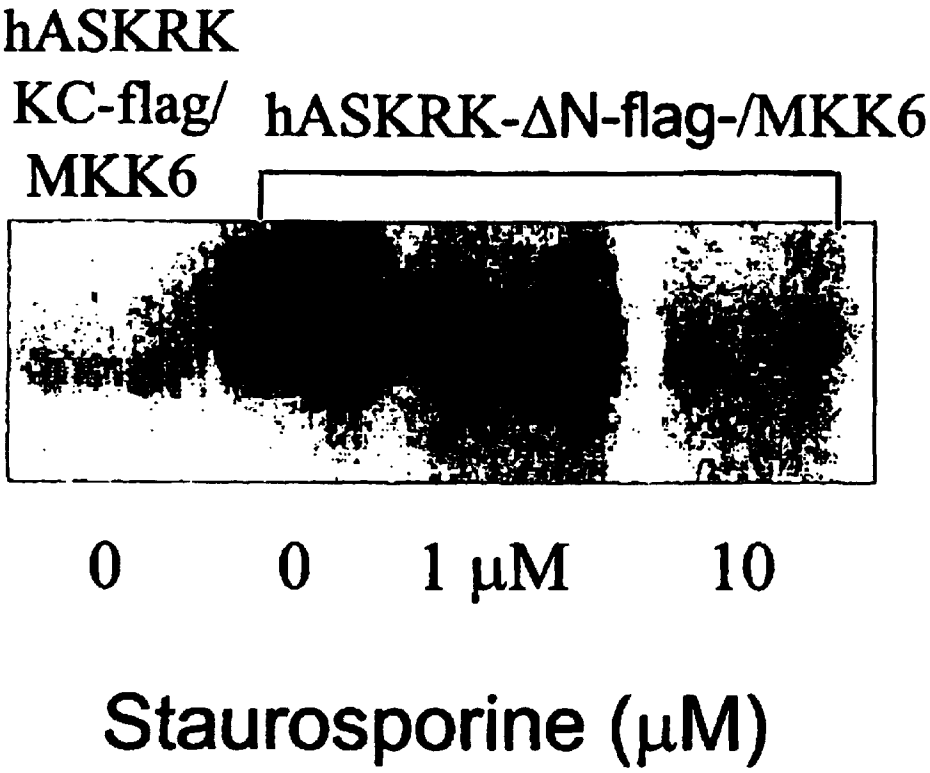
FIG. 5: Purified hASKRK-ΔN-flag phosphorylates MKK6 and is inhibited by stuarosporine. hASKRK-KC-flag (a construct containing the kinase domain and C-terminal domain of ASKRK with a C-terminal flag epitope) or hASKRK-DN-flag baculovirus was used to infect $10^8$ sf21 cells two days before lysing the cells in 0.5% Triton X-100, 50 mM Tris-HCl pH 7.5, 0.1 mM EGTA, 15 mm DTT. The lysate was incubated with M2-Flag resin, washed and eluted with 500 ml of 400 mg/ml FLAG peptide in 0.1% Triton X-100, 50 mM Tris-HCl pH 7.5, 0.1 mM EGTA, 15 mM DTT. The kinase reactions were performed by taking a 30 μl aliquot of kinase eluate and adding 5 μl MKK6 (1.5 mg), 10 μl ATP (10 mCi gamma $^{32}$P ATP 4.5 mM ATP-$MgCl_2$), and 5 μl Assay Dilution Buffer (500 mM Tris-HCl pH 7.5, 1 mM EGTA, 150 mM DTT). Staurosporine was added to the concentrations indicated. Reactions are incubated for 30 minutes at 30° C. with agitation at 5 min intervals. Reactions were stopped with SDS-gel sample buffer, fractionated by 10% SDS-PAGE and transferred to a PVDF membrane before exposure to a phosphor screen for detection.

To determine whether this MKK6 phosphorylating activity was intrinsic to hASKRK, we generated an N-terminally truncated version of the protein missing the first 168 amino acids, but tagged with a FLAG epitope sequence for purification. After expression of a baculovirus construct containing hASKRK-ΔN-flag in sf21 cells, we purified this protein on an M2-FLAG antibody column. Purified hASKRK-ΔN-flag was able to transfer phosphate to MKK6, and this phosphorylation was inhibited by the protein kinase inhibitor staurosporine. A protein with a larger N-terminal deletion (missing the first 678 amino acids), but also produced as a flag-tagged protein in baculovirus construct infected sf21 cells, did not have significant MKK6 phosphorylating activity (FIG. 5).

Figure 6:
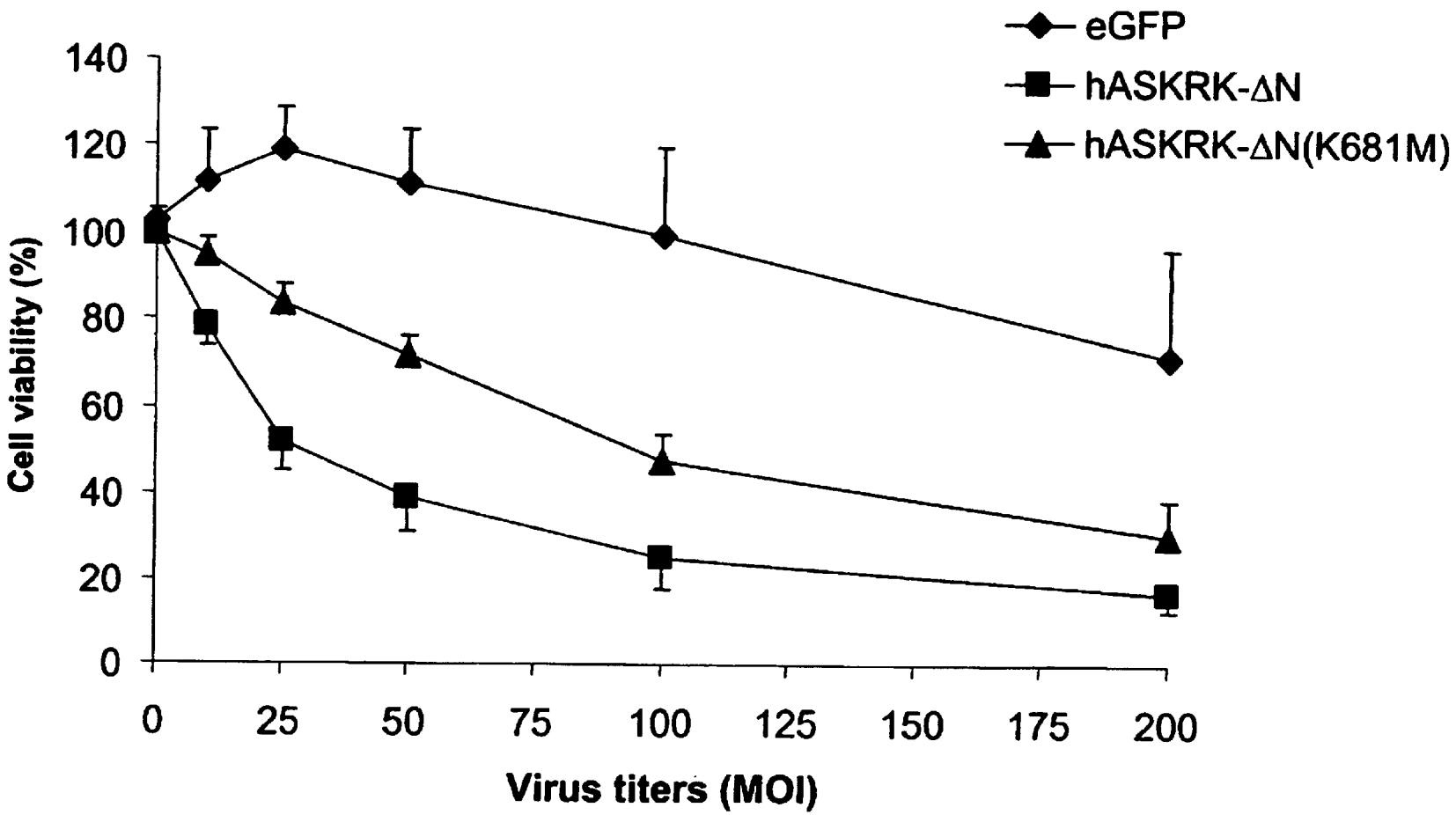
FIG. 6. Ad-hASKRK-ΔN Infection induces cell death in HeLa cells. HeLa cells were seeded to 96-well plates (~25,000/well) one day before viral infection and allowed to grow to approximately 70% confluency in regular DMEM medium. Cells were infected with the Ad-eGFP, Ad-ASKRK-ΔN or Ad-ASKRK-ΔN(K681M) virus at MOI of 0–200 in the viral infection medium (DMEM+5% heat-inactivated FCS) for 14–16 hours, and cultured for a second day in regular culture medium. The degree of cell death was measured by the XTT assay with the Cell Proliferation Kit-II (Boehringer Mannheim, Indianapolis, Ind.) 48-h after viral infection.

Since an N-terminally truncated version of ASK1 induces cell death in a HeLa cells via apoptosis, we examined whether adenovirus constructs expressing N-terminally truncated versions of hASKRK promoted loss of viability when used to infect HeLa cells in culture. Adenovirus hASKRK-ΔN infection caused a 60% loss of viability by XTT assay, whereas the similar adenovirus without the hASKRK coding sequence did not reduce viability at the same multiplicity of infection (MOI). The inactivating K681M mutation reduced the loss-of-viability inducing activity of the protein by 50% at the same MOI (FIG. 6).

Figure 7:
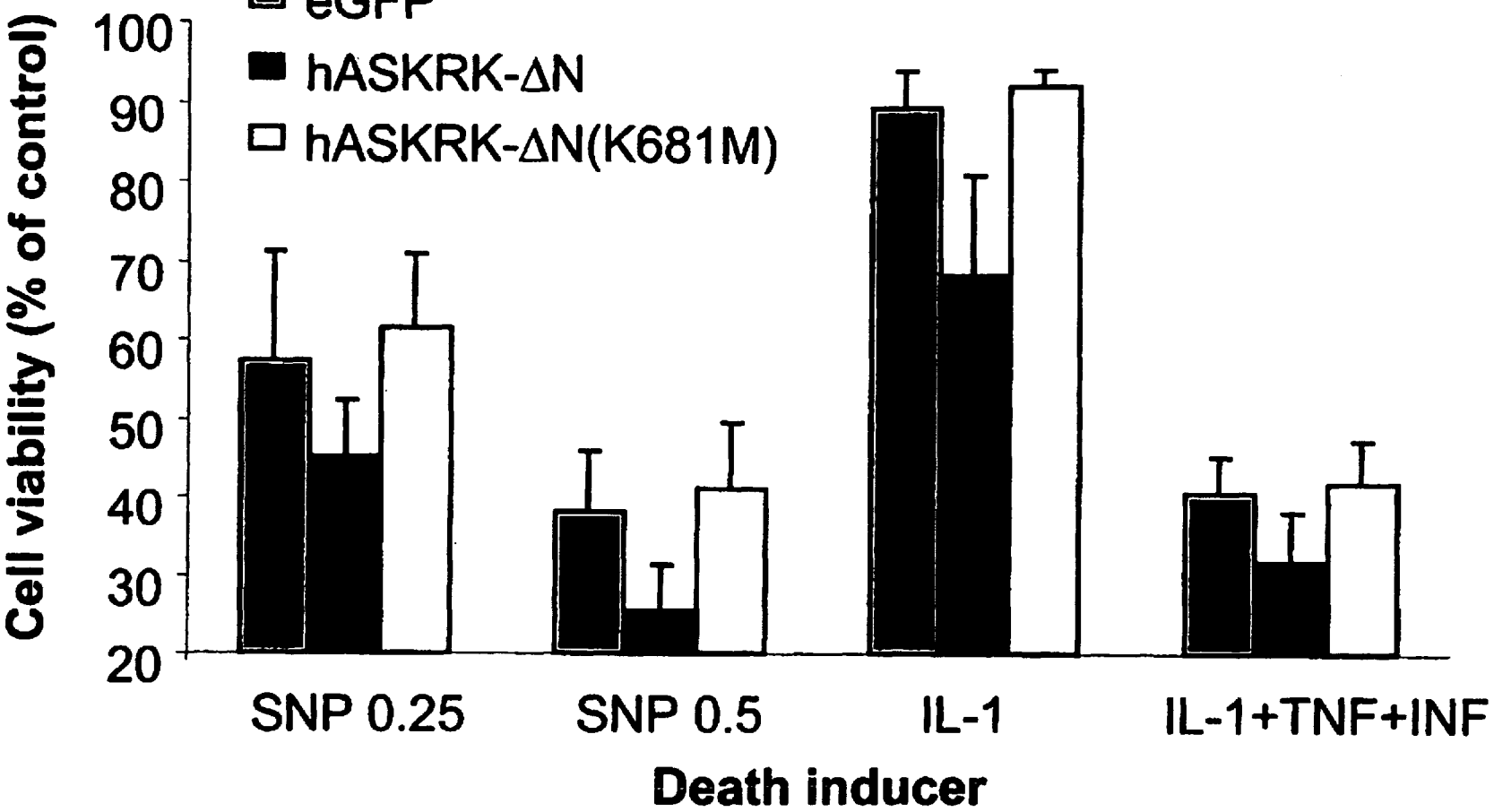
FIG. 7. Effects of Ad-ASKRK-ΔN infection SNP and cytokine-induced cell death in βHC9 cells. The insulin-secreting βHC9 cells were seeded and grown in 96-well plates one day before the viral infection with Ad-eGFP, Ad-ASKRK-ΔN or Ad-ASKRK-ΔN(K681M) virus at MOI of 50. After an overnight exposure to the viruses, cells were treated with sodium nitroprusside (SNP; 0.25–0.5 mM), human IL-1β (1 ng/ml, Sigma) alone or IL-1 with human TNF-α (10 ng/ml, BD Bioscience) and mouse Interferon-γ (50 ng/ml, Sigma) in DMEM medium for 24 hours. Cell viability was measured by the XTT assay as described in the previous figure.

A variety of proapoptotic stimuli can reduce the viability of beta cells in culture. The NO donor sodium nitroprusside (SNP), and the cytokines IL-1, TNF-α and interferony promote loss of viability in the beta cell line βHC9, and this activity is enhanced by prior infection with the hASKRK-ΔN adenovirus, but not with the same virus without hASKRK coding sequence and not with a kinase activity-deficient hASKRK-ΔN(K681M) adenovirus (FIG. 7).

We conclude that ASKRK is a loss-of-viability inducing kinase that is abundantly and selectively expressed in beta cells. Reducing the kinase activity of this protein also causes a reduction in its capacity to cause cell death.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims one of ordinary skill in the art in light of the teachings of this invention that certain changes and modifications may be made thereto without departing from the spirit or scope of the appended claims.

All publications and patent applications cited in this specification are herein incorporated by reference as if each individual publication or patent application were specifically and individually indicated to be incorporated by reference.

TABLE OF SEQUENCES

SEQ ID NO:1 Human ASKRK Nucleic Acid Sequence.

ATGGAGAGCGGCGGTGGGAATGCTCCGGCCGGGGCCCTCGGGGCGGCGAG
CGAGTCCCCTCAGTGCCCGCCGCCGCCGGGGGTGGAGGGCGCGGCCGGGC
CGGCGGAGCCCGACGGGGCGGCGGAGGGCGCGGCAGGCGGCAGCGGCGAG
GGCGAGCGTGGGGGCGGGCCGCGGCGGGCTCTGCGGGCAGTATACGTGCG
CAGTGAGAGCTCCCAGGGCGGCGCGGCCGGCGGCCCGGAGGCTGGGGCGC
GGCAGTGCCTGCTGCGGGCCTGCGAGGCCGAGGGCGCTCACCTCACCTCC
GTGCCCTTCGGGGAGCTGGACTTCGGGGAGACGGCCGTGCTCGACGCCTT
CTACGACGCAGATGTTGCTGTGGTAGACATGAGCGATGTCTCCAGACAG
CCTTCCCTCTTCTACCATCTTGGAGTCCGAGAAAGCTTTGACATGGCCAA
TAATGTGATCTTGTACCATGACACCGATGCCGACACTGCTCTCTCTTTGA
AGGACATGGTAACTCAAAAAAACACAGCATCCAGTGGAAATTATTATTT
CATCCCATACATCGTGACACCGTGCACTGATTATTTTTGCTGCGAGAGTG
ATGCCCAGACAGGAGCCTCCGAGTACATGCAGCCCAACTGGGAGAACATC
CTGGGCCCGCTGTGCATGCCTTTGGTGGACAGGTTCATTAGCCTCCTTAA
GGACATCCACGTGACCTCATGTGTTTATTATTACAAAGAAACCTTGTTAA
ATGACATCCGGAAAGCCAGAGAGAAATACCAAGGTGAGGAACTGGCGAAG
GAGCTAGCTCGGATCAAGCTCCGCATGGATAATACTGAGGTTCTGACCTC
AGACATCATCATTAACTTACTCCTGTCCTACCGTGATATCCAGGACTATG
ATGCGATGGTGAAGCTGGTGGAAACACTGGAGATGCTGCCTACGTGTGAT
TTGGCCGATCAGCATAACACTAAATTCCACTATGCGTTTGCACTGAATAG
GAGAAACAGCACAGGTGACCGTGAGAAGGCTCTGCAGATCATGCTCCAGG
TTCTGCAGAGCTGTGATCACCCGGGCCCCGACATGTTCTGCCTGTGTGGG
AGGATCTACAAGGACATCTTCTTGGATTCAGACTGCAAAGATGACACCAG
CCGCGACAGCGCCATTGAGTGGTATCGCAAAGGGTTTGAACTCCAGTCAT
CCCTCTATTCGGGAATTAATCTTGCAGTTTTGCTGATTGTTGCTGGACAA
CAATTTGAAACTTCCTTGGAACTAAGGAAAATAGGTGTCCGGCTGAACAG
TTTGTTGGGAAGAAAAGGGAGCTTGGAGAAAATGAACAATTACTGGGATG
TGGGTCAGTTCTTCAGCGTCAGCATGCTGGCCCATGATGTCGGGAAAGCC
GTCCAGGCAGCAGAGAGGTTGTTCAAACTGAAACCTCCAGTCTGGTACCT
GCGATCATTAGTTCAGAACTTGTTACTAATTCGGCGCTTCAAGAAAACCA
TTATTGAACACTCGCCCAGGCAAGAGCGGCTGAACTTCTGGTTAGATATA
ATTTTTGAGGCAACAAATGAAGTCACTAATGGACTCAGATTTCCAGTTCT
GGTCATAGAGCCAACCAAAGTGTACCAGCCTTCTTATGTTTCCATAAACA
ATGAAGCCGAGGAGAGAACAGTTTCTTTATGGCATGTCTCACCCACAGAA
ATGAAACAGATGCACGAATGGAATTTTACAGCCTCTTCCATAAAGGGAAT
AAGCCTATCAAAGTTTGATGAAAGGTGTTGTTTTCTTTATGTCCATGATA
ATTCTGATGACTTTCAAATCTACTTTTCCACCGAAGAGCAGTGCAGTAGA
TTTTTCTCTTTGGTCAAAGAGATGATAACCAATACAGCAGGCAGTACGGT
GGAGCTGGAGGGAGAGACCGATGGAGACACCTTGGAGTATGAGTATGACC

-continued

ATGATGCAAATGGTGAGAGAGTTGTCTTGGGGAAAGGCACGTATGGGATT
GTGTATGCTGGCCGAGATCTGAGCAATCAAGTGCGAATAGCCATCAAAGA
AATCCCGGAGAGAGATAGCAGGTATTCTCAGCCTCTGCACGAGGAGATAG
CCCTGCACAAGTACCTTAAGCACCGCAATATCGTTCAGTACCTGGGCTCT
GTTCAGAGAACGGCTACATTAAGATATTTATGGAGCAGGTGCCTGGAGGA
AGCCTTTCTGCTCTTCTGCGATCCAAATGGGGGCCGATGAAGGAACCGAC
AATCACGTTTTACACCAAACAGATCCTGGAGGGCCTTAAGTATCTTCATG
AAAACCAGATCGTGCACAGAGACATAAAGGGCGATAATGTTCTGGTGAAC
ACCTACAGCGGAGTGGTGAAAATCTCCGATTTTGGAACCTCGAAACGTCT
TGCGGGTGTGAACCCCTGCACAGAGACTTTTACTGGCACCCTGCAGTACA
TGGCAGGTGAGATAATTGACCAAGGGCCTCGCGGATATGGTGCCCCAGCC
GATATCTGGTCCCTGGGCTGCACCATCATTGAGATGGCCACCAGCAAGCC
TCCGTTCCATGAGCTTGGTGAGCCGCAGGCAGCCATGTTCAAAGTGGGCA
TGTTTAAGATCCACCCTGAGATTCCAGAAGCCCTTTCAGCTGAAGCCCGA
GCCTTCATTTTATCCTGTTTCGAGCCTGACCCCCACAAACGTGCCACCAC
TGCTGAGTTACTGAGAGAGGGTTTCTTAAGGCAGGTGAACAAGGGCAAGA
AGAACCGAATTGCCTTCAAGCCCTCAGAAGGTCCCCGCGGTGTCGTCCTG
GCCCTGCCCACACAGGGAGAGCCCATGGCCACCAGCAGCAGCGAGCACGG
CTCTGTCTCCCCAGACTCCGACGCCCAGCCTGACGCACTCTTTGAGAGGA
CCCGGGCGCCCAGGCACCACCTTGGCCACCTCCTCAGTGTTCCAGACGAG
AGCTCAGCCTTGGAAGACCGGGGCTTGGCCTCGTCCCCGGAGGACAGGGA
CCAGGGCCTCTTCCTGCTACGCAAGGACAGTGAGCGCCGTGCCATCCTGT
ACAAAATCCTCTGGGAGGAGCAGAACCAGGTGGCTTCCAACCTGCAGGAG
TGTGTGGCCCAGAGTTCCGAAGAGTTGCATCTCTCAGTTGGACACATCAA
GCAAATCATTGGGATCCTGAGGGACTTCATCCGCTCCCCAGAGCACCGGG
TGATGGCGACCACAATATCAAAGCTCAAGGTGGACCTGGACTTTGACAGC
TCGTCCATCAGTCAGATTCACCTGGTGCTGTTCGGATTTCAGGATGCCGT
AAATAAAATTTTGAGGAACCACTTAATTAGGCCCCACTGGATGTTCGCGA
TGGACAACATCATCCGCCGAGCGGTGCAGGCCGCGGTCACCATTCTCATC
CCAGAGCTCCGAGCCCACTTTGAGCCTACCTGTGAGACTGAAGGGGTACA
TAAGGACATGGATGAAGCGGAAGAGGGCTATCCCCCAGCCACCGGACCTG
GCCAGGAGGCCCAGCCCCACCAGCAGCACCTGAGCCTCCAGCTGGGTGAG
CTCAGACAGGAGACCAACAGACTTTTGGAACACCTAGTTGAAAAAGAGAG
AGAGTACCAGAATCTTCTGCGGCAAACTCTAGAACAGAAAACTCAAGAAT
TGTATCACCTTCAGTTAAAATTAAAATCGAATTGTATTACAGAGAACCCA
GCAGGCCCCTACGGGCAGAGAACAGATAAAGAGCTTATAGACTGGTTGCG
GCTGCAAGGAGCTGATGCAAAGACAATTGAAAAGATTGTTGAAGAGGGTT
ATACACTTTCGGATATTCTTAATGAGATCACTAAGGAAGATCTAAGATAC
CTCCGACTACGGGGTGGTCTCCTCTGCAGACTCTGGAGTGCGGTCTCCCA
GTACAGAAGGGCTCAGGAGGCCTCAGAAACCAAAGACAAGGCTTGATACC

-continued

AATCAGCTAAGCTGTGGCAGAGTGTCCCACCACGCTACATGTTTTGTTAA

AGCTTCTGTTAGTGTATACACGAATTCCGCTGTGTTTACATATTTAAAAA

TGCCATTGTTCAATTAATAGTTTAAGAACTTGTTTTAAATACTGTCCTGA

GTTTCTTTTGAAACCTGTTATTTATAAACATAGAACTGTGTGTATTGTGA

-continued

AAACAGTGAGCCTTGGTTTTGACCTCCCGGAATATTAGGAAATTCACTTG

TAGTCCCAGCTATGCAGGAGGCTGAGGTGGGAGGATTGCTTGAGCCCAGG

AGGTGTGGAGGCTGCAGTGAGCCATGATCACACCA

SEQ ID NO:2 Human ASKRK Polypeptide Sequence

The kinase domain is underlined; K681 is indicated in bold.

[ 1 MESGGGNAPA GALGAASESP QCPPPPGVEG AAGPAEPDGA AEGAAGGSGE

51 GESGGGPRRA LRAVYVRSES SQGGAAGGPE AGARQCLLRA CEAEGAHLTS

101 VPFGELDFGE TAVLDAFYDA DVAVVDMSDV SRQPSLFYHL GVRESNDMAN

151 NVILYHDTDA DTALSLKDMV TQKNTASSGN YYFIPYIVTP CTDYNCCESD

201 AQRRASEYMQ PNWDNILGPL CMPLVDRFIS LLKDIHVTSC VYYKETLLND

251 IRKAREKYQG EELAKELARI KLRMDNTEVL TSDIIINLLL SYRDIQDYDA

301 MVKLVETLEM LPTCDLADQH NTKFHYANAL NRRNSTGDRE KALQIMLQVL

351 QSCDHPGPDM FCLCGRIYKD IFLDSDCKDD TSRDSAIEWY RKGNELQSSL

401 YSGINLAVLL IVAGQQNETS LELRKIGVRL NSLLGRKGSL EKMNNYWDVG

451 QFFSVSMLAH DVGKAVQAAE RLFKLKPPVW YLRSLVQNLL LIRRFKKTII

501 EHSPRQERLN FWLDIINEAT NEVTNGLRNP VLVIEPTKVY QPSYVSINNE

551 AEERTVSLWH VSPTEMKQMH EWNNTASSIK GISLSKNDER CCNLYVHDNS

601 DDNQIYNSTE EQCSRNFSLV KEMITNTAGS TVELEGETDG DTLEYEYDHD

651 ANGERVVLGK GTYGIVYAGR DLSNQVRIAI KEIPERDSRY SQPLHEEIAL

701 HKYLKHRNIV QYLGSVSENG YIKINMEQVP GGSLSALLRS KWGPMKEPTI

751 KNYTKQILEG LKYLHENQIV HRDIKGDNVL VNTYSGVVKI SDNGTSKRLA

801 GVNPCTETNT GTLQYMAPEI IDQGORGYGA PADIWSLGCT IIEMATSKPP

851 FHELGEPQAA MFKVGMNKIH PEIPEALSAE ARAFILSCFE PDPHKRATTA

901 ELLREGFLRQ VNKGKKNRIA FKPSEGPRGV VLALPTQGEP MATSSSEHGS

951 VSPDSDAQPD ALNERTRAPR HHLGHLLSVP DESSALEDRG LASSPEDRDQ

1001 GLFLLRKDSE RRAILYKILW EEQNQVASNL QECVAQSSEE LHLSVGHIKQ

1051 IIGILRDFIR SPEHEVMATT ISKLKVDLDN DSSSISQIHL VLFGNQDAVN

1101 KILRNHLIRP HWMFAMDNII RRAVQAAVTI LIPELRAHNE PTCETEGVDK

1151 DMDEAEEGYP PATGPGQEAQ PHQQHLSLQL GELRQETNRL LEHLVEKERE

1201 YQNLLRQTLE QKTQELYHLQ LKLKSNCITE NPAGPYGQRT DKELIDWLRL

1251 QGADAKTIEK IVEEGYTLSD ILNEITKEDL RYLRLRGGLL CRLWSAVSQY

1301 RRAQEASETK DKA]

*1 MESGGGNAPA GALGAASESP QCPPPPGVEG AAGPAEPDGA AEGAAGGSGE*

*51 GESGGGPRRA LRAVYVRSES SQGGAAGGPE AGARQCLLRA CEAEGAHLTS*

*101 VPFGELDFGE TAVLDAFYDA DVAVVDMSDV SRQPSLFYHL GVRESFDMAN*

*151 NVILYHDTDA DTALSLKDMV TQKNTASSGN YYFIPYIVTP CTDYFCCESD*

*201 AQRRASEYMQ PNWDNILGPL CMPLVDRFIS LLKDIHVTSC VYYKETLLND*

*251 IRKAREKYQG EELAKELARI KLRMDNTEVL TSDIIINLLL SYRDIQDYDA*

-continued

```
 301 MVKLVETLEM LPTCDLADQH NTKFHYAFAL NRRNSTGDRE KALQIMLQVL
 351 QSCDHPGPDM FCLCGRIYKD IFLDSDCKDD TSRDSAIEWY RKGFELQSSL
 401 YSGINLAVLL IVAGQQFETS LELRKIGVRL NSLLGRKGSL EKMNNYWDVG
 451 QFFSVSMLAH DVGKAVQAAE RLFKLKPPVW YLRSLVQNLL LIRRFKKTII
 501 EHSPRQERLN FWLDIIFEAT NEVTNGLRFP VLVIEPTKVY QPSYVSINNE
 551 AEERTVSLWH VSPTEMKQMH EWNFTASSIK GISLSKFDER CCFLYVHDNS
 601 DDFQIYNSTE EQCSRFFSLV KEMITNTAGS TVELEGETDG DTLEYEYDHD
 651 ANGERVVLGK GTYGIVYAGR DLSNQVRIAI KEIPERDSRY SQPLHEEIAL
 701 HKYLKHRNIV QYLGSVSENG YIKIFMEQVP GGSLSALLRS KWGPMKEPTI
 751 KFYTKQILEG LKYLHENQIV HRDIKGDNVL VNTYSGVVKI SDFGTSKRLA
 801 GVNPCTETFT GTLQYMAPEI IDQGORGYGA PADIWSLGCT IIEMATSKPP
 851 FHELGEPQAA MFKVGMFKIH PEIPEALSAE ARAFILSCFE PDPHKRATTA
 901 ELLREGFLRQ VNKGKKNRIA FKPSEGPRGV VLALPTQGEP MATSSSEHGS
 951 VSPDSDAQPD ALFERTRAPR HHLGHLLSVP DESSALEDRG LASSPEDRDQ
1001 GLFLLRKDSE RRAILYKILW EEQNQVASNL QECVAQSSEE LHLSVGHIKQ
1051 IIGILRDFIR SPEHEVMATT ISKLKVDLDF DSSSISQIHL VLFGNQDAVN
1101 KILRNHLIRP HWMFAMDNII RRAVQAAVTI LIPELRAHNE PTCETEGVDK
1151 DMDEAEEGYP PATGPGQEAQ PHQQHLSLQL GELRQETNRL LEHLVEKERE
1201 YQNLLRQTLE QKTQELYHLQ LKLKSNCITE NPAGPYGQRT DKELIDWLRL
1251 QGADAKTIEK IVEEGYTLSD ILNEITKEDL RYLRLRGGLL CRLWSAVSQY
1301 RRAQEASETK DKA
```

SEQ ID NO:3 Partial Mouse ASKRK Nucleic Acid

```
   1 GCCGAGGGCG GGCGCGGGCC ACGCCGGGCT CTGCGGGCTG TCTACGTGCG
  51 CAGCGAAAGT TCGCAGGGGG CAGCCGCCGG CGGCGGCCCC CACCCCGGGG
 101 CGCTCAAGTG CTTGCTTCGG GCTTGCGAAG CCGAGGGCGC CCACCTCACC
 151 TCCGTCCCCT TCGGGGAGCT CGACTTCGGG GAGACGGCCG TGCTCGATGC
 201 CTTCTACGAT GCAGATGTTG CCATTGTGGA CATGAGTGAT ATCTCCAGAC
 251 AGCCTTCCCT TTTCTACCAT CTTGGAGTCC GAGAGAGTTT TGACATGGCT
 301 AACAATGTAA TTCTCTACTA TGATACTGAT GCTGACACTG CTCTGTCATT
 351 GAAGGATATG GTCACTCAAA AAAACACAGC ATGGAGTGGA AATTATTATT
 401 TTATCCCCTA CACTGTGACA CCATGTGCTG ACTATTTTTG CTGTGAGAGT
 451 GATGCCCAAA GGAGAGCCTC AGAGTACATG CAGCCTAACT GGGACACCAT
 501 ACTGGGCCCG CTGTGTATGC CCCTGGTCGA CAGGTTCACT AGCCTCCTTA
 551 AGGACATCCG TGTGACTTCA TGTGCTTATT ATAAAGAAAC ATTGTTAAAT
 601 GACATCCGGA AAGCCAGAGA GAAATACCAA GGTGATGAAC TGGCGAAAGA
 651 GTTGACTCGG ATCAAATTCC GTATGGATAA CATTGAGGTT CTGACATCAG
 701 ACATCATCAT TAACTTACTT CTGTCCTACC GTGATATCCA GGACTACGAT
 751 GCAATGGTCA AGCTGGTAGA GACACTGAAG ATGCTGCCAA CGTGTGATTT
```

-continued

```
 801 GGCTGATCAG CACAACATTA AATTTCACTA TGCATTTGCA CTGAATAGGA
 851 GAAACAGCAC AGGTGACCGT GAAAAGGCTC TTCAGGTTAT GCTCCAAGTT
 901 CTGCAAAGCT GTGACCACCC AGCTCCTGAC ATGTTTTGCC TGTGTGGGCG
 951 GATATACAAG GACATCTTCC TGGATTCAGG TTGTGAAGAG GATGCAAGCA
1001 GAGACAGTGC CATTGAGTGG TATCGCAAAG GGTTTGAACT CCAGTCATCC
1051 CTTTATTCAG GAATTAACCT TGCAGTTTTG CTGATAGTTT CTGGACAACA
1101 GTTTGAAACT TCGATGGAAC TAAGGAAAAT AGGTGTCCGG CTGAACAGTT
1151 TATTGGGAAG AAAAGGGAGC CTGGAGAAAA TGAACAATTA CTGGGATGTA
1201 GGTCAGTTCT TCACCGTCAG CATGCTGGCA AGTGATATTG GGAAAGCTGT
1251 CCAGGCAGCA GAGAGGTTGT TCAAACTGAA ACCCCCAGTC TGGTACCTGC
1301 GGTCATTAGT TCAGAACTTG CTGTTAATTC AACGCTTCAA GAAACCCATT
1351 ACAGAACATT CACCCAGGCA GGAACGGCTT AACTTCTGGT TAGATATCAT
1401 TTTTGAAGCA ACGAATGAAG TTACTAATGG ACTGAGATTT CCAGTTCTGG
1451 TAATAGAGCC AACCAAAGTC TACCAGCCTT CTTATGTTTC TATCAACAAT
1501 GAAGCTGAAG AAAGAACTGT TTCTTTATGG CATGTCTCAC CCACAGAAAT
1551 GAAACAAATC CATGAGTGGA ATTTTACAGC CTCTTCTATT AAACGAATAA
1601 GCCTATCCAA GTTTGATGAA CGGTGCTGTT TTCTTTATGT CCATGATAAT
1651 TCTGATGACT TTCAAATCTA CTTTTCCACC GAACAGGAGT GTAATAGATT
1701 TTGTTCTTTG GTCAAAGAGA TGCTAAACAA TGGAGTGGGC AGTACAGTGG
1751 AGTTGGAGGG AGAGGCTGAT GGAGACACCT TAGAGTATGA GTATGACCAT
1801 GATGCGAATG GGGAGAGAGT TGTCTTGGGG AAAGGCTCCT ATGGGATTGT
1851 GTATGCCGGC CGTGATCTCA GTAATCAAGT ACGGATAGCC ATCAAGGAAA
1901 TCCCAGAGAG AGATATCAGG TACTCTCAGC CTCTGCATGA AGAAATAGCT
1951 CTGCACAAGT ATCTCAAACA TCGCAACATC CTGGAGTACC TTGGCTCTGT
2001 TTCAGAGAAT GGCTACATTA AGATATTTAT GGAGCAGGTG CCTGGAGGAA
2051 GCCTTTCTGC TCTCTTACGA TCTAAATGGG CAGGTATGAA GGAACCCACT
2101 ATCAAGTTTT ATACCAAACA GATCCTGGAA GGCCTGAAGT ATCTCCATGA
2151 AAACCAGATA GTGCACAGAG ACATAAAGGG AGATAATGTT CTGGTGAACA
2201 CCTATAGTGG AGTGGTAAAA ATCTCTGATT TTGGAACCTC TAAACGCCTC
2251 GCAGGAATTA ACCCATGCAC CGAGACCTTT ACAGGAACTC TGCAGTACAT
2301 GGCACCTGAG ATTATTGATC AAGGACCTCG GGGATATGGT GCTCCAGCTG
2351 ATATCTGGTC CTTGGGCTGC ACCATCATTG AGATGGCAAC CAGCAGGCCT
2401 CCATTCCATG AGCTTGGTGA GCCCCAAGCA GCCATGTTTA AGGTAGGGAT
2451 GTTTAAGATC CACCCTGAAA TTCCAGAGGC CCTTTCAGCT GAAGCCAGAG
2501 CCTTCATCTT GTCTTGTTTT GAGCCTGACC CTCAGAAACG TGTCACTGCT
2551 GCTGACCTTC TCCAAGAAGG GTTCTTAAGG CAGGTGAACA AAGGCAAAAA
2601 GAACCGAATT GCTTTCAAGC CTTCAGAGGG TGTTCGGAGT GGCACTGGTA
2651 CTCTGGCTCT GCCTTCATCA GGAGAGCTTG TGGGCAGCAG CAGCAGCGAG
2701 CATGGCTCAA TCTCCCCACA CTCGGATGCC CAGCCTGATG CATTCTTTGA
2751 GAAAGTCCAG GTGCCCAAAC ATCAGCTCAG CCACCTTCTC AGTGTCCCAG
```

-continued

```
2801 ATGAAAGCCC AGCCTTAGAT GACCGAAGCA CAGCCTTACC CCCAGAGGAG
2851 AGGGACCCTG CTGTCTTTCT GCTGCGCAAG GACAGTGAGC GCAGAGCCAT
2901 CCTTTACAGA ATCCTTTGGG AGGAACAGAA CCAAGTGGCT TCCAACTTGC
2951 AAGAGTGTGT GGTCCAGAGT TCAGAAGAGT TGCTTCTCTC AGTTAGCCAC
3001 ATCAAACAGA TAATTGGAAT CCTGAGGGAC TTCATCCGCT CCCCAGAGCA
3051 CAGGGTGATG GCAGCCACAA TATCAAAACT AAAGGTGGAC CTGGACTTTG
3101 ACAGCTCATC CATCAACCAG ATTCACCTGA TTCTGTTTGG GTTCCAAGAT
3151 GCTGTCAATA GAATTTTGAG AAACCACTTA ATTAGGCCCC ACTGGATGTT
3201 TGCAATGGAC AACATCATTC GCAGAGCTGT GCAGGCTGCA CTCACCATTC
3251 TCATTCCAGA GCTCCAAGCC CACTTTGAGC CTGCTTCTGA GACTGAAGGG
3301 GTAGACAAGG ACACAGAAGT AGAAGGGGAC TATCCCCTAG TAGACCTCCT
3351 CAGCCAAGAA GTGCATGTGA CACCTAGAGG CACCAGACCT GGCTCAGTGG
3401 CTATCCAGGA CGGCCAGCCC CACCAGCAAG ACCCAAGTCT CCAACTGAGC
3451 AAGCTCAGGC AAGAGACCAA CAGACTTTGG GAACACCTAG TTCAAAAAGA
3501 GAAGGGAGTA CCAGAATCTT CTTCGAATAA TTCTAGACCA GAAAACTCAA
3551 GAATTGTATC AGGTTCAGTT ACAGTACAAA TCCAATGGTG GTACAGAGAA
3601 CCCTCCACCC CTGATGGACT GGGAACCGAC AGAGAGCTTA TAGACTGGTT
3651 GCAACTACAA GGAGTGGATG CCAATACAAT AGAAAAGATT GTTGAAGAGG
3701 ACTATACACT TTCTGATATT CTCAATGATA TCACTAAGGA AGACCTAAGG
3751 TGCCTCCGAC TACGGGGTGG TGTCCTCTGT AGGCTCTGGC ATGCAGTCTC
3801 CCAGCACAGA AGACAAATGC AGGAGTCTTC ACAGTGAGCC AAGCCTGGGG
3851 AGAATGGGCA AAAAGTCCCC TACACCTGCT CATGATTAAA GCTTCTGTTG
3901 GCGTACTCGC AAACTCCGAG TTTCCACAGA AAGACCCTTG TCCATTTAAT
3951 TCAAGCACGT GTGATTGTAG AGCATCCTTG TTTATAAACA AGATTGTAAG
4001 TAATGTCAGC CCTGACCTAA TATTTAAAAA GTCAGCATAT CGCTGGAAAG
4051 ATAAAGCATA CGTATTTTAT AAACTAGTGT AATTACTTAA ATGTGAAAGG
4101 TTAAAAAGTG TGCCTTGCAA TGGGAGTACA GTTTCATGTA TGTTAAATGT
4151 CTAAATGGAA AAAATTAAAC TATTTTACCT TTAAAAAAAA AAAAAAAAAA
4201 ACTCGACGAG CTCACTAGTC G
```

SEQ ID NO:4 Partial Mouse ASKRK Polypeptide Sequence
The kinase domain is underlined.

```
  1 AEGGRGPRRA LPAVYVRSES SQGAAAGGGP EAGALKCLLR ACEAEGAHLT
 51 SVPFGELDFG ETAVLDAFYD ADVAIVDMSD ISRQPSLFYH LGVRESFDMA
101 NNVILYYDTD ADTALSLKDM VTQKNTASSG NYYFIPYTVT PCADYFCCES
151 DAQRRASEYM QPNWDTILGP LCMPLVDRFT SLLKDIRVTS CAYYKEYLLN
201 DIRKAREKYQ GDELAKELTR IKFRMDNIEV LTSDIIINLL LSYRDIQDYD
251 AMVKLVETLK MLPTCDLADQ HNIKFHYAFA LNRRNSTGDR EKALQVMLQV
301 LQSCDHPAPD MFCLCGRIYK DIFLDSGCEE DASRDSAIEW YRKGFELQSS
351 LYSGINLAVL LIVSGQQFET SMELRKIGVR LNSLLGRKGS LEKMNNYWDV
```

-continued

```
 401 GQFFTVSMLA SDIGKAVQAA ERLFKLKPPV WYLRSLVQNL LLIQRFKKPI

 451 TEHSPRQERL NFWLDIIFEA TNEVTNGLRF PVLVIEPTKV YQPSYVSINN

 501 EAEERTVSLQ HVSPTEMKQI HEWNFTASSI KGISLSKFDE RCCFLYVHDN

 551 SDDFQIYFST EDQCNRFCSL VKEMLNNGVG STVELEGEAD GDTLEYEYDH

 601 DANGERVVLG KGSYGIVYAG RDLSNQVRIA IKEIPERDIR YSQPLHEEIA

 651 LHKYLKHRNI VQYLGSVSEN GYIKIFMEQV PGGSLSALLR SKWGPMKEPT

 701 IKFYTKQILE GLKYLHENQI VHRDIKGDNV LVNTYSGVVK ISDEGTSKRL

 751 AGINPCTETF TGTLQYMAPE IIDQGPRGYG APADIWSLGC TIIEMATSRP

 801 PFHELGEPQA AMFKNGMFKI HPEIPEALSA EARAFILSCF EPDPQKRVTA

 851 ADLLQEGFLR QVNKGKKNRI AFKPSEGVRS GTGTLALPSS GELVGSSSSE

 901 HGSISPDSDA QPDAFFEKVQ VPKHQLSHLL SVPDESPALD DRSTALPPEE

 951 RDPGLFLLTK DSERRAILYR ILWEEQNQVA SNLQECVVQS SEELLLSVSH

1001 IKQIIGILRD FIRSPEHRVM AATISKLKVD LDFDSSSINQ IHLILFGFQD

1051 AVNRILRNHL IRPHWNFAMD NIIRRAVQAA VTILIPELQA HFEPASETEG

1101 VDKDTEVEGD YPLVDLLSQE VHVTPRGTRP GSVAIQEGQP HQQDPSLQLS

1151 KLRQETNRLW EHLVQKEKGV PESSSPNSRP ENSRIVSOSV TVQIQWWYRE

1201 PSTPDGLGTD RELIDWLQLQ GVDANTIEKI VEEDYTLSDI LNDITKEDLR

1251 CLRLRGGVLC RLWHAVSQHR RQMQESSQ
```

---

SEQUENCE LISTING

```
<160> NUMBER OF SEQ ID NOS: 10

<210> SEQ ID NO 1
<211> LENGTH: 4281
<212> TYPE: DNA
<213> ORGANISM: Homo sapiens
<220> FEATURE:
<223> OTHER INFORMATION: human apoptosis signal regulating kinase
      related kinase (ASKRK)
<220> FEATURE:
<221> NAME/KEY: CDS
<222> LOCATION: (1)..(3942)
<223> OTHER INFORMATION: human ASKRK

<400> SEQUENCE: 1

atg gag agc ggc ggt ggg aat gct ccg gcc ggg gcc ctc ggg gcg gcg       48
Met Glu Ser Gly Gly Gly Asn Ala Pro Ala Gly Ala Leu Gly Ala Ala
  1               5                  10                  15

agc gag tcc cct cag tgc ccg ccg ccg ccg ggg gtg gag ggc gcg gcc       96
Ser Glu Ser Pro Gln Cys Pro Pro Pro Pro Gly Val Glu Gly Ala Ala
             20                  25                  30

ggg ccg gcg gag ccc gac ggg gcg gcg gag ggc gcg gca ggc ggc agc      144
Gly Pro Ala Glu Pro Asp Gly Ala Ala Glu Gly Ala Ala Gly Gly Ser
         35                  40                  45

ggc gag ggc gag agt ggg ggc ggg ccg cgg cgg gct ctg cgg gca gta      192
Gly Glu Gly Glu Ser Gly Gly Gly Pro Arg Arg Ala Leu Arg Ala Val
     50                  55                  60

tac gtg cgc agt gag agc tcc cag ggc ggc gcg gcc ggc ggc ccg gag      240
Tyr Val Arg Ser Glu Ser Ser Gln Gly Gly Ala Ala Gly Gly Pro Glu
 65                  70                  75                  80
```

-continued

```
gct ggg gcg cgg cag tgc ctg ctg cgg gcc tgc gag gcc gag ggc gct      288
Ala Gly Ala Arg Gln Cys Leu Leu Arg Ala Cys Glu Ala Glu Gly Ala
                 85                  90                  95

cac ctc acc tcc gtg ccc ttc ggg gag ctg gac ttc ggg gag acg gcc      336
His Leu Thr Ser Val Pro Phe Gly Glu Leu Asp Phe Gly Glu Thr Ala
            100                 105                 110

gtg ctc gac gcc ttc tac gac gca gat gtt gct gtg gta gac atg agc      384
Val Leu Asp Ala Phe Tyr Asp Ala Asp Val Ala Val Val Asp Met Ser
        115                 120                 125

gat gtc tcc aga cag cct tcc ctc ttc tac cat ctt gga gtc cga gaa      432
Asp Val Ser Arg Gln Pro Ser Leu Phe Tyr His Leu Gly Val Arg Glu
    130                 135                 140

agc ttt gac atg gcc aat aat gtg atc ttg tac cat gac acc gat gcc      480
Ser Phe Asp Met Ala Asn Asn Val Ile Leu Tyr His Asp Thr Asp Ala
145                 150                 155                 160

gac act gct ctc tct ttg aag gac atg gta act caa aaa aac aca gca      528
Asp Thr Ala Leu Ser Leu Lys Asp Met Val Thr Gln Lys Asn Thr Ala
                165                 170                 175

tcc agt gga aat tat tat ttc atc cca tac atc gtg aca ccg tgc act      576
Ser Ser Gly Asn Tyr Tyr Phe Ile Pro Tyr Ile Val Thr Pro Cys Thr
            180                 185                 190

gat tat ttt tgc tgc gag agt gat gcc cag aga cga gcc tcc gag tac      624
Asp Tyr Phe Cys Cys Glu Ser Asp Ala Gln Arg Arg Ala Ser Glu Tyr
        195                 200                 205

atg cag ccc aac tgg gac aac atc ctg ggc ccg ctg tgc atg cct ttg      672
Met Gln Pro Asn Trp Asp Asn Ile Leu Gly Pro Leu Cys Met Pro Leu
    210                 215                 220

gtg gac agg ttc att agc ctc ctt aag gac atc cac gtg acc tca tgt      720
Val Asp Arg Phe Ile Ser Leu Leu Lys Asp Ile His Val Thr Ser Cys
225                 230                 235                 240

gtt tat tac aaa gaa acc ttg tta aat gac atc cgg aaa gcc aga gag      768
Val Tyr Tyr Lys Glu Thr Leu Leu Asn Asp Ile Arg Lys Ala Arg Glu
                245                 250                 255

aaa tac caa ggt gag gaa ctg gcg aag gag cta gct cgg atc aag ctc      816
Lys Tyr Gln Gly Glu Glu Leu Ala Lys Glu Leu Ala Arg Ile Lys Leu
            260                 265                 270

cgc atg gat aat act gag gtt ctg acc tca gac atc atc att aac tta      864
Arg Met Asp Asn Thr Glu Val Leu Thr Ser Asp Ile Ile Ile Asn Leu
        275                 280                 285

ctc ctg tcc tac cgt gat atc cag gac tat gat gcg atg gtg aag ctg      912
Leu Leu Ser Tyr Arg Asp Ile Gln Asp Tyr Asp Ala Met Val Lys Leu
    290                 295                 300

gtg gaa aca ctg gag atg ctg cct acg tgt gat ttg gcc gat cag cat      960
Val Glu Thr Leu Glu Met Leu Pro Thr Cys Asp Leu Ala Asp Gln His
305                 310                 315                 320

aac act aaa ttc cac tat gcg ttt gca ctg aat agg aga aac agc aca     1008
Asn Thr Lys Phe His Tyr Ala Phe Ala Leu Asn Arg Arg Asn Ser Thr
                325                 330                 335

ggt gac cgt gag aag gct ctg cag atc atg ctc cag gtt ctg cag agc     1056
Gly Asp Arg Glu Lys Ala Leu Gln Ile Met Leu Gln Val Leu Gln Ser
            340                 345                 350

tgt gat cac ccg ggc ccc gac atg ttc tgc ctg tgt ggg agg atc tac     1104
Cys Asp His Pro Gly Pro Asp Met Phe Cys Leu Cys Gly Arg Ile Tyr
        355                 360                 365

aag gac atc ttc ttg gat tca gac tgc aaa gat gac acc agc cgc gac     1152
Lys Asp Ile Phe Leu Asp Ser Asp Cys Lys Asp Asp Thr Ser Arg Asp
    370                 375                 380

agc gcc att gag tgg tat cgc aaa ggg ttt gaa ctc cag tca tcc ctc     1200
Ser Ala Ile Glu Trp Tyr Arg Lys Gly Phe Glu Leu Gln Ser Ser Leu
385                 390                 395                 400
```

-continued

```
tat tcg gga att aat ctt gca gtt ttg ctg att gtt gct gga caa caa     1248
Tyr Ser Gly Ile Asn Leu Ala Val Leu Leu Ile Val Ala Gly Gln Gln
                405                 410                 415

ttt gaa act tcc ttg gaa cta agg aaa ata ggt gtc cgg ctg aac agt     1296
Phe Glu Thr Ser Leu Glu Leu Arg Lys Ile Gly Val Arg Leu Asn Ser
            420                 425                 430

ttg ttg gga aga aaa ggg agc ttg gag aaa atg aac aat tac tgg gat     1344
Leu Leu Gly Arg Lys Gly Ser Leu Glu Lys Met Asn Asn Tyr Trp Asp
        435                 440                 445

gtg ggt cag ttc ttc agc gtc agc atg ctg gcc cat gat gtc ggg aaa     1392
Val Gly Gln Phe Phe Ser Val Ser Met Leu Ala His Asp Val Gly Lys
    450                 455                 460

gcc gtc cag gca gca gag agg ttg ttc aaa ctg aaa cct cca gtc tgg     1440
Ala Val Gln Ala Ala Glu Arg Leu Phe Lys Leu Lys Pro Pro Val Trp
465                 470                 475                 480

tac ctg cga tca tta gtt cag aac ttg tta cta att cgg cgc ttc aag     1488
Tyr Leu Arg Ser Leu Val Gln Asn Leu Leu Leu Ile Arg Arg Phe Lys
                485                 490                 495

aaa acc att att gaa cac tcg ccc agg caa gag cgg ctg aac ttc tgg     1536
Lys Thr Ile Ile Glu His Ser Pro Arg Gln Glu Arg Leu Asn Phe Trp
            500                 505                 510

tta gat ata att ttt gag gca aca aat gaa gtc act aat gga ctc aga     1584
Leu Asp Ile Ile Phe Glu Ala Thr Asn Glu Val Thr Asn Gly Leu Arg
        515                 520                 525

ttt cca gtt ctg gtc ata gag cca acc aaa gtg tac cag cct tct tat     1632
Phe Pro Val Leu Val Ile Glu Pro Thr Lys Val Tyr Gln Pro Ser Tyr
    530                 535                 540

gtt tcc ata aac aat gaa gcc gag gag aga aca gtt tct tta tgg cat     1680
Val Ser Ile Asn Asn Glu Ala Glu Glu Arg Thr Val Ser Leu Trp His
545                 550                 555                 560

gtc tca ccc aca gaa atg aaa cag atg cac gaa tgg aat ttt aca gcc     1728
Val Ser Pro Thr Glu Met Lys Gln Met His Glu Trp Asn Phe Thr Ala
                565                 570                 575

tct tcc ata aag gga ata agc cta tca aag ttt gat gaa agg tgt tgt     1776
Ser Ser Ile Lys Gly Ile Ser Leu Ser Lys Phe Asp Glu Arg Cys Cys
            580                 585                 590

ttt ctt tat gtc cat gat aat tct gat gac ttt caa atc tac ttt tcc     1824
Phe Leu Tyr Val His Asp Asn Ser Asp Asp Phe Gln Ile Tyr Phe Ser
        595                 600                 605

acc gaa gag cag tgc agt aga ttt ttc tct ttg gtc aaa gag atg ata     1872
Thr Glu Glu Gln Cys Ser Arg Phe Phe Ser Leu Val Lys Glu Met Ile
    610                 615                 620

acc aat aca gca ggc agt acg gtg gag ctg gag gga gag acc gat gga     1920
Thr Asn Thr Ala Gly Ser Thr Val Glu Leu Glu Gly Glu Thr Asp Gly
625                 630                 635                 640

gac acc ttg gag tat gag tat gac cat gat gca aat ggt gag aga gtt     1968
Asp Thr Leu Glu Tyr Glu Tyr Asp His Asp Ala Asn Gly Glu Arg Val
                645                 650                 655

gtc ttg ggg aaa ggc acg tat ggg att gtg tat gct ggc cga gat ctg     2016
Val Leu Gly Lys Gly Thr Tyr Gly Ile Val Tyr Ala Gly Arg Asp Leu
            660                 665                 670

agc aat caa gtg cga ata gcc atc aaa gaa atc ccg gag aga gat agc     2064
Ser Asn Gln Val Arg Ile Ala Ile Lys Glu Ile Pro Glu Arg Asp Ser
        675                 680                 685

agg tat tct cag cct ctg cac gag gag ata gcc ctg cac aag tac ctt     2112
Arg Tyr Ser Gln Pro Leu His Glu Glu Ile Ala Leu His Lys Tyr Leu
    690                 695                 700

aag cac cgc aat atc gtt cag tac ctg ggc tct gtt tca gag aac ggc     2160
Lys His Arg Asn Ile Val Gln Tyr Leu Gly Ser Val Ser Glu Asn Gly
```

-continued

```
705                 710                 715                 720

tac att aag ata ttt atg gag cag gtg cct gga gga agc ctt tct gct     2208
Tyr Ile Lys Ile Phe Met Glu Gln Val Pro Gly Gly Ser Leu Ser Ala
                725                 730                 735

ctt ctg cga tcc aaa tgg ggg ccg atg aag gaa ccg aca atc aag ttt     2256
Leu Leu Arg Ser Lys Trp Gly Pro Met Lys Glu Pro Thr Ile Lys Phe
            740                 745                 750

tac acc aaa cag atc ctg gag ggc ctt aag tat ctt cat gaa aac cag     2304
Tyr Thr Lys Gln Ile Leu Glu Gly Leu Lys Tyr Leu His Glu Asn Gln
        755                 760                 765

atc gtg cac aga gac ata aag ggc gat aat gtt ctg gtg aac acc tac     2352
Ile Val His Arg Asp Ile Lys Gly Asp Asn Val Leu Val Asn Thr Tyr
    770                 775                 780

agc gga gtg gtg aaa atc tcc gat ttt gga acc tcg aaa cgt ctt gcg     2400
Ser Gly Val Val Lys Ile Ser Asp Phe Gly Thr Ser Lys Arg Leu Ala
785                 790                 795                 800

ggt gtg aac ccc tgc aca gag act ttt act ggc acc ctg cag tac atg     2448
Gly Val Asn Pro Cys Thr Glu Thr Phe Thr Gly Thr Leu Gln Tyr Met
                805                 810                 815

gca cct gag ata att gac caa ggg cct cgc gga tat ggt gcc cca gcc     2496
Ala Pro Glu Ile Ile Asp Gln Gly Pro Arg Gly Tyr Gly Ala Pro Ala
            820                 825                 830

gat atc tgg tcc ctg ggc tgc acc atc att gag atg gcc acc agc aag     2544
Asp Ile Trp Ser Leu Gly Cys Thr Ile Ile Glu Met Ala Thr Ser Lys
        835                 840                 845

cct ccg ttc cat gag ctt ggt gag ccg cag gca gcc atg ttc aaa gtg     2592
Pro Pro Phe His Glu Leu Gly Glu Pro Gln Ala Ala Met Phe Lys Val
    850                 855                 860

ggc atg ttt aag atc cac cct gag att cca gaa gcc ctt tca gct gaa     2640
Gly Met Phe Lys Ile His Pro Glu Ile Pro Glu Ala Leu Ser Ala Glu
865                 870                 875                 880

gcc cga gcc ttc att tta tcc tgt ttc gag cct gac ccc cac aaa cgt     2688
Ala Arg Ala Phe Ile Leu Ser Cys Phe Glu Pro Asp Pro His Lys Arg
                885                 890                 895

gcc acc act gct gag tta ctg aga gag ggt ttc tta agg cag gtg aac     2736
Ala Thr Thr Ala Glu Leu Leu Arg Glu Gly Phe Leu Arg Gln Val Asn
            900                 905                 910

aag ggc aag aag aac cga att gcc ttc aag ccc tca gaa ggt ccc cgc     2784
Lys Gly Lys Lys Asn Arg Ile Ala Phe Lys Pro Ser Glu Gly Pro Arg
        915                 920                 925

ggt gtc gtc ctg gcc ctg ccc aca cag gga gag ccc atg gcc acc agc     2832
Gly Val Val Leu Ala Leu Pro Thr Gln Gly Glu Pro Met Ala Thr Ser
    930                 935                 940

agc agc gag cac ggc tct gtc tcc cca gac tcc gac gcc cag cct gac     2880
Ser Ser Glu His Gly Ser Val Ser Pro Asp Ser Asp Ala Gln Pro Asp
945                 950                 955                 960

gca ctc ttt gag agg acc cgg gcg ccc agg cac cac ctt ggc cac ctc     2928
Ala Leu Phe Glu Arg Thr Arg Ala Pro Arg His His Leu Gly His Leu
                965                 970                 975

ctc agt gtt cca gac gag agc tca gcc ttg gaa gac cgg ggc ttg gcc     2976
Leu Ser Val Pro Asp Glu Ser Ser Ala Leu Glu Asp Arg Gly Leu Ala
            980                 985                 990

tcg tcc ccg gag gac agg gac cag ggc ctc ttc ctg cta cgc aag gac     3024
Ser Ser Pro Glu Asp Arg Asp Gln Gly Leu Phe Leu Leu Arg Lys Asp
        995                 1000                1005

agt gag cgc cgt gcc atc ctg tac aaa atc ctc tgg gag gag cag aac     3072
Ser Glu Arg Arg Ala Ile Leu Tyr Lys Ile Leu Trp Glu Glu Gln Asn
    1010                1015                1020

cag gtg gct tcc aac ctg cag gag tgt gtg gcc cag agt tcc gaa gag     3120
```

-continued

```
Gln Val Ala Ser Asn Leu Gln Glu Cys Val Ala Gln Ser Ser Glu Glu
1025                1030                1035                1040

ttg cat ctc tca gtt gga cac atc aag caa atc att ggg atc ctg agg     3168
Leu His Leu Ser Val Gly His Ile Lys Gln Ile Ile Gly Ile Leu Arg
                1045                1050                1055

gac ttc atc cgc tcc cca gag cac cgg gtg atg gcg acc aca ata tca     3216
Asp Phe Ile Arg Ser Pro Glu His Arg Val Met Ala Thr Thr Ile Ser
            1060                1065                1070

aag ctc aag gtg gac ctg gac ttt gac agc tcg tcc atc agt cag att     3264
Lys Leu Lys Val Asp Leu Asp Phe Asp Ser Ser Ser Ile Ser Gln Ile
        1075                1080                1085

cac ctg gtg ctg ttc gga ttt cag gat gcc gta aat aaa att ttg agg     3312
His Leu Val Leu Phe Gly Phe Gln Asp Ala Val Asn Lys Ile Leu Arg
    1090                1095                1100

aac cac tta att agg ccc cac tgg atg ttc gcg atg gac aac atc atc     3360
Asn His Leu Ile Arg Pro His Trp Met Phe Ala Met Asp Asn Ile Ile
1105                1110                1115                1120

cgc cga gcg gtg cag gcc gcg gtc acc att ctc atc cca gag ctc cga     3408
Arg Arg Ala Val Gln Ala Ala Val Thr Ile Leu Ile Pro Glu Leu Arg
                1125                1130                1135

gcc cac ttt gag cct acc tgt gag act gaa ggg gta gat aag gac atg     3456
Ala His Phe Glu Pro Thr Cys Glu Thr Glu Gly Val Asp Lys Asp Met
            1140                1145                1150

gat gaa gcg gaa gag ggc tat ccc cca gcc acc gga cct ggc cag gag     3504
Asp Glu Ala Glu Glu Gly Tyr Pro Pro Ala Thr Gly Pro Gly Gln Glu
        1155                1160                1165

gcc cag ccc cac cag cag cac ctg agc ctc cag ctg ggt gag ctc aga     3552
Ala Gln Pro His Gln Gln His Leu Ser Leu Gln Leu Gly Glu Leu Arg
    1170                1175                1180

cag gag acc aac aga ctt ttg gaa cac cta gtt gaa aaa gag aga gag     3600
Gln Glu Thr Asn Arg Leu Leu Glu His Leu Val Glu Lys Glu Arg Glu
1185                1190                1195                1200

tac cag aat ctt ctg cgg caa act cta gaa cag aaa act caa gaa ttg     3648
Tyr Gln Asn Leu Leu Arg Gln Thr Leu Glu Gln Lys Thr Gln Glu Leu
                1205                1210                1215

tat cac ctt cag tta aaa tta aaa tcg aat tgt att aca gag aac cca     3696
Tyr His Leu Gln Leu Lys Leu Lys Ser Asn Cys Ile Thr Glu Asn Pro
            1220                1225                1230

gca ggc ccc tac ggg cag aga aca gat aaa gag ctt ata gac tgg ttg     3744
Ala Gly Pro Tyr Gly Gln Arg Thr Asp Lys Glu Leu Ile Asp Trp Leu
        1235                1240                1245

cgg ctg caa gga gct gat gca aag aca att gaa aag att gtt gaa gag     3792
Arg Leu Gln Gly Ala Asp Ala Lys Thr Ile Glu Lys Ile Val Glu Glu
    1250                1255                1260

ggt tat aca ctt tcg gat att ctt aat gag atc act aag gaa gat cta     3840
Gly Tyr Thr Leu Ser Asp Ile Leu Asn Glu Ile Thr Lys Glu Asp Leu
1265                1270                1275                1280

aga tac ctc cga cta cgg ggt ggt ctc ctc tgc aga ctc tgg agt gcg     3888
Arg Tyr Leu Arg Leu Arg Gly Gly Leu Leu Cys Arg Leu Trp Ser Ala
                1285                1290                1295

gtc tcc cag tac aga agg gct cag gag gcc tca gaa acc aaa gac aag     3936
Val Ser Gln Tyr Arg Arg Ala Gln Glu Ala Ser Glu Thr Lys Asp Lys
            1300                1305                1310

gct tga taccaatcag ctaagctgtg gcagagtgtc ccaccacgct acatgttttg      3992
Ala

ttaaagcttc tgttagtgta tacacgaatt ccgctgtgtt tacatattta aaaatgccat   4052

tgttcaatta atagtttaag aacttgtttt aaatactgtc ctgagtttct tttgaaacct   4112

gttatttata aacatagaac tgtgtgtatt gtgaaaacag tgagccttgg ttttgacctc   4172
```

-continued

```
ccggaatatt aggaaattca cttgtagtcc cagctatgca ggaggctgag gtgggaggat   4232

tgcttgagcc caggaggtgt ggaggctgca gtgagccatg atcacacca               4281


<210> SEQ ID NO 2
<211> LENGTH: 1313
<212> TYPE: PRT
<213> ORGANISM: Homo sapiens
<220> FEATURE:
<223> OTHER INFORMATION: human apoptosis signal regulating kinase
      related kinase (ASKRK)
<220> FEATURE:
<221> NAME/KEY: DOMAIN
<222> LOCATION: (658)..(909)
<223> OTHER INFORMATION: kinase domain

<400> SEQUENCE: 2

Met Glu Ser Gly Gly Gly Asn Ala Pro Ala Gly Ala Leu Gly Ala Ala
  1               5                  10                  15

Ser Glu Ser Pro Gln Cys Pro Pro Pro Pro Gly Val Glu Gly Ala Ala
             20                  25                  30

Gly Pro Ala Glu Pro Asp Gly Ala Ala Glu Gly Ala Ala Gly Gly Ser
         35                  40                  45

Gly Glu Gly Glu Ser Gly Gly Gly Pro Arg Arg Ala Leu Arg Ala Val
     50                  55                  60

Tyr Val Arg Ser Glu Ser Ser Gln Gly Gly Ala Ala Gly Gly Pro Glu
 65                  70                  75                  80

Ala Gly Ala Arg Gln Cys Leu Leu Arg Ala Cys Glu Ala Glu Gly Ala
                 85                  90                  95

His Leu Thr Ser Val Pro Phe Gly Glu Leu Asp Phe Gly Glu Thr Ala
            100                 105                 110

Val Leu Asp Ala Phe Tyr Asp Ala Asp Val Ala Val Val Asp Met Ser
        115                 120                 125

Asp Val Ser Arg Gln Pro Ser Leu Phe Tyr His Leu Gly Val Arg Glu
    130                 135                 140

Ser Phe Asp Met Ala Asn Asn Val Ile Leu Tyr His Asp Thr Asp Ala
145                 150                 155                 160

Asp Thr Ala Leu Ser Leu Lys Asp Met Val Thr Gln Lys Asn Thr Ala
                165                 170                 175

Ser Ser Gly Asn Tyr Tyr Phe Ile Pro Tyr Ile Val Thr Pro Cys Thr
            180                 185                 190

Asp Tyr Phe Cys Cys Glu Ser Asp Ala Gln Arg Arg Ala Ser Glu Tyr
        195                 200                 205

Met Gln Pro Asn Trp Asp Asn Ile Leu Gly Pro Leu Cys Met Pro Leu
    210                 215                 220

Val Asp Arg Phe Ile Ser Leu Leu Lys Asp Ile His Val Thr Ser Cys
225                 230                 235                 240

Val Tyr Tyr Lys Glu Thr Leu Leu Asn Asp Ile Arg Lys Ala Arg Glu
                245                 250                 255

Lys Tyr Gln Gly Glu Glu Leu Ala Lys Glu Leu Ala Arg Ile Lys Leu
            260                 265                 270

Arg Met Asp Asn Thr Glu Val Leu Thr Ser Asp Ile Ile Ile Asn Leu
        275                 280                 285

Leu Leu Ser Tyr Arg Asp Ile Gln Asp Tyr Asp Ala Met Val Lys Leu
    290                 295                 300

Val Glu Thr Leu Glu Met Leu Pro Thr Cys Asp Leu Ala Asp Gln His
305                 310                 315                 320
```

-continued

```
Asn Thr Lys Phe His Tyr Ala Phe Ala Leu Asn Arg Arg Asn Ser Thr
                325                 330                 335

Gly Asp Arg Glu Lys Ala Leu Gln Ile Met Leu Gln Val Leu Gln Ser
            340                 345                 350

Cys Asp His Pro Gly Pro Asp Met Phe Cys Leu Cys Gly Arg Ile Tyr
        355                 360                 365

Lys Asp Ile Phe Leu Asp Ser Asp Cys Lys Asp Asp Thr Ser Arg Asp
    370                 375                 380

Ser Ala Ile Glu Trp Tyr Arg Lys Gly Phe Glu Leu Gln Ser Ser Leu
385                 390                 395                 400

Tyr Ser Gly Ile Asn Leu Ala Val Leu Leu Ile Val Ala Gly Gln Gln
                405                 410                 415

Phe Glu Thr Ser Leu Glu Leu Arg Lys Ile Gly Val Arg Leu Asn Ser
            420                 425                 430

Leu Leu Gly Arg Lys Gly Ser Leu Glu Lys Met Asn Asn Tyr Trp Asp
        435                 440                 445

Val Gly Gln Phe Phe Ser Val Ser Met Leu Ala His Asp Val Gly Lys
    450                 455                 460

Ala Val Gln Ala Ala Glu Arg Leu Phe Lys Leu Lys Pro Pro Val Trp
465                 470                 475                 480

Tyr Leu Arg Ser Leu Val Gln Asn Leu Leu Leu Ile Arg Arg Phe Lys
                485                 490                 495

Lys Thr Ile Ile Glu His Ser Pro Arg Gln Glu Arg Leu Asn Phe Trp
            500                 505                 510

Leu Asp Ile Ile Phe Glu Ala Thr Asn Glu Val Thr Asn Gly Leu Arg
        515                 520                 525

Phe Pro Val Leu Val Ile Glu Pro Thr Lys Val Tyr Gln Pro Ser Tyr
    530                 535                 540

Val Ser Ile Asn Asn Glu Ala Glu Glu Arg Thr Val Ser Leu Trp His
545                 550                 555                 560

Val Ser Pro Thr Glu Met Lys Gln Met His Glu Trp Asn Phe Thr Ala
                565                 570                 575

Ser Ser Ile Lys Gly Ile Ser Leu Ser Lys Phe Asp Glu Arg Cys Cys
            580                 585                 590

Phe Leu Tyr Val His Asp Asn Ser Asp Asp Phe Gln Ile Tyr Phe Ser
        595                 600                 605

Thr Glu Glu Gln Cys Ser Arg Phe Phe Ser Leu Val Lys Glu Met Ile
    610                 615                 620

Thr Asn Thr Ala Gly Ser Thr Val Glu Leu Glu Gly Glu Thr Asp Gly
625                 630                 635                 640

Asp Thr Leu Glu Tyr Glu Tyr Asp His Asp Ala Asn Gly Glu Arg Val
                645                 650                 655

Val Leu Gly Lys Gly Thr Tyr Gly Ile Val Tyr Ala Gly Arg Asp Leu
            660                 665                 670

Ser Asn Gln Val Arg Ile Ala Ile Lys Glu Ile Pro Glu Arg Asp Ser
        675                 680                 685

Arg Tyr Ser Gln Pro Leu His Glu Glu Ile Ala Leu His Lys Tyr Leu
    690                 695                 700

Lys His Arg Asn Ile Val Gln Tyr Leu Gly Ser Val Ser Glu Asn Gly
705                 710                 715                 720

Tyr Ile Lys Ile Phe Met Glu Gln Val Pro Gly Gly Ser Leu Ser Ala
                725                 730                 735
```

-continued

```
Leu Leu Arg Ser Lys Trp Gly Pro Met Lys Glu Pro Thr Ile Lys Phe
            740                 745                 750

Tyr Thr Lys Gln Ile Leu Glu Gly Leu Lys Tyr Leu His Glu Asn Gln
        755                 760                 765

Ile Val His Arg Asp Ile Lys Gly Asp Asn Val Leu Val Asn Thr Tyr
    770                 775                 780

Ser Gly Val Val Lys Ile Ser Asp Phe Gly Thr Ser Lys Arg Leu Ala
785                 790                 795                 800

Gly Val Asn Pro Cys Thr Glu Thr Phe Thr Gly Thr Leu Gln Tyr Met
                805                 810                 815

Ala Pro Glu Ile Ile Asp Gln Gly Pro Arg Gly Tyr Gly Ala Pro Ala
            820                 825                 830

Asp Ile Trp Ser Leu Gly Cys Thr Ile Ile Glu Met Ala Thr Ser Lys
        835                 840                 845

Pro Pro Phe His Glu Leu Gly Glu Pro Gln Ala Ala Met Phe Lys Val
    850                 855                 860

Gly Met Phe Lys Ile His Pro Glu Ile Pro Glu Ala Leu Ser Ala Glu
865                 870                 875                 880

Ala Arg Ala Phe Ile Leu Ser Cys Phe Glu Pro Asp Pro His Lys Arg
                885                 890                 895

Ala Thr Thr Ala Glu Leu Leu Arg Glu Gly Phe Leu Arg Gln Val Asn
            900                 905                 910

Lys Gly Lys Lys Asn Arg Ile Ala Phe Lys Pro Ser Glu Gly Pro Arg
        915                 920                 925

Gly Val Val Leu Ala Leu Pro Thr Gln Gly Glu Pro Met Ala Thr Ser
    930                 935                 940

Ser Ser Glu His Gly Ser Val Ser Pro Asp Ser Asp Ala Gln Pro Asp
945                 950                 955                 960

Ala Leu Phe Glu Arg Thr Arg Ala Pro Arg His His Leu Gly His Leu
                965                 970                 975

Leu Ser Val Pro Asp Glu Ser Ser Ala Leu Glu Asp Arg Gly Leu Ala
            980                 985                 990

Ser Ser Pro Glu Asp Arg Asp Gln Gly Leu Phe Leu Leu Arg Lys Asp
        995                 1000                1005

Ser Glu Arg Arg Ala Ile Leu Tyr Lys Ile Leu Trp Glu Glu Gln Asn
    1010                1015                1020

Gln Val Ala Ser Asn Leu Gln Glu Cys Val Ala Gln Ser Ser Glu Glu
1025                1030                1035                1040

Leu His Leu Ser Val Gly His Ile Lys Gln Ile Ile Gly Ile Leu Arg
                1045                1050                1055

Asp Phe Ile Arg Ser Pro Glu His Arg Val Met Ala Thr Thr Ile Ser
            1060                1065                1070

Lys Leu Lys Val Asp Leu Asp Phe Asp Ser Ser Ser Ile Ser Gln Ile
        1075                1080                1085

His Leu Val Leu Phe Gly Phe Gln Asp Ala Val Asn Lys Ile Leu Arg
    1090                1095                1100

Asn His Leu Ile Arg Pro His Trp Met Phe Ala Met Asp Asn Ile Ile
1105                1110                1115                1120

Arg Arg Ala Val Gln Ala Ala Val Thr Ile Leu Ile Pro Glu Leu Arg
                1125                1130                1135

Ala His Phe Glu Pro Thr Cys Glu Thr Glu Gly Val Asp Lys Asp Met
            1140                1145                1150

Asp Glu Ala Glu Glu Gly Tyr Pro Pro Ala Thr Gly Pro Gly Gln Glu
```

-continued

```
        1155                1160                1165

Ala Gln Pro His Gln Gln His Leu Ser Leu Gln Leu Gly Glu Leu Arg
    1170                1175                1180

Gln Glu Thr Asn Arg Leu Leu Glu His Leu Val Glu Lys Glu Arg Glu
1185                1190                1195                1200

Tyr Gln Asn Leu Leu Arg Gln Thr Leu Glu Gln Lys Thr Gln Glu Leu
                1205                1210                1215

Tyr His Leu Gln Leu Lys Leu Lys Ser Asn Cys Ile Thr Glu Asn Pro
            1220                1225                1230

Ala Gly Pro Tyr Gly Gln Arg Thr Asp Lys Glu Leu Ile Asp Trp Leu
        1235                1240                1245

Arg Leu Gln Gly Ala Asp Ala Lys Thr Ile Glu Lys Ile Val Glu Glu
    1250                1255                1260

Gly Tyr Thr Leu Ser Asp Ile Leu Asn Glu Ile Thr Lys Glu Asp Leu
1265                1270                1275                1280

Arg Tyr Leu Arg Leu Arg Gly Gly Leu Leu Cys Arg Leu Trp Ser Ala
                1285                1290                1295

Val Ser Gln Tyr Arg Arg Ala Gln Glu Ala Ser Glu Thr Lys Asp Lys
            1300                1305                1310

Ala


<210> SEQ ID NO 3
<211> LENGTH: 4221
<212> TYPE: DNA
<213> ORGANISM: Mus sp.
<220> FEATURE:
<223> OTHER INFORMATION: partial mouse apoptosis signal regulating
      kinase related kinase (ASKRK)

<400> SEQUENCE: 3

gccgagggcg ggcgcgggcc acgccgggct ctgcgggctg tctacgtgcg cagcgaaagt     60

tcgcaggggg cagccgccgg cggcggcccc gaggccgggg cgctcaagtg cctgcttcgg    120

gcttgcgaag ccgagggcgc ccacctcacc tccgtcccct tcggggagct cgacttcggg    180

gagacggccg tgctcgatgc cttctacgat gcagatgttg ccattgtgga catgagtgat    240

atctccagac agccttccct tttctaccat cttggagtcc gagagagttt tgacatggct    300

aacaatgtaa ttctctacta tgatactgat gctgacactg ctctgtcatt gaaggatatg    360

gtcactcaaa aaaacacagc atccagtgga aattattatt ttatccccta cactgtgaca    420

ccatgtgctg actatttttg ctgtgagagt gatgcccaaa ggagagcctc agagtacatg    480

cagcctaact gggacaccat actgggcccg ctgtgtatgc ccctggtcga caggttcact    540

agcctcctta aggacatccg tgtgacttca tgtgcttatt ataaagaaac attgttaaat    600

gacatccgga aagccagaga gaaataccaa ggtgatgaac tggcgaaaga gttgactcgg    660

atcaaattcc gtatggataa cattgaggtt ctgacatcag acatcatcat taacttactt    720

ctgtcctacc gtgatatcca ggactacgat gcaatggtca agctggtaga gacactgaag    780

atgctgccaa cgtgtgattt ggctgatcag cacaacatta aatttcacta tgcatttgca    840

ctgaatagga gaaacagcac aggtgaccgt gaaaaggctc ttcaggttat gctccaagtt    900

ctgcaaagct gtgaccaccc agctcctgac atgttttgcc tgtgtgggcg gatatacaag    960

gacatcttcc tggattcagg ttgtgaagag gatgcaagca gagacagtgc cattgagtgg   1020

tatcgcaaag ggtttgaact ccagtcatcc ctttattcag gaattaacct tgcagttttg   1080

ctgatagttt ctggacaaca gtttgaaact tcgatggaac taaggaaaat aggtgtccgg   1140
```

-continued

```
ctgaacagtt tattgggaag aaaagggagc ctggagaaaa tgaacaatta ctgggatgta   1200
ggtcagttct tcaccgtcag catgctggca agtgatattg ggaaagctgt ccaggcagca   1260
gagaggttgt tcaaactgaa acccccagtc tggtacctgc ggtcattagt tcagaacttg   1320
ctgttaattc aacgcttcaa gaaacccatt acagaacatt cacccaggca ggaacggctt   1380
aacttctggt tagatatcat ttttgaagca acgaatgaag ttactaatgg actcagattt   1440
ccagttctgg taatagagcc aaccaaagtc taccagcctt cttatgtttc tatcaacaat   1500
gaagctgaag aaagaactgt ttctttatgg catgtctcac ccacagaaat gaaacaaatc   1560
catgagtgga attttacagc ctcttctatt aaaggaataa gcctatccaa gtttgatgaa   1620
cggtgctgtt ttctttatgt ccatgataat tctgatgact ttcaaatcta cttttccacc   1680
gaagaccagt gtaatagatt ttgttctttg gtcaaagaga tgctaaacaa tggagtgggc   1740
agtacagtgg agttggaggg agaggctgat ggagacacct tagagtatga gtatgaccat   1800
gatgcgaatg gggagagagt tgtcttgggg aaaggctcct atgggattgt gtatgccggc   1860
cgtgatctca gtaatcaagt acggatagcc atcaaggaaa tcccagagag agatatcagg   1920
tactctcagc ctctgcatga agaaatagct ctgcacaagt atctcaaaca tcgcaacatc   1980
gtccagtacc ttggctctgt ttcagagaat ggctacatta agatatttat ggagcaggtg   2040
cctggaggaa gcctttctgc tctcttacga tctaaatggg gacctatgaa ggaacccact   2100
atcaagtttt ataccaaaca gatcctggaa ggcctgaagt atctccatga aaaccagata   2160
gtgcacagag acataaaggg agataatgtt ctggtgaaca cctatagtgg agtggtaaaa   2220
atctctgatt ttggaacctc taaacgcctc gcaggaatta acccatgcac cgagaccttt   2280
acaggaactc tgcagtacat ggcacctgag attattgatc aaggacctcg gggatatggt   2340
gctccagctg atatctggtc cttgggctgc accatcattg agatggcaac cagcaggcct   2400
ccattccatg agcttggtga gccccaagca gccatgttta aggtagggat gtttaagatc   2460
caccctgaaa ttccagaggc cctttcagct gaagccagag ccttcatctt gtcttgtttt   2520
gagcctgacc ctcagaaacg tgtcactgct gctgaccttc tccaagaagg gttcttaagg   2580
caggtgaaca aaggcaaaaa gaaccgaatt gctttcaagc cttcagaggg tgttcggagt   2640
ggcactggta ctctggctct gccttcatca ggagagcttg tgggcagcag cagcagcgag   2700
catggctcaa tctccccaga ctcggatgcc cagcctgatg cattctttga gaaagtccag   2760
gtgcccaaac atcagctcag ccaccttctc agtgtcccag atgaaagccc agccttagat   2820
gaccgaagca cagccttacc cccagaggag agggaccctg gtctctttct gctgcgcaag   2880
gacagtgagc gcagagccat cctttacaga atcctttggg aggaacagaa ccaagtggct   2940
tccaacttgc aagagtgtgt ggtccagagt tcagaagagt tgcttctctc agttagccac   3000
atcaaacaga taattggaat cctgagggac ttcatccgct ccccagagca cagggtgatg   3060
gcagccacaa tatcaaaact aaaggtggac ctggactttg acagctcatc catcaaccag   3120
attcacctga ttctgtttgg gttccaagat gctgtcaata gaattttgag aaaccactta   3180
attaggcccc actggatgtt tgcaatggac aacatcattc gcagagctgt gcaggctgca   3240
gtcaccattc tcattccaga gctccaagcc cactttgagc ctgcttctga gactgaaggg   3300
gtagacaagg acacagaagt agaaggggac tatcccctag tagacctcct cagccaagaa   3360
gtgcatgtga cacctagagg caccagacct ggctcagtgg ctatccagga gggccagccc   3420
caccagcaag acccaagtct ccaactgagc aagctcaggc aagagaccaa cagactttgg   3480
```

-continued

```
gaacacctag ttcaaaaaga gaagggagta ccagaatctt cttcgcctaa ttctagacca   3540

gaaaactcaa gaattgtatc accttcagtt acagtacaaa tccaatggtg gtacagagaa   3600

ccctccaccc ctgatggact gggaaccgac agagagctta tagactggtt gcaactacaa   3660

ggagtggatg ccaatacaat agaaaagatt gttgaagagg actatacact ttctgatatt   3720

ctcaatgata tcactaagga agacctaagg tgcctccgac tacggggtgg tgtcctctgt   3780

aggctctggc atgcagtctc ccagcacaga agacaaatgc aggagtcttc acagtgagcc   3840

aagcctgggg agaatgggca aaaagtcccc tacacctgct catgattaaa gcttctgttg   3900

gcgtactcac aaactccgag tttccacaga aagacccttg tccatttaat tcaagcacgt   3960

gtgattgtag agcatccttg tttataaaca agattgtaag taatgtcagc cctgacctaa   4020

tatttaaaaa gtcagcatat cgctggaaag ataaagcata cgtattttat aaactagtgt   4080

aattacttaa atgtgaaagg ttaaaaagtg tgccttgcaa tgggagtaca gtttcatgta   4140

tgttaaatgt ctaaatggaa aaaattaaac tattttacct ttaaaaaaaa aaaaaaaaaa   4200

actcgacgag ctcactagtc g                                             4221
```

```
<210> SEQ ID NO 4
<211> LENGTH: 1278
<212> TYPE: PRT
<213> ORGANISM: Mus sp.
<220> FEATURE:
<223> OTHER INFORMATION: partial mouse apoptosis signal regulating
      kinase related kinase (ASKRK)
<220> FEATURE:
<221> NAME/KEY: DOMAIN
<222> LOCATION: (609)..(860)
<223> OTHER INFORMATION: kinase domain

<400> SEQUENCE: 4

Ala Glu Gly Gly Arg Gly Pro Arg Arg Ala Leu Arg Ala Val Tyr Val
  1               5                  10                  15

Arg Ser Glu Ser Ser Gln Gly Ala Ala Ala Gly Gly Gly Pro Glu Ala
             20                  25                  30

Gly Ala Leu Lys Cys Leu Leu Arg Ala Cys Glu Ala Glu Gly Ala His
         35                  40                  45

Leu Thr Ser Val Pro Phe Gly Glu Leu Asp Phe Gly Glu Thr Ala Val
     50                  55                  60

Leu Asp Ala Phe Tyr Asp Ala Asp Val Ala Ile Val Asp Met Ser Asp
 65                  70                  75                  80

Ile Ser Arg Gln Pro Ser Leu Phe Tyr His Leu Gly Val Arg Glu Ser
                 85                  90                  95

Phe Asp Met Ala Asn Asn Val Ile Leu Tyr Tyr Asp Thr Asp Ala Asp
            100                 105                 110

Thr Ala Leu Ser Leu Lys Asp Met Val Thr Gln Lys Asn Thr Ala Ser
        115                 120                 125

Ser Gly Asn Tyr Tyr Phe Ile Pro Tyr Thr Val Thr Pro Cys Ala Asp
    130                 135                 140

Tyr Phe Cys Cys Glu Ser Asp Ala Gln Arg Arg Ala Ser Glu Tyr Met
145                 150                 155                 160

Gln Pro Asn Trp Asp Thr Ile Leu Gly Pro Leu Cys Met Pro Leu Val
                165                 170                 175

Asp Arg Phe Thr Ser Leu Leu Lys Asp Ile Arg Val Thr Ser Cys Ala
            180                 185                 190

Tyr Tyr Lys Glu Thr Leu Leu Asn Asp Ile Arg Lys Ala Arg Glu Lys
        195                 200                 205
```

-continued

```
Tyr Gln Gly Asp Glu Leu Ala Lys Glu Leu Thr Arg Ile Lys Phe Arg
    210                 215                 220

Met Asp Asn Ile Glu Val Leu Thr Ser Asp Ile Ile Ile Asn Leu Leu
225                 230                 235                 240

Leu Ser Tyr Arg Asp Ile Gln Asp Tyr Asp Ala Met Val Lys Leu Val
                245                 250                 255

Glu Thr Leu Lys Met Leu Pro Thr Cys Asp Leu Ala Asp Gln His Asn
            260                 265                 270

Ile Lys Phe His Tyr Ala Phe Ala Leu Asn Arg Arg Asn Ser Thr Gly
        275                 280                 285

Asp Arg Glu Lys Ala Leu Gln Val Met Leu Gln Val Leu Gln Ser Cys
    290                 295                 300

Asp His Pro Ala Pro Asp Met Phe Cys Leu Cys Gly Arg Ile Tyr Lys
305                 310                 315                 320

Asp Ile Phe Leu Asp Ser Gly Cys Glu Glu Asp Ala Ser Arg Asp Ser
                325                 330                 335

Ala Ile Glu Trp Tyr Arg Lys Gly Phe Glu Leu Gln Ser Ser Leu Tyr
            340                 345                 350

Ser Gly Ile Asn Leu Ala Val Leu Leu Ile Val Ser Gly Gln Gln Phe
        355                 360                 365

Glu Thr Ser Met Glu Leu Arg Lys Ile Gly Val Arg Leu Asn Ser Leu
    370                 375                 380

Leu Gly Arg Lys Gly Ser Leu Glu Lys Met Asn Asn Tyr Trp Asp Val
385                 390                 395                 400

Gly Gln Phe Phe Thr Val Ser Met Leu Ala Ser Asp Ile Gly Lys Ala
                405                 410                 415

Val Gln Ala Ala Glu Arg Leu Phe Lys Leu Lys Pro Pro Val Trp Tyr
            420                 425                 430

Leu Arg Ser Leu Val Gln Asn Leu Leu Leu Ile Gln Arg Phe Lys Lys
        435                 440                 445

Pro Ile Thr Glu His Ser Pro Arg Gln Glu Arg Leu Asn Phe Trp Leu
    450                 455                 460

Asp Ile Ile Phe Glu Ala Thr Asn Glu Val Thr Asn Gly Leu Arg Phe
465                 470                 475                 480

Pro Val Leu Val Ile Glu Pro Thr Lys Val Tyr Gln Pro Ser Tyr Val
                485                 490                 495

Ser Ile Asn Asn Glu Ala Glu Glu Arg Thr Val Ser Leu Trp His Val
            500                 505                 510

Ser Pro Thr Glu Met Lys Gln Ile His Glu Trp Asn Phe Thr Ala Ser
        515                 520                 525

Ser Ile Lys Gly Ile Ser Leu Ser Lys Phe Asp Glu Arg Cys Cys Phe
    530                 535                 540

Leu Tyr Val His Asp Asn Ser Asp Asp Phe Gln Ile Tyr Phe Ser Thr
545                 550                 555                 560

Glu Asp Gln Cys Asn Arg Phe Cys Ser Leu Val Lys Glu Met Leu Asn
                565                 570                 575

Asn Gly Val Gly Ser Thr Val Glu Leu Glu Gly Glu Ala Asp Gly Asp
            580                 585                 590

Thr Leu Glu Tyr Glu Tyr Asp His Asp Ala Asn Gly Glu Arg Val Val
        595                 600                 605

Leu Gly Lys Gly Ser Tyr Gly Ile Val Tyr Ala Gly Arg Asp Leu Ser
    610                 615                 620
```

-continued

```
Asn Gln Val Arg Ile Ala Ile Lys Glu Ile Pro Glu Arg Asp Ile Arg
625                 630                 635                 640

Tyr Ser Gln Pro Leu His Glu Glu Ile Ala Leu His Lys Tyr Leu Lys
                645                 650                 655

His Arg Asn Ile Val Gln Tyr Leu Gly Ser Val Ser Glu Asn Gly Tyr
            660                 665                 670

Ile Lys Ile Phe Met Glu Gln Val Pro Gly Gly Ser Leu Ser Ala Leu
        675                 680                 685

Leu Arg Ser Lys Trp Gly Pro Met Lys Glu Pro Thr Ile Lys Phe Tyr
    690                 695                 700

Thr Lys Gln Ile Leu Glu Gly Leu Lys Tyr Leu His Glu Asn Gln Ile
705                 710                 715                 720

Val His Arg Asp Ile Lys Gly Asp Asn Val Leu Val Asn Thr Tyr Ser
                725                 730                 735

Gly Val Val Lys Ile Ser Asp Phe Gly Thr Ser Lys Arg Leu Ala Gly
            740                 745                 750

Ile Asn Pro Cys Thr Glu Thr Phe Thr Gly Thr Leu Gln Tyr Met Ala
        755                 760                 765

Pro Glu Ile Ile Asp Gln Gly Pro Arg Gly Tyr Gly Ala Pro Ala Asp
    770                 775                 780

Ile Trp Ser Leu Gly Cys Thr Ile Ile Glu Met Ala Thr Ser Arg Pro
785                 790                 795                 800

Pro Phe His Glu Leu Gly Glu Pro Gln Ala Ala Met Phe Lys Val Gly
                805                 810                 815

Met Phe Lys Ile His Pro Glu Ile Pro Glu Ala Leu Ser Ala Glu Ala
            820                 825                 830

Arg Ala Phe Ile Leu Ser Cys Phe Glu Pro Asp Pro Gln Lys Arg Val
        835                 840                 845

Thr Ala Ala Asp Leu Leu Gln Glu Gly Phe Leu Arg Gln Val Asn Lys
    850                 855                 860

Gly Lys Lys Asn Arg Ile Ala Phe Lys Pro Ser Glu Gly Val Arg Ser
865                 870                 875                 880

Gly Thr Gly Thr Leu Ala Leu Pro Ser Ser Gly Glu Leu Val Gly Ser
                885                 890                 895

Ser Ser Ser Glu His Gly Ser Ile Ser Pro Asp Ser Asp Ala Gln Pro
            900                 905                 910

Asp Ala Phe Phe Glu Lys Val Gln Val Pro Lys His Gln Leu Ser His
        915                 920                 925

Leu Leu Ser Val Pro Asp Glu Ser Pro Ala Leu Asp Asp Arg Ser Thr
    930                 935                 940

Ala Leu Pro Pro Glu Glu Arg Asp Pro Gly Leu Phe Leu Leu Arg Lys
945                 950                 955                 960

Asp Ser Glu Arg Arg Ala Ile Leu Tyr Arg Ile Leu Trp Glu Glu Gln
                965                 970                 975

Asn Gln Val Ala Ser Asn Leu Gln Glu Cys Val Val Gln Ser Ser Glu
            980                 985                 990

Glu Leu Leu Leu Ser Val Ser His Ile Lys Gln Ile Ile Gly Ile Leu
        995                 1000                1005

Arg Asp Phe Ile Arg Ser Pro Glu His Arg Val Met Ala Ala Thr Ile
    1010                1015                1020

Ser Lys Leu Lys Val Asp Leu Asp Phe Asp Ser Ser Ser Ile Asn Gln
1025                1030                1035                1040

Ile His Leu Ile Leu Phe Gly Phe Gln Asp Ala Val Asn Arg Ile Leu
```

-continued

```
                1045                1050                1055

Arg Asn His Leu Ile Arg Pro His Trp Met Phe Ala Met Asp Asn Ile
            1060                1065                1070

Ile Arg Arg Ala Val Gln Ala Ala Val Thr Ile Leu Ile Pro Glu Leu
        1075                1080                1085

Gln Ala His Phe Glu Pro Ala Ser Glu Thr Glu Gly Val Asp Lys Asp
    1090                1095                1100

Thr Glu Val Glu Gly Asp Tyr Pro Leu Val Asp Leu Leu Ser Gln Glu
1105                1110                1115                1120

Val His Val Thr Pro Arg Gly Thr Arg Pro Gly Ser Val Ala Ile Gln
                1125                1130                1135

Glu Gly Gln Pro His Gln Gln Asp Pro Ser Leu Gln Leu Ser Lys Leu
            1140                1145                1150

Arg Gln Glu Thr Asn Arg Leu Trp Glu His Leu Val Gln Lys Glu Lys
        1155                1160                1165

Gly Val Pro Glu Ser Ser Ser Pro Asn Ser Arg Pro Glu Asn Ser Arg
    1170                1175                1180

Ile Val Ser Pro Ser Val Thr Val Gln Ile Gln Trp Trp Tyr Arg Glu
1185                1190                1195                1200

Pro Ser Thr Pro Asp Gly Leu Gly Thr Asp Arg Glu Leu Ile Asp Trp
                1205                1210                1215

Leu Gln Leu Gln Gly Val Asp Ala Asn Thr Ile Glu Lys Ile Val Glu
            1220                1225                1230

Glu Asp Tyr Thr Leu Ser Asp Ile Leu Asn Asp Ile Thr Lys Glu Asp
        1235                1240                1245

Leu Arg Cys Leu Arg Leu Arg Gly Gly Val Leu Cys Arg Leu Trp His
    1250                1255                1260

Ala Val Ser Gln His Arg Arg Gln Met Gln Glu Ser Ser Gln
1265                1270                1275


<210> SEQ ID NO 5
<211> LENGTH: 1277
<212> TYPE: PRT
<213> ORGANISM: Mus sp.
<220> FEATURE:
<223> OTHER INFORMATION: partial mouse apoptosis signal regulating
      kinase related kinase (ASKRK)

<400> SEQUENCE: 5

Glu Gly Gly Arg Gly Pro Arg Arg Ala Leu Arg Ala Val Tyr Val Arg
  1               5                  10                  15

Ser Glu Ser Ser Gln Gly Ala Ala Ala Gly Gly Gly Pro Glu Ala Gly
             20                  25                  30

Ala Leu Lys Cys Leu Leu Arg Ala Cys Glu Ala Glu Gly Ala His Leu
         35                  40                  45

Thr Ser Val Pro Phe Gly Glu Leu Asp Phe Gly Glu Thr Ala Val Leu
     50                  55                  60

Asp Ala Phe Tyr Asp Ala Asp Val Ala Ile Val Asp Met Ser Asp Ile
 65                  70                  75                  80

Ser Arg Gln Pro Ser Leu Phe Tyr His Leu Gly Val Arg Glu Ser Phe
                 85                  90                  95

Asp Met Ala Asn Asn Val Ile Leu Tyr Tyr Asp Thr Asp Ala Asp Thr
            100                 105                 110

Ala Leu Ser Leu Lys Asp Met Val Thr Gln Lys Asn Thr Ala Ser Ser
        115                 120                 125
```

-continued

```
Gly Asn Tyr Tyr Phe Ile Pro Tyr Thr Val Thr Pro Cys Ala Asp Tyr
    130                 135                 140

Phe Cys Cys Glu Ser Asp Ala Gln Arg Arg Ala Ser Glu Tyr Met Gln
145                 150                 155                 160

Pro Asn Trp Asp Thr Ile Leu Gly Pro Leu Cys Met Pro Leu Val Asp
                165                 170                 175

Arg Phe Thr Ser Leu Leu Lys Asp Ile Arg Val Thr Ser Cys Ala Tyr
            180                 185                 190

Tyr Lys Glu Thr Leu Leu Asn Asp Ile Arg Lys Ala Arg Glu Lys Tyr
        195                 200                 205

Gln Gly Asp Glu Leu Ala Lys Glu Leu Thr Arg Ile Lys Phe Arg Met
    210                 215                 220

Asp Asn Ile Glu Val Leu Thr Ser Asp Ile Ile Ile Asn Leu Leu Leu
225                 230                 235                 240

Ser Tyr Arg Asp Ile Gln Asp Tyr Asp Ala Met Val Lys Leu Val Glu
                245                 250                 255

Thr Leu Lys Met Leu Pro Thr Cys Asp Leu Ala Asp Gln His Asn Ile
            260                 265                 270

Lys Phe His Tyr Ala Phe Ala Leu Asn Arg Arg Asn Ser Thr Gly Asp
        275                 280                 285

Arg Glu Lys Ala Leu Gln Val Met Leu Gln Val Leu Gln Ser Cys Asp
    290                 295                 300

His Pro Ala Pro Asp Met Phe Cys Leu Cys Gly Arg Ile Tyr Lys Asp
305                 310                 315                 320

Ile Phe Leu Asp Ser Gly Cys Glu Glu Asp Ala Ser Arg Asp Ser Ala
                325                 330                 335

Ile Glu Trp Tyr Arg Lys Gly Phe Glu Leu Gln Ser Ser Leu Tyr Ser
            340                 345                 350

Gly Ile Asn Leu Ala Val Leu Leu Ile Val Ser Gly Gln Gln Phe Glu
        355                 360                 365

Thr Ser Met Glu Leu Arg Lys Ile Gly Val Arg Leu Asn Ser Leu Leu
    370                 375                 380

Gly Arg Lys Gly Ser Leu Glu Lys Met Asn Asn Tyr Trp Asp Val Gly
385                 390                 395                 400

Gln Phe Phe Thr Val Ser Met Leu Ala Ser Asp Ile Gly Lys Ala Val
                405                 410                 415

Gln Ala Ala Glu Arg Leu Phe Lys Leu Lys Pro Pro Val Trp Tyr Leu
            420                 425                 430

Arg Ser Leu Val Gln Asn Leu Leu Leu Ile Gln Arg Phe Lys Lys Pro
        435                 440                 445

Ile Thr Glu His Ser Pro Arg Gln Glu Arg Leu Asn Phe Trp Leu Asp
    450                 455                 460

Ile Ile Phe Glu Ala Thr Asn Glu Val Thr Asn Gly Leu Arg Phe Pro
465                 470                 475                 480

Val Leu Val Ile Glu Pro Thr Lys Val Tyr Gln Pro Ser Tyr Val Ser
                485                 490                 495

Ile Asn Asn Glu Ala Glu Glu Arg Thr Val Ser Leu Trp His Val Ser
            500                 505                 510

Pro Thr Glu Met Lys Gln Ile His Glu Trp Asn Phe Thr Ala Ser Ser
        515                 520                 525

Ile Lys Gly Ile Ser Leu Ser Lys Phe Asp Glu Arg Cys Cys Phe Leu
    530                 535                 540

Tyr Val His Asp Asn Ser Asp Asp Phe Gln Ile Tyr Phe Ser Thr Glu
```

-continued

```
545                 550                 555                 560

Asp Gln Cys Asn Arg Phe Cys Ser Leu Val Lys Glu Met Leu Asn Asn
                565                 570                 575

Gly Val Gly Ser Thr Val Glu Leu Glu Gly Glu Ala Asp Gly Asp Thr
            580                 585                 590

Leu Glu Tyr Glu Tyr Asp His Asp Ala Asn Gly Glu Arg Val Val Leu
        595                 600                 605

Gly Lys Gly Ser Tyr Gly Ile Val Tyr Ala Gly Arg Asp Leu Ser Asn
    610                 615                 620

Gln Val Arg Ile Ala Ile Lys Glu Ile Pro Glu Arg Asp Ile Arg Tyr
625                 630                 635                 640

Ser Gln Pro Leu His Glu Glu Ile Ala Leu His Lys Tyr Leu Lys His
                645                 650                 655

Arg Asn Ile Val Gln Tyr Leu Gly Ser Val Ser Glu Asn Gly Tyr Ile
            660                 665                 670

Lys Ile Phe Met Glu Gln Val Pro Gly Gly Ser Leu Ser Ala Leu Leu
        675                 680                 685

Arg Ser Lys Trp Gly Pro Met Lys Glu Pro Thr Ile Lys Phe Tyr Thr
    690                 695                 700

Lys Gln Ile Leu Glu Gly Leu Lys Tyr Leu His Glu Asn Gln Ile Val
705                 710                 715                 720

His Arg Asp Ile Lys Gly Asp Asn Val Leu Val Asn Thr Tyr Ser Gly
                725                 730                 735

Val Val Lys Ile Ser Asp Phe Gly Thr Ser Lys Arg Leu Ala Gly Ile
            740                 745                 750

Asn Pro Cys Thr Glu Thr Phe Thr Gly Thr Leu Gln Tyr Met Ala Pro
        755                 760                 765

Glu Ile Ile Asp Gln Gly Pro Arg Gly Tyr Gly Ala Pro Ala Asp Ile
    770                 775                 780

Trp Ser Leu Gly Cys Thr Ile Ile Glu Met Ala Thr Ser Arg Pro Pro
785                 790                 795                 800

Phe His Glu Leu Gly Glu Pro Gln Ala Ala Met Phe Lys Val Gly Met
                805                 810                 815

Phe Lys Ile His Pro Glu Ile Pro Glu Ala Leu Ser Ala Glu Ala Arg
            820                 825                 830

Ala Phe Ile Leu Ser Cys Phe Glu Pro Asp Pro Gln Lys Arg Val Thr
        835                 840                 845

Ala Ala Asp Leu Leu Gln Glu Gly Phe Leu Arg Gln Val Asn Lys Gly
    850                 855                 860

Lys Lys Asn Arg Ile Ala Phe Lys Pro Ser Glu Gly Val Arg Ser Gly
865                 870                 875                 880

Thr Gly Thr Leu Ala Leu Pro Ser Ser Gly Glu Leu Val Gly Ser Ser
                885                 890                 895

Ser Ser Glu His Gly Ser Ile Ser Pro Asp Ser Asp Ala Gln Pro Asp
            900                 905                 910

Ala Phe Phe Glu Lys Val Gln Val Pro Lys His Gln Leu Ser His Leu
        915                 920                 925

Leu Ser Val Pro Asp Glu Ser Pro Ala Leu Asp Asp Arg Ser Thr Ala
    930                 935                 940

Leu Pro Pro Glu Glu Arg Asp Pro Gly Leu Phe Leu Leu Arg Lys Asp
945                 950                 955                 960

Ser Glu Arg Arg Ala Ile Leu Tyr Arg Ile Leu Trp Glu Glu Gln Asn
                965                 970                 975
```

-continued

```
Gln Val Ala Ser Asn Leu Gln Glu Cys Val Val Gln Ser Ser Glu Glu
            980                 985                 990

Leu Leu Leu Ser Val Ser His Ile Lys Gln Ile Ile Gly Ile Leu Arg
        995                 1000                1005

Asp Phe Ile Arg Ser Pro Glu His Arg Val Met Ala Ala Thr Ile Ser
    1010                1015                1020

Lys Leu Lys Val Asp Leu Asp Phe Asp Ser Ser Ser Ile Asn Gln Ile
1025                1030                1035                1040

His Leu Ile Leu Phe Gly Phe Gln Asp Ala Val Asn Arg Ile Leu Arg
                1045                1050                1055

Asn His Leu Ile Arg Pro His Trp Met Phe Ala Met Asp Asn Ile Ile
            1060                1065                1070

Arg Arg Ala Val Gln Ala Ala Val Thr Ile Leu Ile Pro Glu Leu Gln
        1075                1080                1085

Ala His Phe Glu Pro Ala Ser Glu Thr Glu Gly Val Asp Lys Asp Thr
    1090                1095                1100

Glu Val Glu Gly Asp Tyr Pro Leu Val Asp Leu Leu Ser Gln Glu Val
1105                1110                1115                1120

His Val Thr Pro Arg Gly Thr Arg Pro Gly Ser Val Ala Ile Gln Glu
                1125                1130                1135

Gly Gln Pro His Gln Gln Asp Pro Ser Leu Gln Leu Ser Lys Leu Arg
            1140                1145                1150

Gln Glu Thr Asn Arg Leu Trp Glu His Leu Val Gln Lys Glu Lys Gly
        1155                1160                1165

Val Pro Glu Ser Ser Ser Pro Asn Ser Arg Pro Glu Asn Ser Arg Ile
    1170                1175                1180

Val Ser Pro Ser Val Thr Val Gln Ile Gln Trp Trp Tyr Arg Glu Pro
1185                1190                1195                1200

Ser Thr Pro Asp Gly Leu Gly Thr Asp Arg Glu Leu Ile Asp Trp Leu
                1205                1210                1215

Gln Leu Gln Gly Val Asp Ala Asn Thr Ile Glu Lys Ile Val Glu Glu
            1220                1225                1230

Asp Tyr Thr Leu Ser Asp Ile Leu Asn Asp Ile Thr Lys Glu Asp Leu
        1235                1240                1245

Arg Cys Leu Arg Leu Arg Gly Gly Val Leu Cys Arg Leu Trp His Ala
    1250                1255                1260

Val Ser Gln His Arg Arg Gln Met Gln Glu Ser Ser Gln
1265                1270                1275


<210> SEQ ID NO 6
<211> LENGTH: 1257
<212> TYPE: PRT
<213> ORGANISM: Homo sapiens
<220> FEATURE:
<223> OTHER INFORMATION: partial human apoptosis signal regulating
      kinase related kinase (ASKRK)

<400> SEQUENCE: 6

Glu Ser Gly Gly Gly Pro Arg Arg Ala Leu Arg Ala Val Tyr Val Arg
  1               5                  10                  15

Ser Glu Ser Ser Gln Gly Gly Ala Ala Gly Gly Pro Glu Ala Gly Ala
             20                  25                  30

Arg Gln Cys Leu Leu Arg Ala Cys Glu Ala Glu Gly Ala His Leu Thr
         35                  40                  45

Ser Val Pro Phe Gly Glu Leu Asp Phe Gly Glu Thr Ala Val Leu Asp
```

-continued

```
     50                  55                  60

Ala Phe Tyr Asp Ala Asp Val Ala Val Val Asp Met Ser Asp Val Ser
 65                  70                  75                  80

Arg Gln Pro Ser Leu Phe Tyr His Leu Gly Val Arg Glu Ser Phe Asp
                85                  90                  95

Met Ala Asn Asn Val Ile Leu Tyr His Asp Thr Asp Ala Asp Thr Ala
            100                 105                 110

Leu Ser Leu Lys Asp Met Val Thr Gln Lys Asn Thr Ala Ser Ser Gly
        115                 120                 125

Asn Tyr Tyr Phe Ile Pro Tyr Ile Val Thr Pro Cys Thr Asp Tyr Phe
    130                 135                 140

Cys Cys Glu Ser Asp Ala Gln Arg Arg Ala Ser Glu Tyr Met Gln Pro
145                 150                 155                 160

Asn Trp Asp Asn Ile Leu Gly Pro Leu Cys Met Pro Leu Val Asp Arg
                165                 170                 175

Phe Ile Ser Leu Leu Lys Asp Ile His Val Thr Ser Cys Val Tyr Tyr
            180                 185                 190

Lys Glu Thr Leu Leu Asn Asp Ile Arg Lys Ala Arg Glu Lys Tyr Gln
        195                 200                 205

Gly Glu Glu Leu Ala Lys Glu Leu Ala Arg Ile Lys Leu Arg Met Asp
    210                 215                 220

Asn Thr Glu Val Leu Thr Ser Asp Ile Ile Ile Asn Leu Leu Leu Ser
225                 230                 235                 240

Tyr Arg Asp Ile Gln Asp Tyr Asp Ala Met Val Lys Leu Val Glu Thr
                245                 250                 255

Leu Glu Met Leu Pro Thr Cys Asp Leu Ala Asp Gln His Asn Thr Lys
            260                 265                 270

Phe His Tyr Ala Phe Ala Leu Asn Arg Arg Asn Ser Thr Gly Asp Arg
        275                 280                 285

Glu Lys Ala Leu Gln Ile Met Leu Gln Val Leu Gln Ser Cys Asp His
    290                 295                 300

Pro Gly Pro Asp Met Phe Cys Leu Cys Gly Arg Ile Tyr Lys Asp Ile
305                 310                 315                 320

Phe Leu Asp Ser Asp Cys Lys Asp Asp Thr Ser Arg Asp Ser Ala Ile
                325                 330                 335

Glu Trp Tyr Arg Lys Gly Phe Glu Leu Gln Ser Ser Leu Tyr Ser Gly
            340                 345                 350

Ile Asn Leu Ala Val Leu Leu Ile Val Ala Gly Gln Gln Phe Glu Thr
        355                 360                 365

Ser Leu Glu Leu Arg Lys Ile Gly Val Arg Leu Asn Ser Leu Leu Gly
    370                 375                 380

Arg Lys Gly Ser Leu Glu Lys Met Asn Asn Tyr Trp Asp Val Gly Gln
385                 390                 395                 400

Phe Phe Ser Val Ser Met Leu Ala His Asp Val Gly Lys Ala Val Gln
                405                 410                 415

Ala Ala Glu Arg Leu Phe Lys Leu Lys Pro Pro Val Trp Tyr Leu Arg
            420                 425                 430

Ser Leu Val Gln Asn Leu Leu Leu Ile Arg Arg Phe Lys Lys Thr Ile
        435                 440                 445

Ile Glu His Ser Pro Arg Gln Glu Arg Leu Asn Phe Trp Leu Asp Ile
    450                 455                 460

Ile Phe Glu Ala Thr Asn Glu Val Thr Asn Gly Leu Arg Phe Pro Val
465                 470                 475                 480
```

-continued

```
Leu Val Ile Glu Pro Thr Lys Val Tyr Gln Pro Ser Tyr Val Ser Ile
                485                 490                 495

Asn Asn Glu Ala Glu Glu Arg Thr Val Ser Leu Trp His Val Ser Pro
            500                 505                 510

Thr Glu Met Lys Gln Met His Glu Trp Asn Phe Thr Ala Ser Ser Ile
        515                 520                 525

Lys Gly Ile Ser Leu Ser Lys Phe Asp Glu Arg Cys Cys Phe Leu Tyr
    530                 535                 540

Val His Asp Asn Ser Asp Asp Phe Gln Ile Tyr Phe Ser Thr Glu Glu
545                 550                 555                 560

Gln Cys Ser Arg Phe Phe Ser Leu Val Lys Glu Met Ile Thr Asn Thr
                565                 570                 575

Ala Gly Ser Thr Val Glu Leu Glu Gly Glu Thr Asp Gly Asp Thr Leu
            580                 585                 590

Glu Tyr Glu Tyr Asp His Asp Ala Asn Gly Glu Arg Val Val Leu Gly
        595                 600                 605

Lys Gly Thr Tyr Gly Ile Val Tyr Ala Gly Arg Asp Leu Ser Asn Gln
    610                 615                 620

Val Arg Ile Ala Ile Lys Glu Ile Pro Glu Arg Asp Ser Arg Tyr Ser
625                 630                 635                 640

Gln Pro Leu His Glu Glu Ile Ala Leu His Lys Tyr Leu Lys His Arg
                645                 650                 655

Asn Ile Val Gln Tyr Leu Gly Ser Val Ser Glu Asn Gly Tyr Ile Lys
            660                 665                 670

Ile Phe Met Glu Gln Val Pro Gly Gly Ser Leu Ser Ala Leu Leu Arg
        675                 680                 685

Ser Lys Trp Gly Pro Met Lys Glu Pro Thr Ile Lys Phe Tyr Thr Lys
    690                 695                 700

Gln Ile Leu Glu Gly Leu Lys Tyr Leu His Glu Asn Gln Ile Val His
705                 710                 715                 720

Arg Asp Ile Lys Gly Asp Asn Val Leu Val Asn Thr Tyr Ser Gly Val
                725                 730                 735

Val Lys Ile Ser Asp Phe Gly Thr Ser Lys Arg Leu Ala Gly Val Asn
            740                 745                 750

Pro Cys Thr Glu Thr Phe Thr Gly Thr Leu Gln Tyr Met Ala Pro Glu
        755                 760                 765

Ile Ile Asp Gln Gly Pro Arg Gly Tyr Gly Ala Pro Ala Asp Ile Trp
    770                 775                 780

Ser Leu Gly Cys Thr Ile Ile Glu Met Ala Thr Ser Lys Pro Pro Phe
785                 790                 795                 800

His Glu Leu Gly Glu Pro Gln Ala Ala Met Phe Lys Val Gly Met Phe
                805                 810                 815

Lys Ile His Pro Glu Ile Pro Glu Ala Leu Ser Ala Glu Ala Arg Ala
            820                 825                 830

Phe Ile Leu Ser Cys Phe Glu Pro Asp Pro His Lys Arg Ala Thr Thr
        835                 840                 845

Ala Glu Leu Leu Arg Glu Gly Phe Leu Arg Gln Val Asn Lys Gly Lys
    850                 855                 860

Lys Asn Arg Ile Ala Phe Lys Pro Ser Glu Gly Pro Arg Gly Val Val
865                 870                 875                 880

Leu Ala Leu Pro Thr Gln Gly Glu Pro Met Ala Thr Ser Ser Ser Glu
                885                 890                 895
```

-continued

```
His Gly Ser Val Ser Pro Asp Ser Asp Ala Gln Pro Asp Ala Leu Phe
            900                 905                 910

Glu Arg Thr Arg Ala Pro Arg His His Leu Gly His Leu Leu Ser Val
        915                 920                 925

Pro Asp Glu Ser Ser Ala Leu Glu Asp Arg Gly Leu Ala Ser Ser Pro
    930                 935                 940

Glu Asp Arg Asp Gln Gly Leu Phe Leu Leu Arg Lys Asp Ser Glu Arg
945                 950                 955                 960

Arg Ala Ile Leu Tyr Lys Ile Leu Trp Glu Glu Gln Asn Gln Val Ala
                965                 970                 975

Ser Asn Leu Gln Glu Cys Val Ala Gln Ser Ser Glu Glu Leu His Leu
            980                 985                 990

Ser Val Gly His Ile Lys Gln Ile Ile Gly Ile Leu Arg Asp Phe Ile
        995                 1000                1005

Arg Ser Pro Glu His Arg Val Met Ala Thr Thr Ile Ser Lys Leu Lys
    1010                1015                1020

Val Asp Leu Asp Phe Asp Ser Ser Ser Ile Ser Gln Ile His Leu Val
1025                1030                1035                1040

Leu Phe Gly Phe Gln Asp Ala Val Asn Lys Ile Leu Arg Asn His Leu
                1045                1050                1055

Ile Arg Pro His Trp Met Phe Ala Met Asp Asn Ile Ile Arg Arg Ala
            1060                1065                1070

Val Gln Ala Ala Val Thr Ile Leu Ile Pro Glu Leu Arg Ala His Phe
        1075                1080                1085

Glu Pro Thr Cys Glu Thr Glu Gly Val Asp Lys Asp Met Asp Glu Ala
    1090                1095                1100

Glu Glu Gly Tyr Pro Pro Ala Thr Gly Pro Gly Gln Glu Ala Gln Pro
1105                1110                1115                1120

His Gln Gln His Leu Ser Leu Gln Leu Gly Glu Leu Arg Gln Glu Thr
                1125                1130                1135

Asn Arg Leu Leu Glu His Leu Val Glu Lys Glu Arg Glu Tyr Gln Asn
            1140                1145                1150

Leu Leu Arg Gln Thr Leu Glu Gln Lys Thr Gln Glu Leu Tyr His Leu
        1155                1160                1165

Gln Leu Lys Leu Lys Ser Asn Cys Ile Thr Glu Asn Pro Ala Gly Pro
    1170                1175                1180

Tyr Gly Gln Arg Thr Asp Lys Glu Leu Ile Asp Trp Leu Arg Leu Gln
1185                1190                1195                1200

Gly Ala Asp Ala Lys Thr Ile Glu Lys Ile Val Glu Glu Gly Tyr Thr
                1205                1210                1215

Leu Ser Asp Ile Leu Asn Glu Ile Thr Lys Glu Asp Leu Arg Tyr Leu
            1220                1225                1230

Arg Leu Arg Gly Gly Leu Leu Cys Arg Leu Trp Ser Ala Val Ser Gln
        1235                1240                1245

Tyr Arg Arg Ala Gln Glu Ala Ser Glu
    1250                1255


<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence:
      hexahiatidine affinity tag (His)

<400> SEQUENCE: 7
```

His His His His His His
  1               5

<210> SEQ ID NO 8
<211> LENGTH: 200
<212> TYPE: PRT
<213> ORGANISM: Artificial Sequence
<220> FEATURE:
<223> OTHER INFORMATION: Description of Artificial Sequence:synthetic
      poly-Gly flexible linker
<220> FEATURE:
<221> NAME/KEY: MOD_RES
<222> LOCATION: (6)..(200)
<223> OTHER INFORMATION: Gly residues from position 6 to 200 may be
      present or absent

<400> SEQUENCE: 8

Gly Gly Gly Gly Gly Gly Gly Gly Gly Gly Gly Gly Gly Gly Gly Gly
  1               5                  10                  15

Gly Gly Gly Gly Gly Gly Gly Gly Gly Gly Gly Gly Gly Gly Gly Gly
             20                  25                  30

Gly Gly Gly Gly Gly Gly Gly Gly Gly Gly Gly Gly Gly Gly Gly Gly
         35                  40                  45

Gly Gly Gly Gly Gly Gly Gly Gly Gly Gly Gly Gly Gly Gly Gly Gly
     50                  55                  60

Gly Gly Gly Gly Gly Gly Gly Gly Gly Gly Gly Gly Gly Gly Gly Gly
 65                  70                  75                  80

Gly Gly Gly Gly Gly Gly Gly Gly Gly Gly Gly Gly Gly Gly Gly Gly
                85                  90                  95

Gly Gly Gly Gly Gly Gly Gly Gly Gly Gly Gly Gly Gly Gly Gly Gly
            100                 105                 110

Gly Gly Gly Gly Gly Gly Gly Gly Gly Gly Gly Gly Gly Gly Gly Gly
        115                 120                 125

Gly Gly Gly Gly Gly Gly Gly Gly Gly Gly Gly Gly Gly Gly Gly Gly
    130                 135                 140

Gly Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Gly Gly Gly
                165                 170                 175

Gly Gly Gly Gly Gly Gly Gly Gly Gly Gly Gly Gly Gly Gly Gly Gly
            180                 185                 190

Gly Gly Gly Gly Gly Gly Gly Gly
        195                 200

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence:mouse ASKRK
      C-terminal peptide sequence for generating
      anti-mASKRK antibodies

<400> SEQUENCE: 9

Ser Gln His Arg Arg Gln Met Gln Glu Ser Ser Gln
  1               5                  10

<210> SEQ ID NO 10
<211> LENGTH: 14
<212> TYPE: PRT
<213> ORGANISM: Artificial Sequence -continued

```
<220> FEATURE:
<223> OTHER INFORMATION: Description of Artificial Sequence:human ASKRK
      C-terminal peptide sequence for generating
      anti-hASKRK antibodies

<400> SEQUENCE: 10

Tyr Arg Arg Ala Gln Glu Ala Ser Glu Thr Lys Asp Lys Ala
  1               5                  10
```

What is claimed is:

1. An isolated nucleic acid encoding a polypeptide comprising SEQ ID NO:2.

2. The isolated nucleic acid of claim 1, wherein the nucleic acid comprises SEQ ID NO:1.

3. An expression vector comprising the nucleic acid of claim 1.

4. A host cell in vitro comprising the expression vector of claim 3.

5. The host cell of claim 4, wherein the host cell is a pancreatic beta cell.

* * * * *